US010324062B2

(12) United States Patent
Denenberg et al.

(10) Patent No.: US 10,324,062 B2
(45) Date of Patent: Jun. 18, 2019

(54) METHOD AND APPARATUS FOR MEASUREMENT OF MATERIAL CONDITION

(71) Applicant: JENTEK Sensors, Inc., Waltham, MA (US)

(72) Inventors: Scott A Denenberg, Boston, MA (US); Yanko K Sheiretov, Waltham, MA (US); Neil J Goldfine, Indian Harbour Beach, FL (US); Don Straney, Cambridge, MA (US); Leon B Kristal, Waltham, MA (US)

(73) Assignee: JENTEK Sensors, Inc., Marlborough, MA (US)

( * ) Notice: Subject to any disclaimer, the term of this patent is extended or adjusted under 35 U.S.C. 154(b) by 437 days.

(21) Appl. No.: 15/030,094

(22) PCT Filed: Oct. 22, 2014

(86) PCT No.: PCT/US2014/061825
§ 371 (c)(1),
(2) Date: Apr. 18, 2016

(87) PCT Pub. No.: WO2015/061487
PCT Pub. Date: Apr. 30, 2015

(65) Prior Publication Data
US 2016/0274060 A1    Sep. 22, 2016

Related U.S. Application Data

(60) Provisional application No. 62/009,771, filed on Jun. 9, 2014, provisional application No. 61/894,191, filed on Oct. 22, 2013.

(51) Int. Cl.
*G01N 27/90*     (2006.01)
*G01N 27/02*     (2006.01)
*G01R 27/02*     (2006.01)

(52) U.S. Cl.
CPC ..... *G01N 27/9046* (2013.01); *G01N 27/9073* (2013.01); *G01R 27/02* (2013.01)

(58) Field of Classification Search
CPC . G01N 27/9046; G01N 27/9073; G01R 27/02
See application file for complete search history.

(56) References Cited

U.S. PATENT DOCUMENTS 4,303,885 A    12/1981   Davis
4,322,683 A     3/1982   Vieira
(Continued)

OTHER PUBLICATIONS

International Preliminary Report on Patentability for International Application No. PCT/US2014/061825. Report dated Apr. 26, 2016.
(Continued)

*Primary Examiner* — Huy Q Phan
*Assistant Examiner* — Adam S Clarke
(74) *Attorney, Agent, or Firm* — Zachary M. Thomas

(57) ABSTRACT

System and method for characterizing material condition. The system includes a sensor, impedance instrument and processing unit to collect measurements and assess material properties. A model of the system may be used to enable accurate measurements of multiple material properties. A cylindrical model for an electromagnetic field sensor is disclosed for modeling substantially cylindrically symmetric material systems. Sensor designs and data processing approaches are provided to focus the sensitivity of the sensor to localize material conditions. Improved calibration methods are shown. Sizing algorithms are provided to estimate the size of defects such as cracks and corrosion. Corrective measures are provided where the actual material configuration differs from the data processing assumptions. Methods are provided for use of the system to characterize material condition, and detailed illustration is given for corrosion, stress, weld, heat treat, and mechanical damage assessment.

4 Claims, 52 Drawing Sheets

(56) References Cited

U.S. PATENT DOCUMENTS

Figure 1:
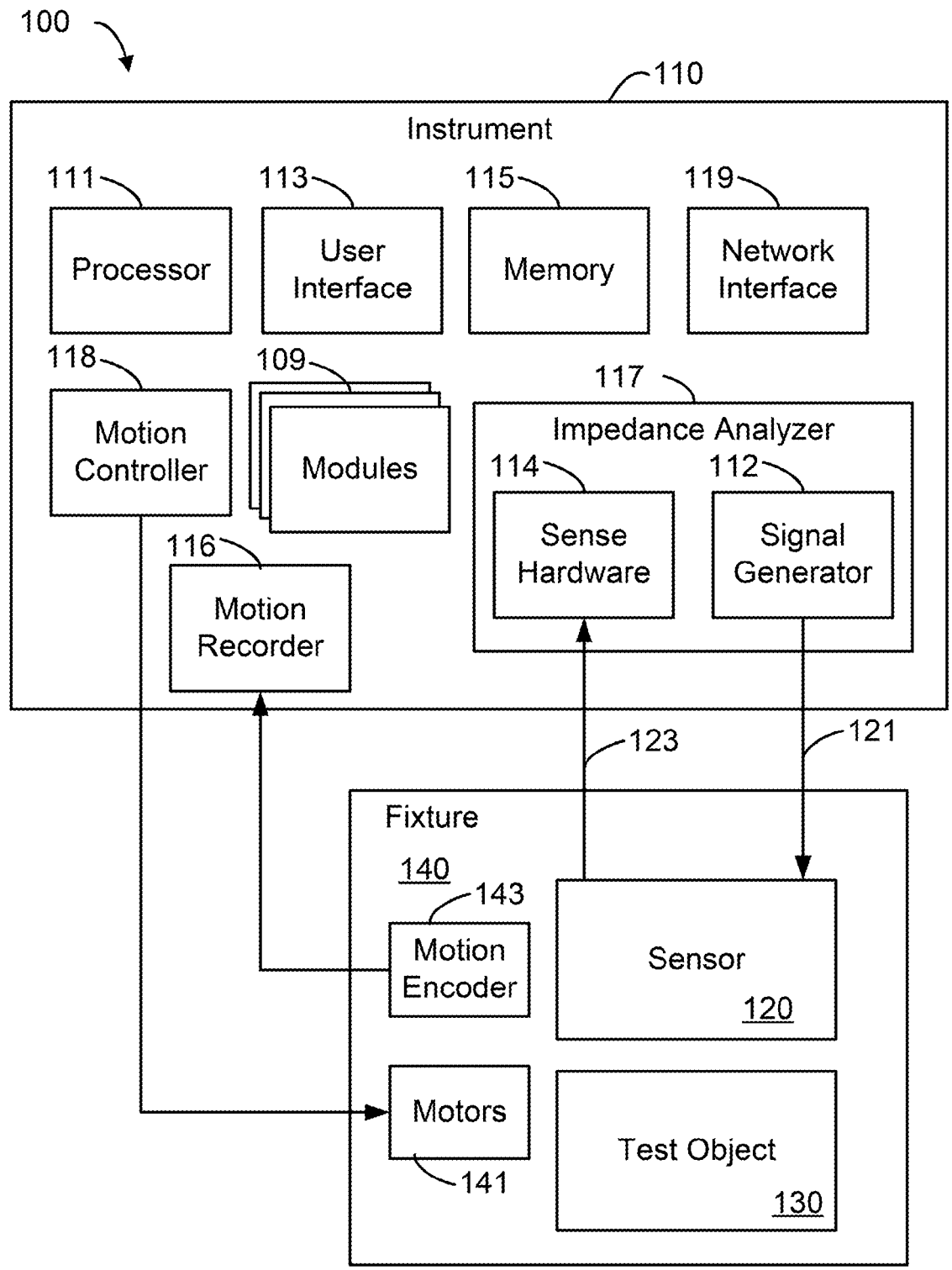

| | | | |
|---|---|---|---|
| 4,496,904 A | 1/1985 | Harrison | |
| 7,385,392 B2 | 6/2008 | Schlicker | |
| 2002/0163333 A1 | 11/2002 | Schlicker | |
| 2003/0227288 A1 | 12/2003 | Lopez | |
| 2004/0056654 A1* | 3/2004 | Goldfine | G01N 27/9013 324/239 |
| 2004/0066189 A1 | 4/2004 | Lopez | |
| 2005/0127908 A1* | 6/2005 | Schlicker | G01N 27/023 324/240 |
| 2008/0109189 A1* | 5/2008 | Bauer | G01D 5/202 702/189 |
| 2009/0319212 A1* | 12/2009 | Cech | B60R 21/0136 702/65 |
| 2010/0327953 A1* | 12/2010 | Lee | H03K 17/962 327/517 |

OTHER PUBLICATIONS

International Search Report for International application No. PCT/US2014/061825, dated Apr. 20, 2015, World Intellectual Property Organization, International Bureau.

* cited by examiner

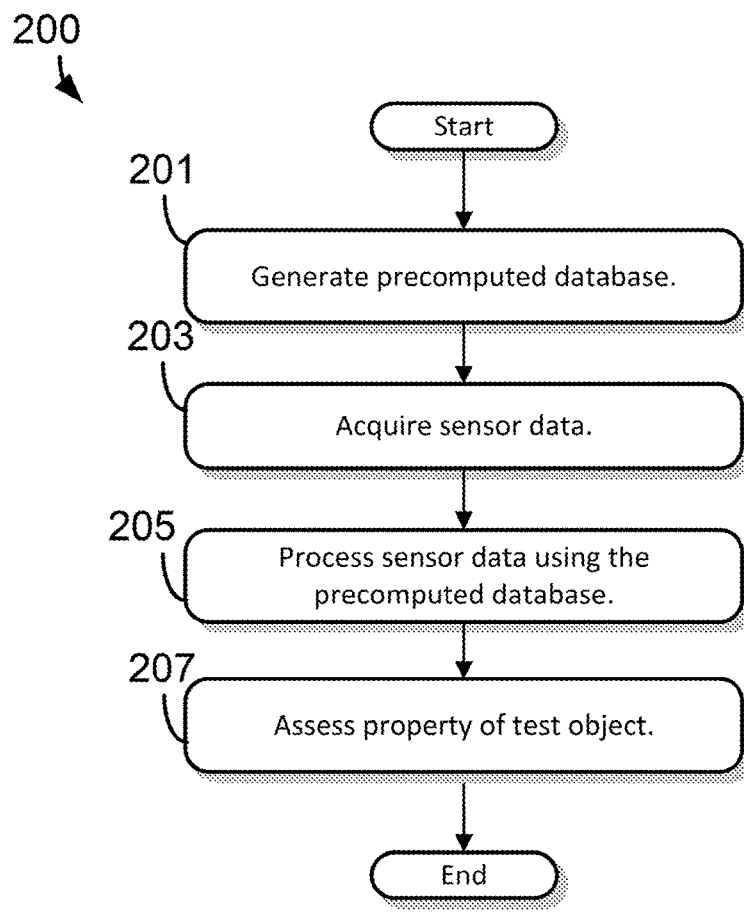
FIG. 2
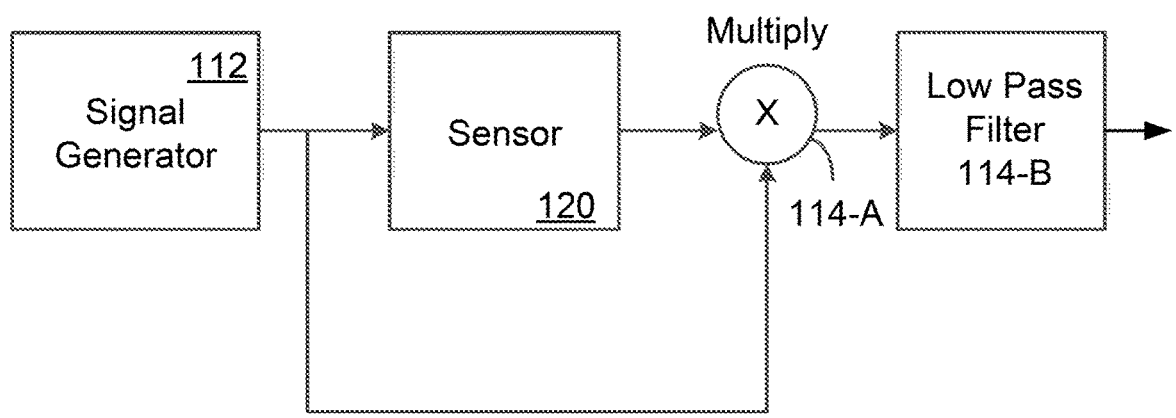
FIG. 3   *(Prior Art)*

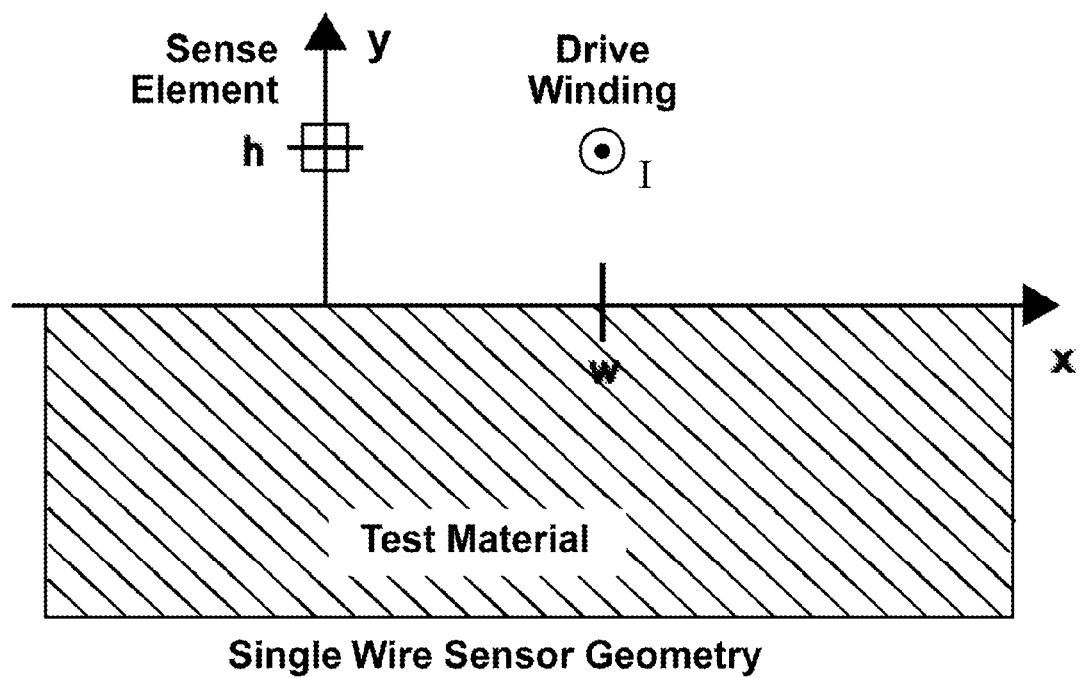
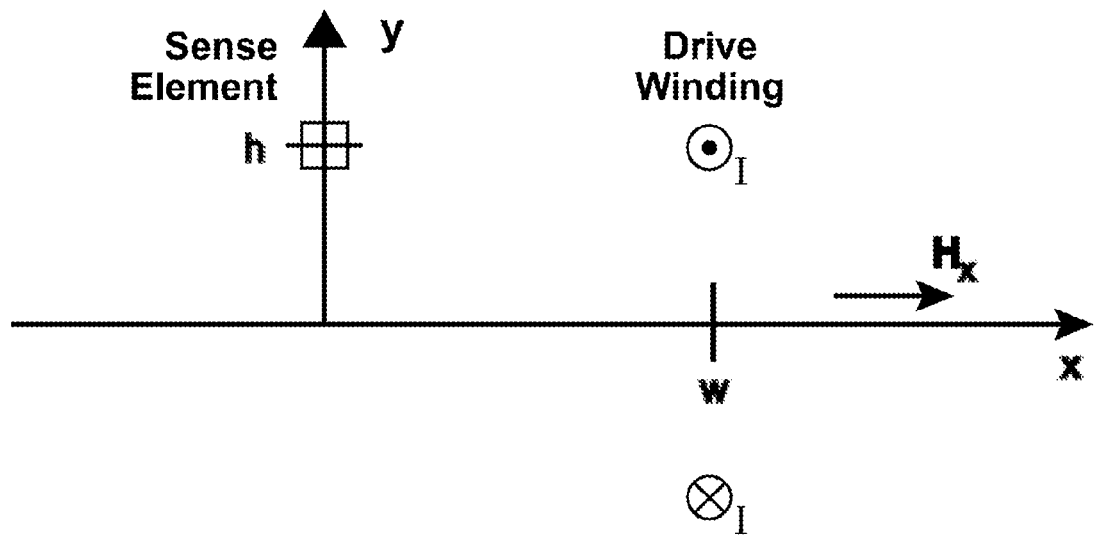
FIG. 7

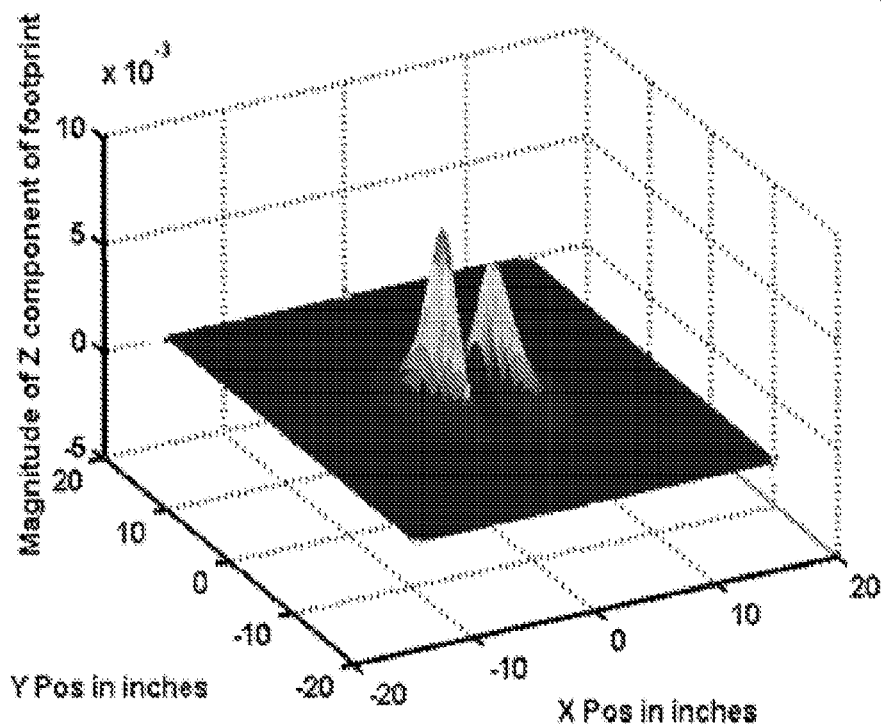
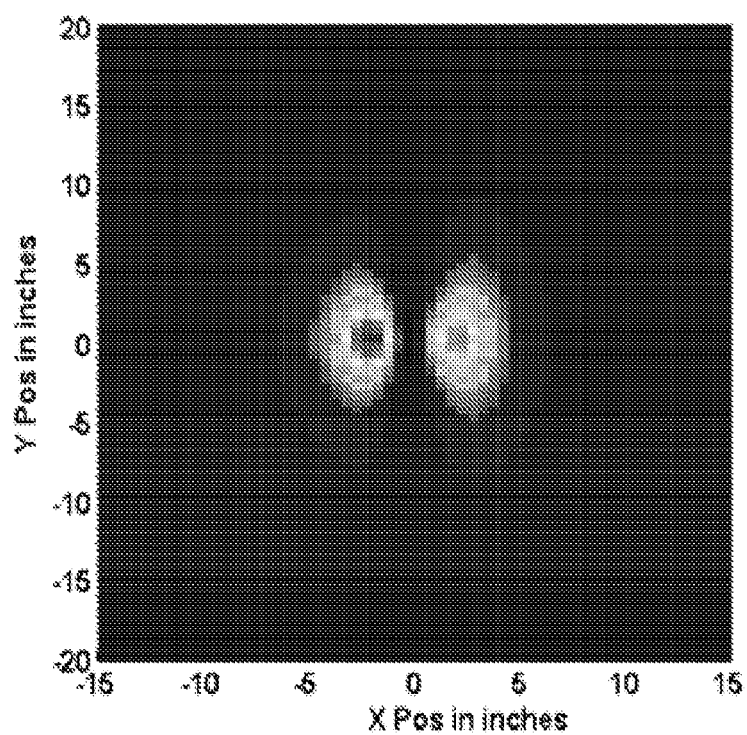
FIG. 10

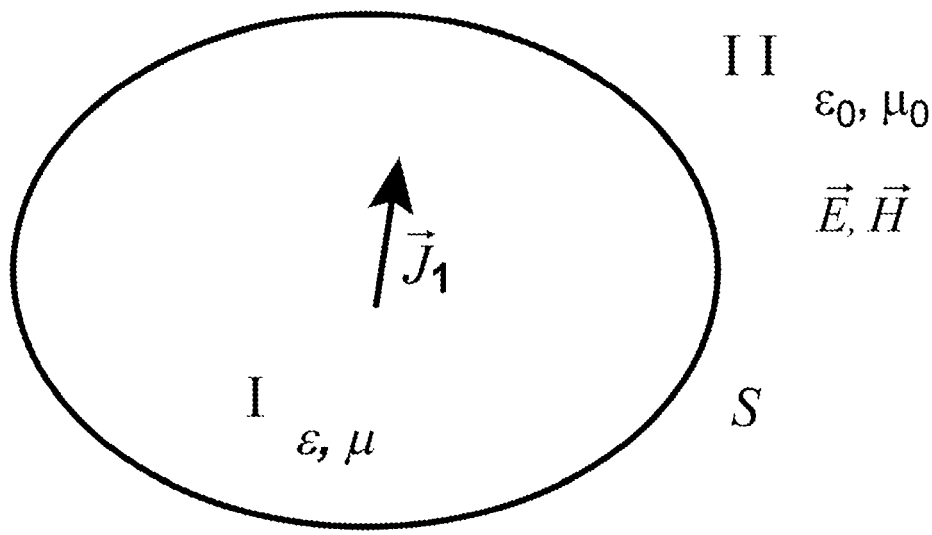
The geometry of the problem.
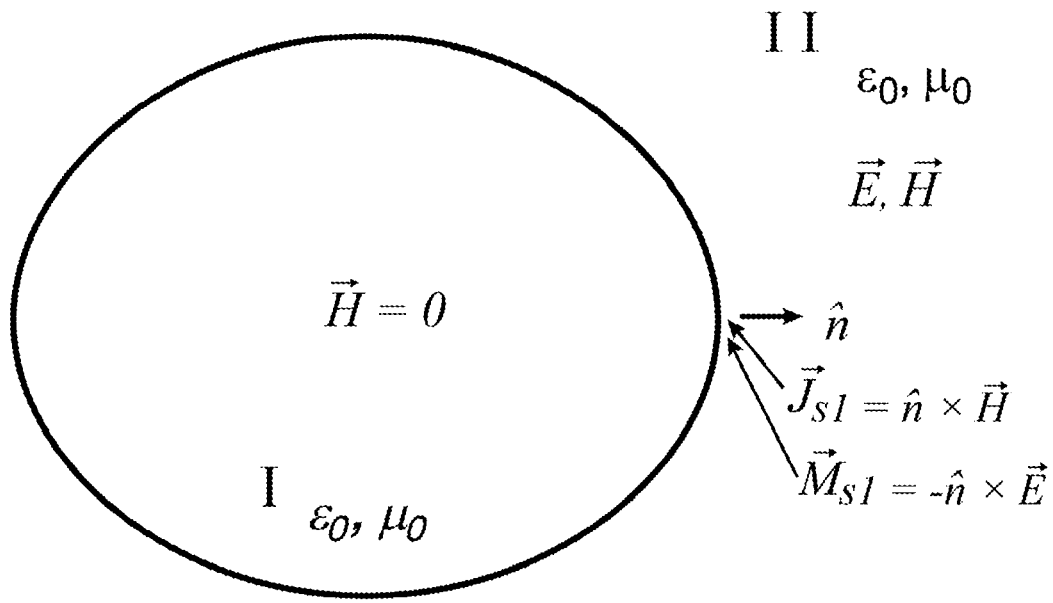
Love's equivalence for Region II.
FIG. 12

| Response Sizes | | | Estimated Flaw Sizes | | |
|---|---|---|---|---|---|
| Length | Width | Depth | Length | Width | Depth |
| 5.3" | 5.9" | 0.0248" | 4.2" | 6.3" | 0.095" |
| 5.1" | 5.9" | 0.0248" | 4.0" | 6.3" | 0.092" |
| 5.5" | 5.9" | 0.0248" | 4.4" | 6.4" | 0.099" |
| .3" | 5.7" | 0.0248" | 4.1" | 6.2" | 0.093" |
| .3" | 6.1" | 0.0248" | 4.2" | 6.6" | 0.096" |
| .3" | 5.9" | 0.022" | 4.0" | 6.2" | 0.088" |
| .3" | 5.9" | 0.028" | 4.4" | 6.5" | 0.105" |

FIG. 42

5300

Use sensor data at one location to estimate the pipe magnetic permeability, electrical conductivity, and the sensor liftoff. The pipe wall is assumed based on a nominal value or a value determined by an independent method.

Use sensor data to estimate the pipe magnetic permeability, wall thickness, and the sensor liftoff. The pipe electrical conductivity is assumed based on the previous step.

FIG. 53

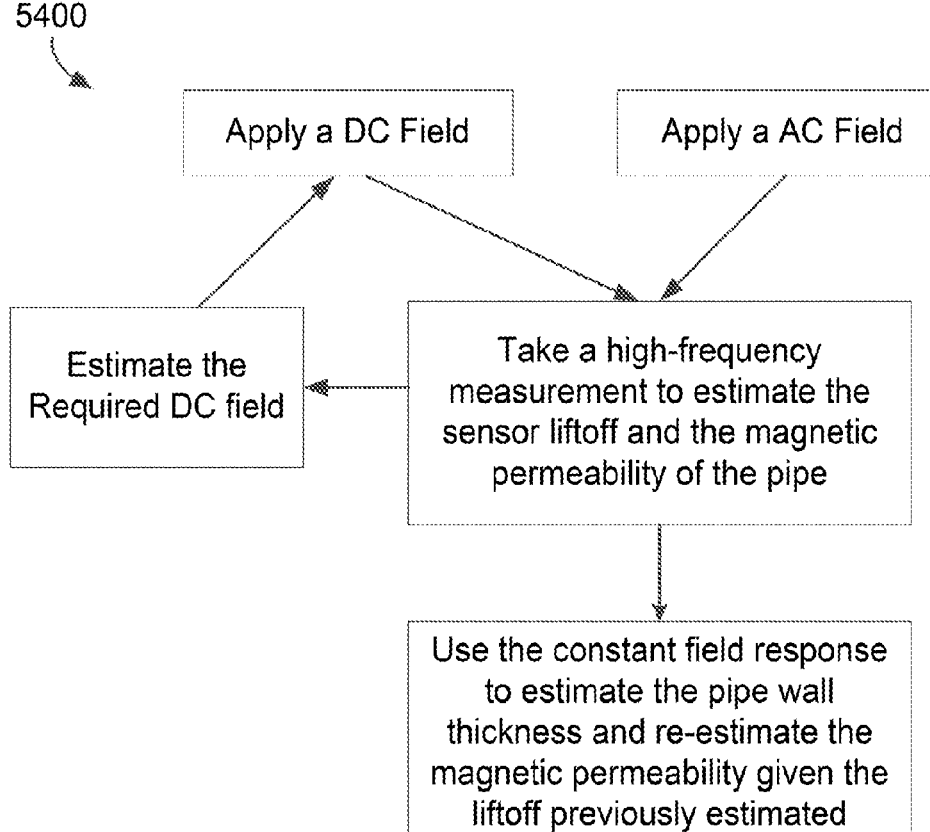

FIG. 54

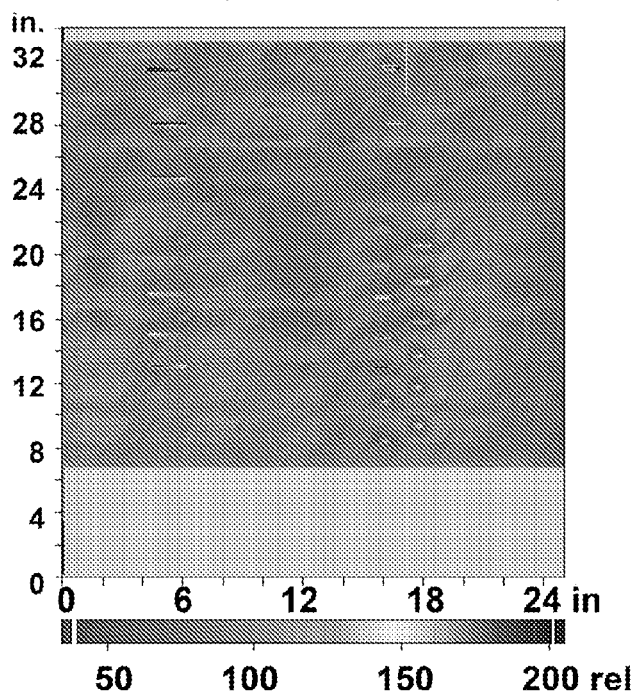
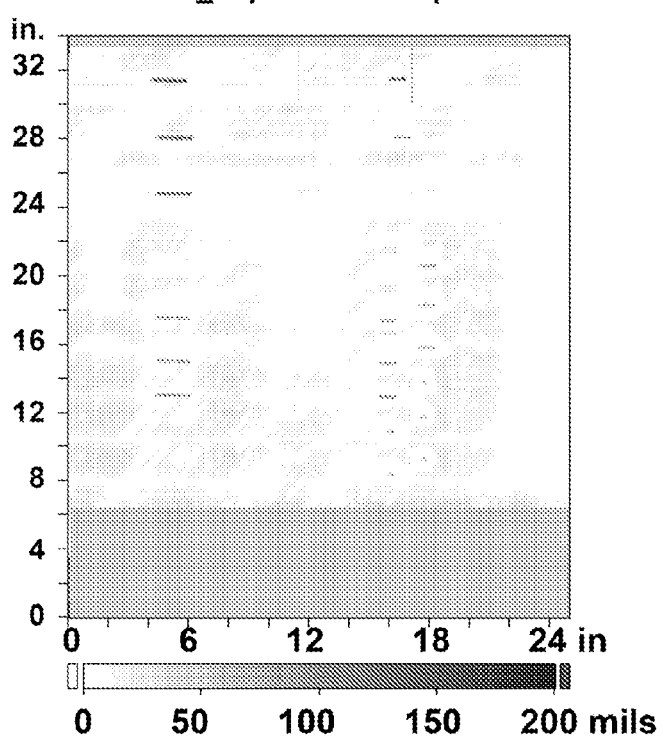
FIG. 61 n Sensor Arrays
Each with dedicated
linear drive provide full coverage
across thickness of sheet

METHOD AND APPARATUS FOR MEASUREMENT OF MATERIAL CONDITION This application claims the benefit of International Application No. PCT/US2014/061825 with an international filing date of Oct. 22, 2014, which itself claims priority under 35 U.S.C. § 119(e) to U.S. Provisional Application No. 61/894,191, filed Oct. 22, 2013, and U.S. Provisional Application No. 62/009,771, filed Jun. 9, 2014. The entire teachings of the above applications are incorporated herein by reference.

The entire teachings of the above applications are incorporated herein by reference.

BACKGROUND

Inspection of material condition is an important aspect of cost effective maintenance of high value assets (such as aircraft, trains, and other vehicles; transportation infrastructure; refineries, pipelines, other oil and gas infrastructure, to name a few). Major factors driving inspection costs include the cost of the equipment, the amount of time it takes to perform the inspection, the amount of disassembly required to perform the inspection, the cost of reassembly (or repair if the inspection is destructive), and the expertise and number of required operators.

Defects of interest vary by application, and include cracks, fatigue, corrosion, stress corrosion crack colonies, inclusions, pits, dents, gauges, corrosion-fatigue, cracks in dents, and other combinations of defects and other defects caused by service, manufacturing, or other events and processes.

A variety of sensor technologies have been developed to support the inspection needs of industry. Electromagnetic methods for inspection include Radiography, eddy-current testing (ET), Magnetic Flux Leakage (MFL), Magnetic Particle Testing (MPT or MT), Electromagnetic Acoustic Transmission (EMAT) and other variations on these and other methods.

In general, for advanced ET methods transimpedance is measured as indicated in FIG. 3. A signal generator 112 creates a sinusoidal waveform signal. This signal is applied to the system being tested, in this example, sensor 120. Multiplier 114-A multiplies the output of sensor 120 with the original signal and the result is passed through a low pass filter (LPF) 114-B to eliminate all frequency components except zero. The output of the filter is the real component of the transimpedance. To obtain the imaginary (90° phase) component, the reference signal used in the multiplication is shifted by 90°.

Multiplication and low-pass filtering is accomplished with electronics operating on the analog signal output from signal generator 112 and sensor 120. The output of LPF 114-B may be converted by an analog to digital converter for later processing or presentation on a digital display. There is a certain length of time that needs to pass between the time the signal is applied and a valid measurement can be taken, due to settling time of LPF 114-B.

SUMMARY

Some embodiments relate to an impedance instrument comprising a signal generator and a sensing channel. The signal generator is configured to generate an in-phase reference signal, a quadrature reference signal, and an electrical signal oscillating at a first excitation frequency, wherein the in-phase reference signal is a digital precursor to the electrical signal, and the quadrature reference signal is a version of the in-phase reference signal shifted one-quarter period. The sensing channel has an analog-to-digital converter to digitize a response signal and a module to process successive digitized samples of the digitized response signal with each of the in-phase and quadrature reference signals, to produce an impedance measurement.

The in-phase reference signal may have the same phase as the electrical signal. The sensing channel may be among a plurality of parallel sensing channels each having a respective module configured to simultaneously process a respective digitized response signal with the in-phase reference signal and quadrature reference signal.

The module may be configured to simultaneously process the successive digitized samples of the digitized response signal by independently at least multiplying the digitized samples by the in-phase and quadrature reference signals. The module of the sense channel may be implemented as a field-programmable gate array (FPGA). The module may produce a real part of the impedance measurement from the digitized samples processed with the in-phase reference signal, and the module produces an imaginary part of the impedance measurement from the digitized samples processed with the quadrature reference signal.

The signal generator may be further configured to generate the electrical signal such that the electrical signal additionally oscillates at a second excitation frequency. The signal generator may also in-phase and quadrature reference signals at the second frequency.

In some embodiments, the impedance instrument further comprises a combiner module may be configured to add the first and second in-phase reference signal into a single combiner output signal. The combiner module is further configured to apply a separate weight to the first and second in-phase reference signals before adding.

The processing of the successive digital samples by the module may include multiplying the successive digital samples by corresponding samples of the in-phase reference signal and adding the result to a first running sum; and multiplying the successive digital samples by corresponding samples of the quadrature reference signal and adding the result to a second running sum.

The impedance instrument may include a non-transient computer storage medium storing a database of precomputed impedances for a sensor and test object; and a processor configured to receive the impedance measurement from the sensing channel and process the impedance with the database to determine a property of the test object.

Some embodiments are directed to a method of operating the impedance instrument of claim A1. The method may comprise acts of operably connecting the impedance instrument to a sensor; placing the sensor proximal to a surface of a test object coated with a coating; exciting the electrical signal into the sensor using the signal generator, wherein a skin depth at the first excitation frequency is greater than a thickness of the coating; measuring the impedance with the sensing channel, the impedance having a phase of less than 1 degree; and processing the impedance measurement to determine a property of the test object.

In some embodiments of the method, the sensing channel is among a plurality of identical sensing channels, the sensor comprises a plurality of sensing elements, operably connecting the impedance instrument to the sensor comprises connecting each of the plurality of sensing channels to a respective sensing element, the measuring of the impedance is performed on each of the plurality of sensing channels, and the processing is performed to each of the impedance measurements to produce an image of the property of the test object.

In some embodiments the test object is a biological material and the method further comprises assessing health of the biological material based on the property. The biological material may be a brain and the property may be a condition of the brain. The property may be damage to the test object and the method may further comprise quantifying the damage. The property may be a temperature of a subsurface location in the test object. The property may be moisture ingress into the test object. The property may be moisture ingress and the image may be a map indicating susceptibility to corrosion.

The acts of exciting, measuring and processing may be repeated at a plurality of times, and changes in the property may be monitored over time. The sensor may be maintained in a fixed position relative to the test object throughout the repetitions.

The measuring act may include performing a plurality of impedance measurements on each sensing channel and scanning the sensor across the coated surface of the test object during measuring.

Some embodiments are directed to a method of measuring impedance. The method may include generating a digital, in-phase reference signal and a digital, quadrature reference signal, the quadrature reference signal is a version of the in-phase reference signal shifted one-quarter period; providing an electrical signal oscillating at a first frequency to a device having two or more ports, the electrical signal having been generated based on the in-phase reference signal; digitizing a response signal from the device; processing digitized samples of the response signal with the in-phase reference signal to measure a first component of the impedance; processing the digitized samples of the response signal with the quadrature reference signal to measure a second component of the impedance; and providing the first and second component of the impedance as a representation of the impedance of the device.

The device may be a sensor, such as an eddy current sensor or a magnetoresistive sensor.

Impedance may be represented in complex form having a real and an imaginary part, and the first component of the impedance is the real part, and the second component of the impedance is the imaginary part.

Another aspect relates to an impedance instrument having a signal generator and a sense channel. The signal generator may have a reference signal generator, a combiner, and a module. The reference signal generator is configured to generate a reference signals at a plurality of frequencies, each frequency having an in-phase reference signal and a quadrature reference signal, the quadrature reference signal being a version of the in-phase reference signal shifted one-quarter period. The combiner to generate a combined signal by applying a weight to each in-phase reference signal and adding the weighted in-phase reference signals. The module is configured to generate and output an excitation signal by at least amplifying the combined signal. The sense channel has an analog to digital converter and a multiply/accumulate module. The ADC digitizes a response signal into n successive digitized samples. The multiply/accumulate module to separately multiply the n successive digitized samples by respective samples of respective reference signals, to separately add products of the multiply associated with each reference signal, and divide each total by n to produce complex impedance measurements at each of the plurality of frequencies.

Another aspect relates to a system for estimating properties from sensor measurements. The system has a sensor, a calibration module, an impedance analyzer, a MIM module, and a recalibration module. The impedance analyzer measures raw impedance data from the sensor. The calibration module is configured to calibrate the raw impedance data using reference data. The MIM module is configured to use a multivariate inverse method to generate reference set properties using a reference set of the calibrated impedance data, a precomputed database, and property assumptions. The recalibration module is configured to recalibrate the calibrated impedance data using the reference set properties, producing recalibrated data. The MIM module is further configured to use the multivariate inverse method to generate estimated properties using the recalibrated data and the precomputed database.

The sensor may be placed proximal to a test object during measurement of the raw impedance data by the impedance analyzer. The reference set of calibrated impedance data may be acquired as raw impedance data at a location on the test object having nominal properties, and the property assumptions comprise at least one of the nominal property.

The system may also include an assessment module configured to determine if the test object is acceptable based on the estimated properties. The system may further include a post-processing module configured to cross-correlate a select property among the estimated properties with a known spatial variation of said select property that results from measurement at a discrete flaw. The assessment module may make the assessment based at least in part on the select property after the cross correlation.

The system may further include a scanner configured to hold and move the sensor along the test object as the impedance analyzer measured raw impedance data and an encoder to record the corresponding position of the sensor during measurements. The impedance analyzer may record the raw impedance data with the correspond position of the sensor.

The system may further include a user interface configured to display a spatially registered image indicating an area where the test object was determined to be unacceptable by the assessment module.

In some embodiments, precomputed database is generated from an analytical model of the test object and sensor. The test object and sensor may be approximated by the analytical model as having cylindrical symmetry. The analytical model for the sensor may include the drive winding of these sensor, such that the drive winding has a portion that is circumferential, having a constant radius and constant axial position along a center axis of cylindrical symmetry.

The test object may be a pipe having insulation and weather-jacket and the estimated properties may include sensor lift-off, insulation thickness, and pipe wall thickness.

The sensor may have first and second arrays of sensing elements, each element of the first array having a respective element of the second array. The system may further include a preprocessing module configured to combine calibrated impedance measurements from the respective sensing elements of the arrays prior to use of the calibrated impedance data by the MIM module to generate the reference set.

The sensor may include an array of sensing elements and the impedance analyzer may measure raw impedance data at a plurality of frequencies for each of the sensing elements in the array.

Another aspect relates to a method of estimating properties of a test object from raw impedance data. The method includes obtaining a reference set of impedance data measured on the test object; calibrating the reference set using calibration data; estimating calibration properties for the raw impedance data using the calibrated reference subset; measuring the raw impedance data with a sensor on the test object; calibrating the raw impedance measurements using the calibration properties; estimating the properties of the test object using a pre-computed database.

The reference set of impedance data may be obtained using the sensor. The calibration data may be data obtained by the sensor with any test materials outside a range of sensitivity of the sensor. The calibration data may be taken on a reference part other than the test object.

Estimating the calibration properties may include applying a multivariate inverse method to the calibrated reference subset, the multivariate inverse method utilizing the precomputed database of sensor responses and at least one property assumption for the test object.

In some embodiments, the precomputed database is a first precomputed database for the properties to be estimated, and estimating the calibration properties comprises applying a multivariate inverse method to the calibrated reference subset, the multivariate inverse method utilizing a second precomputed database for a subset of the properties to be estimated. The precomputed database may be generated from an analytical model of the test object and sensor. The test object and sensor may be approximated by the analytical model as having cylindrical symmetry. The analytical model for the sensor may include a drive winding having a portion that is circumferential, having a constant radius and constant axial position along a center axis of cylindrical symmetry. The test object may be a pipe and the sensor may have magnetoresistive sensing elements.

The method may further comprise correlating an electrical property among the estimated properties with depth of a crack. The correlation may be accomplished using a correlation relationship determined from empirical data on representative defects and a crack length is also determined using a spatial image generated from the response at multiple locations on the test object. The correlation may be accomplished using a correlation relationship determined from computer simulated data for representative defect geometries.

The crack may be among a plurality of cracks within a stress corrosion crack colony and the depth of a deepest crack is estimated. Correlating may include an effect of a second crack on the electrical property. The effect of the second crack on the correlation may be determined using a computer model. The computer module may be used to compute a scale factor for the depth.

A precomputed database may be used to estimate the lift-off before and after the crack and to determine an effective conductivity change at the crack for all locations along the crack.

Measuring the raw impedance data may be performed with a drive winding of the sensor orientated perpendicularly to a length direction of the crack and the sensor is moved in the direction of the crack length. Measuring the raw impedance data may performed with a drive winding of the sensor orientated between 30 and 60 degrees relative to a length direction of the crack and the sensor is moved in the direction of the crack length.

Another aspect relates to an inspection apparatus for determining quality of a weld in a test object. The apparatus may include at least one sensing segment, each sensing segment having an array of sensing elements at a fixed distance from at least one linear drive conductor; an impedance instrument having a signal generator configured to generate an electrical current at least one excitation frequency, said signal generator electrically connected to provide the electrical current to the drive conductor; and a plurality of parallel sensing channels, each sensing channel dedicated to a sensing element of the at least one sensing segment and configured to simultaneously measure real and imaginary components of an impedance associated with the respective sensing element at each of the at least one excitation frequencies; a scanning apparatus configured to move the at least one sensing segment relative to the weld as the impedance instrument measures impedances from the at least one sensing segment, a MIM module configured to apply a multivariate inverse method to the measured impedances to determine the magnetic permeability as a function of position in the test object, and a post-processing module configured to compute a feature of the magnetic permeability response that correlates with weld quality.

The array of sensing elements may be an array of conductive sensing loops.

The scanning apparatus may be in the form of an in-line-inspection tool for pipeline inspection, multiple sensing arrays are included with individual linear drive conductors on retractable arms with arcs that match the internal curvature of a pipe to be inspected.

The sensing elements may be inductive and a speed of the tool varies as the tool experiences varied pipeline elevation and the data rate is equal to a multiple of the time for a single drive current cycle at the lowest of one or more prescribed frequencies and where a precomputed database of sensor responses is used to convert the response at, each sensing element into a magnetic permeability and lift-off value.

The linear drive conductor may be oriented circumferentially and the magnetic permeability provides a combined measure of both metallurgical changes and axial stress.

Multiple linear drive conductors may be included at equal spacing around the circumference but are oriented axially to provide a measure of the magnetic permeability in the circumferential, hoop, direction.

The post-processing module may correlate the magnetic permeability with stress in the weld and the weld quality is assessed based on the tensile stresses not exceeding a prescribed limit.

The test object may comprise a pipe with a coating on the outer surface, the linear drive segment may be oriented axially and the scanning apparatus enables movement of the sensor array in the circumferential direction on the outer surface of coating of the pipe, and the MIM module may use a precomputed database to estimate the magnetic permeability in the circumferential direction.

The test object may be a pipe and the linear drive conductor may be oriented at 45 degrees relative to a central axis of the pipe so that both the hoop and longitudinal components of stress affect the magnetic permeability estimate and the magnetic permeability is determined using a precomputed database of sensor responses.

Another aspect relates to a method comprising operating the inspection apparatus of claim F1 to perform inspection of a weld before post-weld heat treatment (PWHT); heat treating the weld; and operating the inspection apparatus of claim F1 to perform inspection of a weld after PWHT, wherein the post-processing module computes the feature of the magnetic permeability response that correlates with weld quality using inspection results from both before and after PWHT.

The feature of the magnetic permeability computed by the post-processing module may be a change in a width of a response for the response after PWHT when compared to the response before PWHT. The feature of the magnetic permeability may be a reduction in a highest local peak of the magnetic permeability near a center line of the weld after PWHT when compared to the response before PWHT. The feature of the magnetic permeability response may be a change in difference between a permeability associated with a base material portion of the test object and a permeability of a region within a heating coil covered region neighboring the weld for the magnetic permeability after PWHT when compared to the response before PWHT.

Another aspect relates to a method comprising operating the inspection apparatus to perform inspection of a weld after post-weld heat treatment (PWHT). The method may include determining the relationship between magnetic permeability and stress for the weld, a heat affected zone proximal to the weld, and the base material of the test object by applying stress to small coupons of representative material and developing a correlation relationship between applied stress and the magnetic permeability measured with a sensor that has a similar geometry to the at least one sensing segment.

Another aspect relates to a method comprising operating the inspection apparatus at two or more different times on the test object and using a change in response to determine if the condition of the weld has degraded.

Another aspect relates to a method comprising operating the inspection apparatus of to measure magnetic permeability in two orientations, and producing a measure of anisotropy in the magnetic permeability; assessing weld quality based on the measure of anisotropy.

Another aspect relates to an in-line inspection (ILI) tool comprising a tool body; a plurality of sensing segments, each sensing segment having an array of sensing elements and a drive conductor with an arc-shaped segment; a plurality of armatures, each controlling retraction and protraction of a respective sensing segment with respect to the tool body; an impedance instrument having a signal generator configured to generate an electrical current at a first excitation frequency, said signal generator electrically connected to provide the electrical current to the drive conductor of each of the plurality of sensing segments, and a plurality of parallel sensing channels, each sensing channel dedicated to a sensing element of the plurality of sensing segments and configured to simultaneously measure real and imaginary components of an impedance associated with the respective sensing element at the first excitation frequency; a non-transient computer storage medium storing a precomputed database of sensor responses; and a processor configured to receive the impedance measurements from the impedance instrument and determine (i) a distance between each of the respective sensing elements an internal surface of a test material and (ii) a property of the test material using at least the precomputed database. The at least one sensing segments may comprises first and second sensing segments, and the second sensing segment may be oriented differently than the first.

In some embodiments, the electrical current further comprises a second excitation frequency, the plurality of sensing channels of the impedance instrument are further configured to simultaneously measure real and imaginary components of a second impedance associated with the respective sensing element at the second excitation frequency, the property is magnetic permeability, and the processor is further configured to determine (iii) the pipe wall thickness.

The first excitation frequency may be higher than the second excitation frequency, and the determination of the distance may be made without use of the impedance measured at the second excitation frequency.

The property may be magnetic permeability and the tool further comprises an ultrasonic measurement device configured to measure wall thickness, and wherein the processor utilizes the ultrasonic wall thickness measurement in estimating the magnetic permeability.

The processor may be further configured to determine the conductivity of the test material. The conductivity may be determined by assuming a nominal wall thickness value away from any defect like responses using the precomputed database and at least two frequencies of data. The conductivity estimate may be assumed to be the same at all other locations and the magnetic permeability, wall thickness and lift-off are estimated using the responses at least two frequencies.

The impedance instrument may determine an impedance for each of the plurality of parallel sensing channels, by dividing a voltage of the respective sensing element with the electrical current on the drive conductor.

The arc shaped segment of the drive conductor may be oriented circumferentially. The arc shaped segment of the drive conductor may be oriented between 10 and 50 degrees off of a circumferential orientation. The drive conductor may be wound in a square wave meander with the longer segments in the axial direction The tool may havea tether and a mechanism for allowing the gas or liquid product to flow past the tool to reduce the tool speed.

The array of each sensing segment may include two rows of sensing elements.

The test material may be a pipe. The pipe may be a pipeline.

The property may be a magnetic permeability of the test material.

The impedance instrument may measure the impedance on each of the plurality of parallel sensing channels at least 3,000 times per second.

The tool can provide lift-off correction and magnetic permeability imaging at variable speeds over ranges from less than 1 m/s to over 10 m/s without modification and can correct for lift-off variations of over 1 cm and tool tilting. The lift-off is estimated to correct the magnetic permeability and wall thickness estimates for variable lift-off using a precomputed database. The tilt of the tool may be estimated using the response of sensing elements at least two different axial positions along the tool from two different arc segments to provide an estimate of the tool tilt which is then used to correct a second property estimate using a model. The tool may comprise a plurality of encoders, each encoder configured to record a position of a respective armature, and wherein the processor is further configured to determine an internal surface profile and concentricity response from the recorded encoder positions and the determined distances of the respective sensing elements the internal surface of a test material.

Another aspect relates to a method of operating the ILI tool, the method comprising launching the ILI tool from a cleaning tool pipeline inspection gauge (PIG) (PIG is an acronym for "Pipeline-Inspection Gauge") launcher into a pipe; operating the tool to collect impedance data from the plurality of sensing segments; processing the impedance data to produce processed data, the processed data including distance and property estimates; and retrieving the tool. The method may further include identifying a characteristic response associated with a weld from at least one of the distance and the property; and counting a number of welds passed by the tool.

The property may be a magnetic permeability of the test material and the method may further include producing a crack response from the magnetic permeability; detecting a crack from the crack response; and determining a position of the crack using a position of the tool and a location of the sensing element at a time the crack response was measured.

The crack may be a stress corrosion crack (SCC). The crack may be a seam weld crack. The crack response may be processed to estimate crack depth.

After launching and prior to retrieving the tool, the method may include measuring a first set of impedance data with the impedance instrument while the tool is traveling at a speed under 1 meter per second; and measuring a second set of impedance data with the impedance instrument while the tool is traveling at a speed over 10 meters per second. The method may include operating the processor to process to determine the distance from the first set of impedance data; and operating the processor to process to determine the distance from the second set of impedance data.

The method may include, after launching and prior to retrieving the tool, operating the tool to provide a plurality of measurements of the distance and the property while a speed of the tool within the pipe varies over 5 meters per second.

A tilt of the tool may be computed.

In some embodiments, the method includes producing a damage response from at least one of the distance and the property; and estimating a size of the damage using at least the damage response.

The test material may be a pipe and the damage may be corrosion internal to the pipe. The damage may be internal and external corrosion, and the distance may be used to differentiate the two. The damage may be, for example, mechanical damage, hard spots, a girth weld crack, or, a seam weld crack.

The method may further include producing a post weld heat treat condition response from at least one of the distance and the property; and estimating a quality of a post weld heat treatment to the test material from at least the post weld heat treat condition response.

The method may further include estimating bending stress in the test material from at least one of the distance and the property.

The method may further include comparing the processed data to earlier processed data; and detecting a change in condition of the test material based on the comparison.

The detected change in condition may be a change in corrosion, and the corrosion growth may be quantified. The detected change in condition may be a change in crack size, and the crack growth may be quantified. The detected change in condition may be used to detect cracks.

Another aspect relates to a method for detecting defects in a conducting layer, the method comprising acts of: placing an eddy current sensor proximal to a surface of the conducting layer, the eddy current sensor having a driving winding and a linear array of sensing elements; exciting the drive winding with an electrical current at a first excitation frequency, the first excitation frequency having a depth of penetration between 50% and 150% of a thickness of the conducting layer; measuring a first transimpedance at the first excitation frequency for each sensing element in the linear array of sensing elements using a single, continuous dataset obtained from the respective sensing element; estimating a property of the thin sheet using the first transimpedance; and detecting a defect using the estimated property.

The conducting layer may be moving relative to the sensor at a speed greater than 1 inch per second. In some embodiments, for each sensing element the acts of measuring and estimating are repeated and the property is stored in association with a location on the conducting layer. In some embodiments, a linear portion of the drive winding is spaced from the linear sensing array by a distance less than 10 times the thickness of the conducting layer.

In some embodiments, measuring the transimpedance comprises: multiplying the dataset by an in-phase reference signal; and multiplying the dataset by an quadrature reference signal.

In some embodiments, the electrical current excited in the drive winding further comprises a second excitation frequency higher than the first, the measuring further comprises measuring a second transimpedance at the second excitation frequency for each sensing element in the linear array of sensing elements using the single, continuous dataset obtained from the respective sensing element; and in the detecting, the defect is determined to one of a near side defect, a far side defect, or a through wall defect.

In some embodiments, the estimating comprises: determining a lift-off of the sensor from the conducting layer for the sensing element using the second transimpedance; and determining a thickness and electromagnetic property of the conducting layer using the first transimpedance and the lift-off.

In some embodiments, the method further comprises an act of providing a static magnetic field near the sensor and the conducting layer, the static magnetic field having a magnetic field intensity within the conducting layer which causes a magnetic permeability of the conducting layer to decrease.

In some embodiments, the method further comprises acts of placing a second eddy current sensor having a second drive winding and second linear array of sensing elements proximal to an opposite surface of the conducting layer; and performing the acts of exciting and measuring with the second eddy current sensor.

In some embodiments, the first and second eddy current sensors are spatially aligned with one another, and the drive windings are excited with the electrical current. In some embodiments, the electrical current excited in the drive windings further comprises a second excitation frequency higher than the first, the measuring further comprises measuring second transimpedances at the second excitation frequency for each sensing element of both linear arrays of sensing elements, the estimating comprises determining lift-offs for respective sensing elements of both sensors using the respective second transimpedances, and the estimating further comprises determining the thickness of the conducting layer by subtracting the lift-offs from a known distance between the two sensors. The foregoing is a non-limiting summary of the invention, which is defined by the attached claims.

DETAILED DESCRIPTION

Section A: System Overview

The patent or application file contains at least one drawing executed in color. Copies of this patent or patent application publication with color drawings will be provided by the Office upon request and payment of the necessary fee.

FIG. 1 is a block diagram of a system 100 for inspecting a test object 130. System 100 includes an instrument 110 and a sensor 120. Instrument 110 is configured to provide excitation signals 121 to sensor 120 and measure the resulting response signals 123 of sensor 120. Measured response signals 123 may be measured and processed to estimate properties of interest, such as electromagnetic properties (e.g., conductivity, permeability, and permittivity), geometric properties (e.g., thickness, sensor lift-off), material condition (e.g., fault/no fault), or any other suitable property or combination thereof. (Sensor lift-off is a distance between the sensor and the closest surface of the test object for which the sensor is sensitive to the test object's electrical properties.)

Instrument 110 may include a processor 111, a user interface 113, memory 115, an impedance analyzer 117, and a network interface 119. Though, in some embodiments of instrument 110 may include other combinations of components. While instrument 110 is drawn as a single block, it should be appreciated that instrument 110 may be physically realized as a single "box"; multiple, operably-connected "boxes", or in any other suitable way. For example, in some embodiments it may be desired to provide certain components of instrument 110 as proximal to sensor 120 as practical, while other components of instrument 110 may be located at greater distance from sensor 120.

Processor 111 may be configured to control instrument 110 and may be operatively connected to memory 115. Processor 111 may be any suitable processing device such as for example and not limitation, a central processing unit (CPU), digital signal processor (DSP), controller, addressable controller, general or special purpose microprocessor, microcontroller, addressable microprocessor, programmable processor, programmable controller, dedicated processor, dedicated controller, or any suitable processing device. In some embodiments, processor 111 comprises one or more processors, for example, processor 111 may have multiple cores and/or be comprised of multiple microchips.

Memory 115 may be integrated into processor 111 and/or may include "off-chip" memory that may be accessible to processor 111, for example, via a memory bus (not shown). Memory 115 may store software modules that when executed by processor 111 perform desired functions. Memory 115 may be any suitable type of non-transient computer-readable storage medium such as, for example and not limitation, RAM, a nanotechnology-based memory, one or more floppy disks, compact disks, optical disks, volatile and non-volatile memory devices, magnetic tapes, flash memories, hard disk drive, circuit configurations in Field Programmable Gate Arrays (FPGA), or other semiconductor devices, or other tangible, non-transient computer storage medium.

Instrument 110 may have one or more functional modules 109. Modules 109 may operate to perform specific functions such as processing and analyzing data. Modules 109 may be implemented in hardware, software, or any suitable combination thereof. Memory 115 of instrument 110 may store computer-executable software modules that contain computer-executable instructions. For example, one or more of modules 109 may be stored as computer-executable code in memory 115. These modules may be read for execution by processor 111. Though, this is just an illustrative embodiment and other storage locations and execution means are possible.

Instrument 110 provides excitation signals for sensor 120 and measures the response signal from sensor 120 using impedance analyzer 117. Impedance analyzer 117 may contain a signal generator 112 for providing the excitation signal to sensor 120. Signal generator 112 may provide a suitable voltage and/or current waveform for driving sensor 120. For example, signal generator 112 may provide a sinusoidal signal at one or more selected frequencies, a pulse, a ramp, or any other suitable waveform.

Sense hardware 114 may comprise multiple sensing channels for processing multiple sensing element responses in parallel. Though, other configurations may be used. For example, sense hardware 114 may comprise multiplexing hardware to facilitate serial processing of the response of multiple sensing elements. Sense hardware 114 may measure sensor transimpedance for one or more excitation signals at on one or more sense elements of sensor 120. It should be appreciated that while transimpedance (sometimes referred to simply as impedance), may be referred to as the sensor response, the way the sensor response is represented is not critical and any suitable representation may be used. In some embodiments, the output of sense hardware 114 is stored along with temporal information (e.g., a time stamp) to allow for later temporal correlation of the data.

Sensor 120 may be an eddy-current sensor, a dielectrometry sensor, an ultrasonic sensor, or utilize any other suitable sensing technology or combination of sensing technologies. In some embodiments, sensor 120 is an eddy-current sensor such as an MWM®, MWM-Rosette, or MWM-Array sensor available from JENTEK Sensors, Inc., Waltham, Mass. Sensor 120 may be a magnetic field sensor or sensor array such as a magnetoresistive sensor (e.g., MR-MWM-Array sensor available from JENTEK Sensors, Inc.), hall effect sensors, and the like. In another embodiment, sensor 120 is an interdigitated dielectrometry sensor or a segmented field dielectrometry sensor such as the IDED® sensors also available from JENTEK Sensors, Inc. Sensor 120 may have a single or multiple sensing and drive elements. Sensor 120 may be scanned across, mounted on, or embedded into test object 130.

In some embodiments, the computer-executable software modules may include a sensor data processing module, that when executed, estimates properties of the component under test. The sensor data processing module may utilize multi-dimensional precomputed databases that relate one or more frequency transimpedance measurements to properties of test object 130 to be estimated. The sensor data processing module may take the precomputed database and sensor data and, using a multivariate inverse method, estimate material properties. Though, the material properties may be estimated using any other analytical model, empirical model, database, look-up table, or other suitable technique or combination of techniques.

User interface 113 may include devices for interacting with a user. These devices may include, by way of example and not limitation, keypad, pointing device, camera, display, touch screen, audio input and audio output.

Network interface 119 may be any suitable combination of hardware and software configured to communicate over a network. For example, network interface 119 may be implemented as a network interface driver and a network interface card (NIC). The network interface driver may be configured to receive instructions from other components of instrument 110 to perform operations with the NIC. The NIC provides a wired and/or wireless connection to the network. The NIC is configured to generate and receive signals for communication over network. In some embodiments, instrument 110 is distributed among a plurality of networked computing devices. Each computing device may have a network interface for communicating with other the other computing devices forming instrument 110.

In some embodiments, multiple instruments 110 are used together as part of system 100. Such systems may communicate via their respective network interfaces. In some embodiments, some components are shared among the instruments. For example, a single computer may be used to control all instruments.

A fixture 140 may be used to position sensor 140 with respect to test object 130 and ensure suitable conformance of sensor 120 with test object 130. Fixture 140 may be a stationary fixture, manually controlled, motorized fixture, or a suitable combination thereof. For scanning applications where fixture 140 moves sensor 120 relative to test object 130, it is not critical whether sensor 120 or test object 130 is moved, or if both are moved to achieve the desired scan.

Fixture 140 may have one or more motors 141 that are controlled by motion controller 118. Motion controller 118 may control fixture 140 to move sensor 120 relative to test object 130 during an inspection procedure. Though, in some embodiments, relative motion between sensor 120 and test object 130 is controlled by the operator directly (e.g., by hand).

Regardless of whether motion is controlled by motion controller 118 or directly by the operator position encoders 143 of fixture 140 and motion recorder 116 may be used to record the relative positions of sensor 120 and test object 130. This position information may be recorded with impedance measurements obtained by impedance instrument 117 so that the impedance data may be spatially registered.

System 100 may be used to perform a method 200 for assessing a property of a test object, shown in FIG. 2.

At step 201 a precomputed database of sensor response signals is generated. The response signals generated may be predictions of the response signal 123 in FIG. 1 for a given excitation signal 121, sensor 120 and test object 103. Response signals may be generated for a variety of excitation signals, sensors/sense elements, and test objects, including variation in the position and orientation of the sensor and test objet. For example, the precomputed database may be generated for multiple excitation frequencies, multiple sensor geometries, multiple lift-offs, and multiple test object properties (e.g., geometric variations, electromagnetic property variations). The precomputed database may be generated using a model of the system, empirical data, or in any suitable way. In some embodiments the model is an analytical model, a semi-analytical model, or a numeric (e.g., finite element) model.

At step 203, sensor data is acquired. The sensor data may be acquired, for example, using instrument 110. Sensor data may be a recorded representation of the response signal 123, excitation signal 121, or some combination of the two (e.g., impedance). In some embodiments, sensor data is acquired at a plurality of excitation frequencies, multiple sensors (or sensing elements), and/or multiple sensor/test object positions/orientations (e.g., as would be the case during scanning).

At step 205, the sensor data is processed using the precomputed database generated at step 201. A multivariate inverse method may be used to process the sensor data with the At step 207, a property of the test object is assessed based on the processing of the measurement data at step 205. The property assessed may be an electromagnetic property, geometric property, state, conditions, or any other suitable type of property. Specific properties include, for example and not limitation, electrical conductivity, magnetic permeability, electrical permittivity, layer thickness, stress, temperature, damage, age, health, density, viscosity, cure state, embrittlement, wetness, and contamination. Step 207 may include a decision making where the estimated data is used to choose between a set of discrete outcomes. Examples include pass/fail decisions on the quality of a component, or the presence of flaws. Another example it may be determined whether the test object may be returned to service, repaired, replaced, scheduled for more or less frequent inspection, and the like. This may be implemented as a simple threshold applied to a particular estimated property, or as a more complex algorithm.

By performing step 201 prior to step 205 it may be possible that steps 203, 205 and 207 may be performed in real-time or near-real-time. Though, in some embodiments, step 201 may be performed after step 203 such as may be the case when database generation was not possible prior to the acquisition of measurement data, and perhaps further exacerbated by the fact that the test object may be no longer available for measurement.

Having described method 200 it should be appreciated that in some embodiments the order of the steps of method 200 may be varied, not all steps illustrated in FIG. 2 are performed, additional steps are performed, or method 200 is performed as some combination of the above. While method 200 was described in connection with system 100 shown in FIG. 1, it should be appreciated that method 200 may be performed with any suitable system.

Section B: Detail of Sensor
Sensor Footprint Model and Application
Motivation

Figure 4:
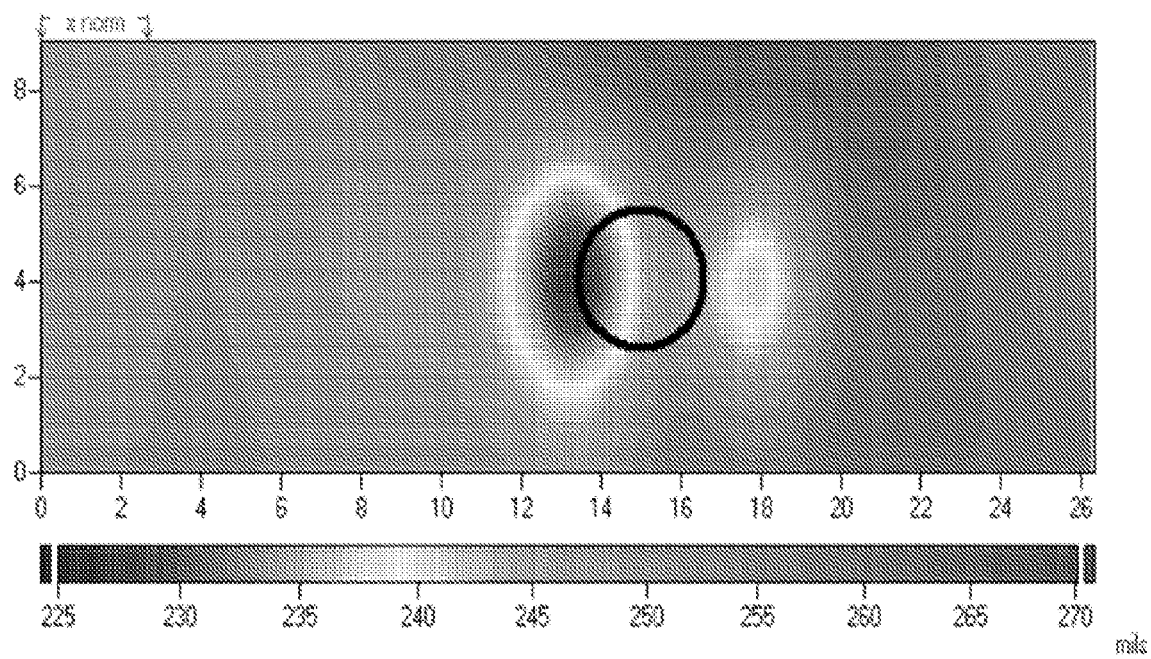
Figure 25:
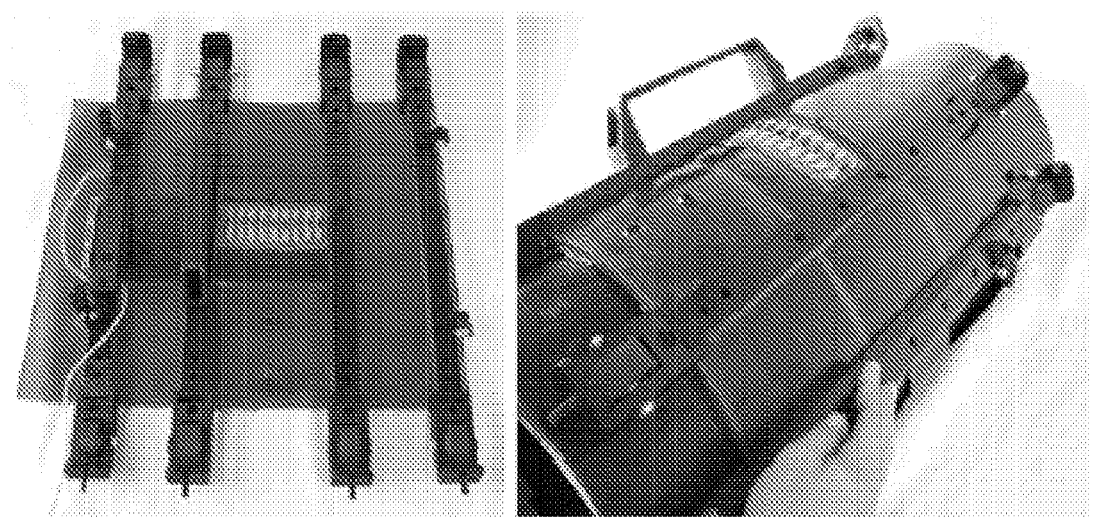

After testing an initial prototype MR-MWM Array sensor pictured in FIG. 25 on flat steel plates with manufactured defects at 2" of lift-off, it became immediately obvious that the issue of detecting localized defects had not been solved. FIG. 4 displays the result that motivated the following model derivation.

The flat plate that was scanned had a 0.150" deep, 3" diameter defect etched into a 0.250" inch steel plate. The sensor that was used had a single rectangular drive whose conductors were 4.5" apart, center-center. The sense elements were 1.5" away from one of the conductors. This type of drive construct is very common in applications for eddy current sensors, specifically MWM-Arrays, and it seemed like a reasonable place to start.

The dark circle represents the expected location of the response when the sense element array was centered over the flaw. Instead, the single uniform flaw created two responses, the largest of which was only 0.025" deep, considerably less than the 0.150" flaw depth. Based on the spacing of the two responses, it seems that the two peaks occurred when each of the drive conductors were centered over the flaw. Overall, the result showed that the reported size and depth were not representative of the defect, and that general sensitivity to local defects was low.

Conjecturing that the sensor's flaw response is a function of the volume of a flaw, if this flaw provided a 0.025" response, then we could extrapolate that the desired 0.050" deep, 2" diameter defect would only provide a 0.0037" response. While this may be at the very edge of the sensor's capability, it was clear that designing a sensor with a higher sensitivity to local defects was required to reliably meet or surpass the goal of detecting 2 inch diameter 20% wall loss defects.

Based on this observation, it was hypothesized that the flaw response could be resolved into a single peak with a larger magnitude by using a single drive wire that wrapped around the entire circumference of the pipeline (taking advantage of the cylindrical geometry of the target application). This was a promising idea which turned out to be very difficult to manufacture because of the requirement to solder the 80 individual wires in a specified pattern at the seam. A prototype was built, and it is displayed in FIG. 5.

Unfortunately, while the response did not display two distinct peaks like the response of the initial prototype sensor, the response was much wider than expected and of a much lower magnitude. And, the sensor was much more sensitive to the ends of the pipe, over a much larger distance. This result makes sense if we think of the sensor as providing an average thickness response over its sensor "footprint." By moving from the single rectangular sensor with two conductors, to a single conductor wrapped around the circumference of the pipe, we made the sensor footprint much larger. This was the opposite of the desired effect.

Therefore, it was clear based on these experiments that a model was needed to predict the footprint of a sensor given different drive constructs. The following describes Methods AAA, BBB, and CCC for modeling an eddy current sensor's footprint when interacting with a test object. It discusses their relative successes and shortcomings, and shows how the models helped to design a much more effective MR-MWM-Array for the CUI application and could be applied to other eddy current sensor designs.

Method AAA: 1-D Perfect Electrical Conductor (PEC) Footprint Model

Method AAA was for the purpose of gaining some rough intuition of the footprint effect. It is a very simple 1-D model. The assumptions were as follows:

The test object is a perfect electrical conductor (PEC), with $\sigma = \infty$.

The drive conductors are infinitely long and infinitely thin wires parallel to the test object at a height h from the test object.

The sense element is in the same plane as the drive conductors, also at a height h and considered to be infinitely long in the direction parallel to the drive.

FIG. 7 (top) shows the analyzed structure for the case of a single drive wire. The advantages of these assumptions are immediately evident. The magnetic fields due to infinitely long wires above a PEC are easily calculated using image theory. And the principle of superposition can be used to calculate the field for each drive wire independently with the entire sensor's response being the sum of the responses for the individual drive wires.

The following analysis provides a first-order approximate representation of the sensor response to the test object as a function of position on the material. Assuming the test object is a PEC ignores magnetic diffusion and frequency related effects; assuming that the drive is constructed of infinitely thin line currents ignores the effect of winding thickness. Furthermore, since everything is considered infinite in the direction of the drive conductors, this formulation only analyzes the footprint in the direction orthogonal to the drive conductors. Despite being so simplified, this model was very predictive of a given sensor-geometry's response to localized defects and was a good first iteration for developing intuition on a given sensor-geometry's measurement footprint.

There are two analysis steps associated with this model. The first step is a calculation of the nominal current distribution flowing along the surface of the test material. The second step is to relate the local surface current density to the field that would be generated in the vicinity of a sense element. This is used to determine the sense element response to a local feature (i.e., material loss that leads to a reduction in the surface current) anywhere in the vicinity of the drive winding and provides the sensor response footprint.

The basic geometry for a single wire is shown in FIG. 7 (top). It is assumed that the drive winding carries a current I out of the page (in the $\hat{z}$ direction) and is located at an x position of w and a y position of h. The sense element is also located at a height h above the surface of the test material.

Assuming that the test material is a PEC, the test material can be replaced with an image current source (this is equivalent to assuming that the excitation frequency is relatively high compared to the eddy current skin depth in the test material). This allows the magnetic field above the test material to be determined, which, in turn, allows the induced eddy current surface distribution in the test material to be determined. Using the equivalent source geometry of FIG. 7 (bottom), the magnetic field intensity just above the surface of the test material can be obtained from the Biot-Savart law as $$H(x) = \frac{I}{\pi} \frac{h}{h^2 + (x-w)^2} \hat{x} \tag{4.1}$$

The current flowing through the surface of the test material is then determined from the boundary condition that requires the tangential component of the field intensity $H_x$ to be zero inside the test material. This surface current density can be expressed as $$K(x) = \hat{y} \times H_x \hat{x} = -\frac{I}{\pi} \frac{h}{h^2 + (x-w)^2} \hat{z} \tag{4.2}$$

The second step is to project this local current density back to the location of the sense element so that the field that would be measured by the sense element can be determined. In air, without a test material present, the field intensity in the vicinity of the sense element is $$H_{air}(x) = -\frac{I}{2\pi w} \hat{y} \tag{4.3}$$

This field is perturbed from the air response by the presence of the test material. Using the same Biot-Savart law given above, the perturbation in the field around the sense element due to the induced surface current is $$dH(x) = \frac{I\Delta x}{2\pi^2} \left[ \frac{h}{h^2 + (x-w)^2} \right] \left[ \frac{-h\hat{x} + x\hat{y}}{h^2 + x^2} \right] \tag{4.4}$$

where $\Delta x$ is the incremental spacing in the $\hat{x}$ direction. The first term in brackets comes from the imposed field while the second term comes from the projection of the surface current back to the sense element. This formulation provides both components of the magnetic field at the sense element. In general, the MR-MWM-Array is only sensitive to the normal component ($\hat{y}$ component) of the magnetic field. This is because there is no tangential component of the field when measuring in air, which makes an air calibration of this component more difficult. It would be accurate to classify the tangential component sensor as a differential sensor with respect to the test object.

Figure 8:
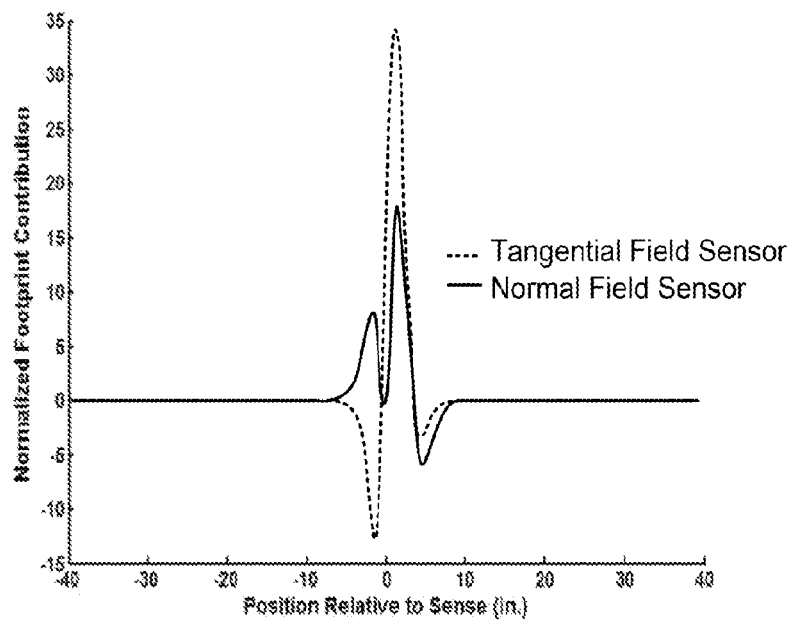

One very interesting product of this analysis was proving that the different components of the magnetic field have very different footprints. For example, as shown in FIG. 8, a sensor detecting the component of the field tangential to the material would have a larger peak response to a local defect with different shaped sidelobes. The potential advantages of these two factors will be discussed in the following section on sensor optimization. Sensing the tangential field would also reduce the sensor's response to air, allowing the sensor to be driven with more current without saturating the sensor's response. As mentioned above, a different calibration routine would be necessary for the tangential sensor.

The tangential sensor footprints are also examined in Method's BBB and CCC although their results are not discussed.

Figure 5:
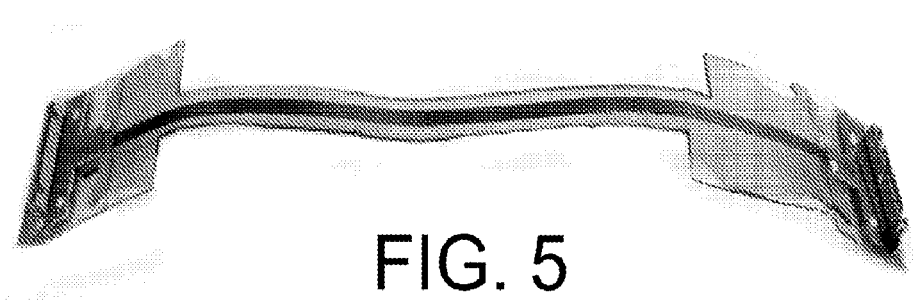
Figure 9:
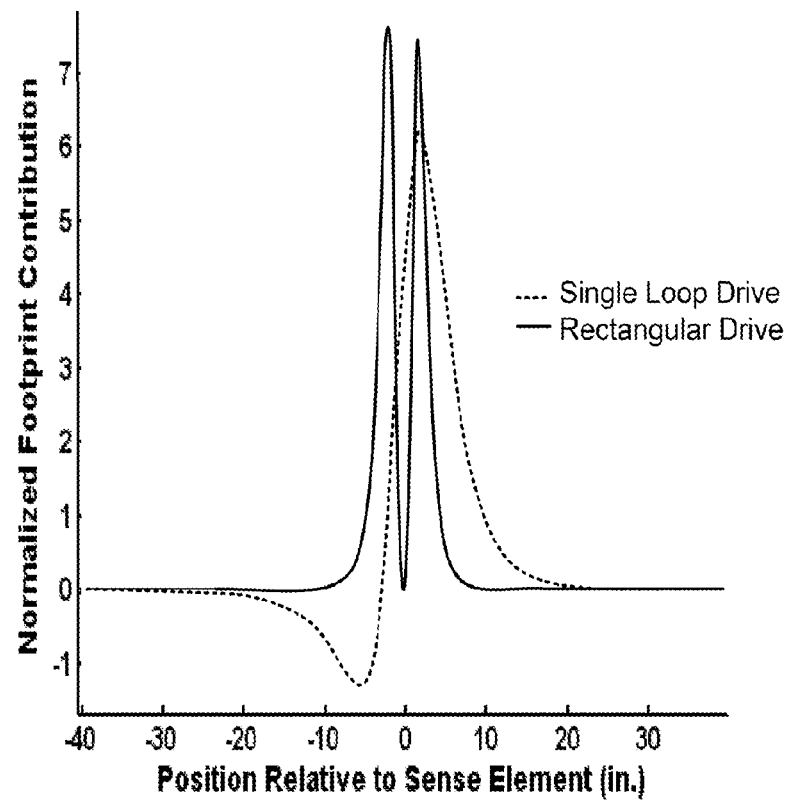

Calculating the footprints of the single loop drive pictured in FIG. 5 and a the rectangular drive shown in FIG. 25 demonstrates the validity of this approach. These footprints are very representative of the measurements taken and are shown in FIG. 9. The footprints are normalized by the area under the footprint curve to show the relative sensitivity to the material as a function of position. Despite the simplicity of the analysis, the footprint of the rectangular drive predicts the two response peaks at 4.5" apart. Furthermore the footprint model predicts a wider, single peak for the single loop drive.

Because of the initial success of the 1-D PEC analysis, the model was extended to take into consideration the finite length of the drive and sense elements as well as drive wires of finite thickness. This results in a calculation of a 2-D PEC footprint which can be used to provide initial predictions in sensor sensitivity. This model is derived in the following.

Method BBB: 2-D PEC Footprint Model

The basic approach for the 2-D PEC footprint model, Method BBB, is the same as the 1-D PEC footprint model: first determine the current density induced on the surface of the PEC and then reflect that back to the magnetic field at the location of the sense element. The main difference is that instead of an infinitely long and thin current wire over the PEC, we have a discrete current volume, representing a finite wire with width and length.

Figure 6:
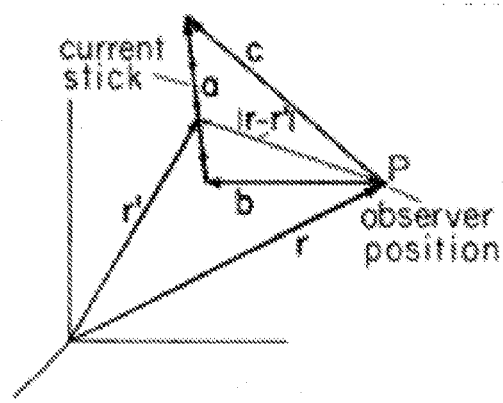

This problem can be formulated conveniently by the "current stick model" [H. Haus, J. Melcher, Electromagnetic Fields and Energy, Prentice-Hall Inc., New Jersey, 1989.]. The geometry for this model is shown in FIG. 6. The model uses the Biot-Savart law to derive:

$$H(r) = \frac{j}{4\pi} \frac{c \times a}{|c \times a|^2} \left( \frac{a \cdot c}{|c|} - \frac{a \cdot b}{|c|} \right) \quad (4.5)$$

The current volume can then be approximated as an integral, or more conveniently implemented in Matlab as a Riemann-Sum, where each sub-volume's current is considered to concentrated in a current-stick at the sub-volume's center. Therefore, as in the 1-D case, we can then use image theory to calculate the induced surface current density on the surface of the PEC and reflect it back to the magnetic field at the sense element. The result is a two-dimensional representation of the sensor footprint.

Figure 11:
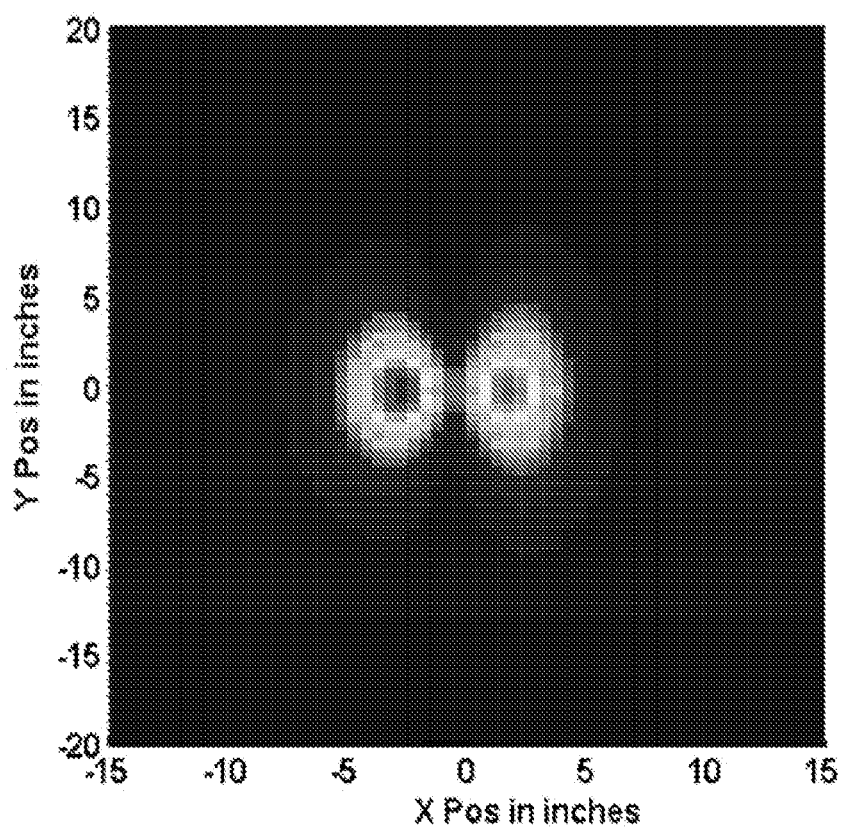

FIG. 10 shows the 2-D PEC model footprint for the sensor pictured in FIG. 25. FIG. 11 then shows the result when the footprint is convolved with a flaw representative of the one scanned in FIG. 4. The results are very encouraging. The 2-D footprint model captures the double peak shape of the response as well as the first peak being slightly larger than the second. The relative position of the two peaks is also accurate: the spacing between them is approximately 4.5", which is the distance between the center of the two legs of the drive. Also, the larger of the two responses corresponds to when the drive leg that is closer to the sense element passes over the flaw for both the model and the measurements. And finally, the footprint model accurately predicts the large blurring in the direction parallel to the drive.

There are two shortcomings of the 2-D PEC model. The first problem is that the predicted size of the response is approximately 20% high—the model predicts a maximal sensor response of 0.030", when the sensor response is actually only 0.025". This bias in predicted size holds for other flaw sizes as well.

The second shortcoming is more serious. The PEC footprint model provides only a magnitude response (as there is no phase information from a PEC) and, therefore, expects all perturbations to behave similarly. This assumption is not valid. When looking at a near side flaw in steel, the thickness response and the lift-off response are not equivalent. The thickness response seems to be centered around the location of the drive conductors while the lift-off response seems to be more centered around the location of the sense element.

It is likely that this behavior is not captured because the PEC model ignores diffusion. A footprint model that relaxes the PEC requirement to capture frequency dependent and material dependent diffusion effects will be discussed in the Method CCC. This model will also be appropriate for cylindrical coordinates.

Method CCC: Cylindrical Coordinate Footprint Model Incorporating Diffusion Effects In order to create a footprint model that takes into consideration frequency and material properties and the associated diffusion effects, we need to determine a method for figuring out the current density in the test object. When the test object is not a PEC, the method of image currents is not available to us.

Method CCC accomplishes this with a clever application of the Love's Field Equivalence Principle [S. R. Rengarajan and Y. Rahmat-Samii, "The Field Equivalence Principle: Ilustration of the Establishment of the Non-Intuitive Null fields," IEEE Antennas and Propagation Magazine, Vol. 43, No. 4, August 2000]. The procedure for calculating the footprint is as follows:

Use an eddy current sensor model, potentially from Method XXX, to determine the magnetic field everywhere in the presence of the test object.

Use an eddy current sensor model, potentially from Method XXX, to determine the magnetic field everywhere in air (in the absence of a test object).

Subtract the air response from the total response to use the Superposition Principle, and determine the field everywhere due to the induced eddy currents in the test object.

Use Love's Field Equivalence Principle, described by the geometry in FIG. 12, to represent the unknown induced eddy currents in the test object as a surface current around free space, Reflect that surface current back to the sense element to determine the impedance response footprint of the sensor.

There are a few things to discuss about the assumptions of this model. First, while it does handle the layered media model, it only approximates the footprint at the surface of the outermost layer of the test object. For the case of CUI for example, one could argue that this is not appropriate as the outermost layer is the weatherjacket. However, the presence of the weatherjacket only provides a phase shift at the low frequencies that are sensitive to the thickness of steel. The weatherjacket does not change the relative sensitivity level. So, ignoring its presence for the case of the footprint analysis is not a bad assumption.

Secondly, converting the footprint information into an expected flaw response is more complicated than in the PEC model. In the PEC model, since only a magnitude footprint was calculated, this was convolved with a flaw response that was represented as a thickness change. Now, the footprint convolution must be done in impedance space and then converted back into properties of interest. This allows for a separate footprint for each measured property.

Figure 13:
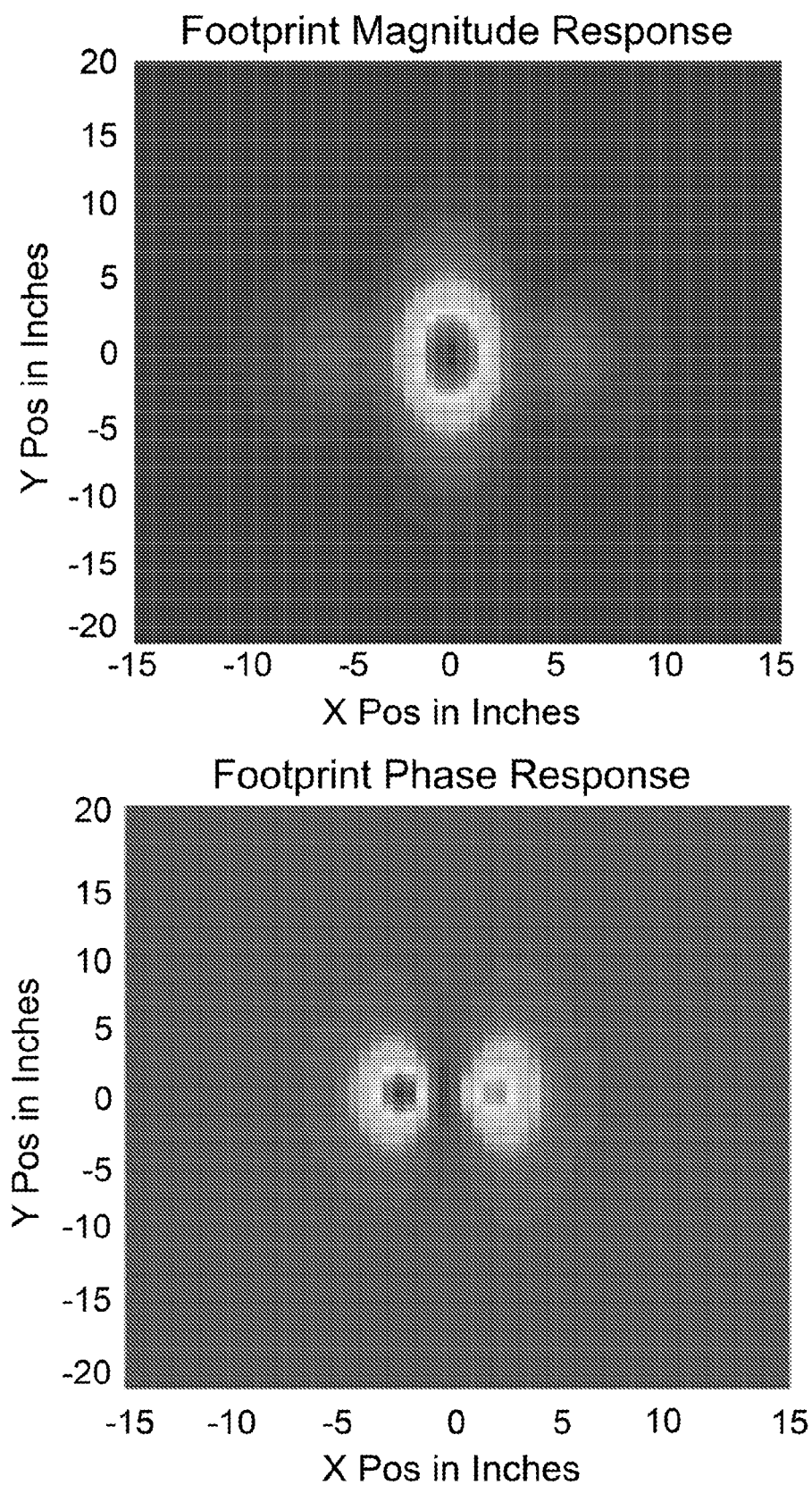

The magnitude and phase footprint of the sensor pictured in FIG. 25 at 10 Hz is shown in FIG. 13 for the flat plate configuration. The phase footprint is very similar to the footprint calculated by the PEC model, as expected: the thickness response at 10 Hz is mostly in phase, and the PEC model was predictive of the sensor's thickness response. The phase footprint is slightly wider than the PEC calculated footprint causing the predicted thickness response to the flaw scanned in FIG. 4 to drop from 0.030" predicted by the PEC model to 0.024". Therefore, incorporating diffusion into the model eliminated the upward bias in predicted thickness response discussed in the Method BBB.

Furthermore, the magnitude of the footprint response is centered under the sense element and only has a single peak. This corresponds to the lift-off response of the sensor, resolving the second shortcoming of the 2-D PEC model discussed in Method BBB.

Sensor Design Optimization

The main motivation for developing the footprint models was to gain intuition as to how changes in the sensor geometry affected the sensor's sensitivity to local defects. The desired ideal footprint would be a 2-D delta function: this would cause each measurement to be a perfect sample of the material directly under the sensor.

Figure 14:
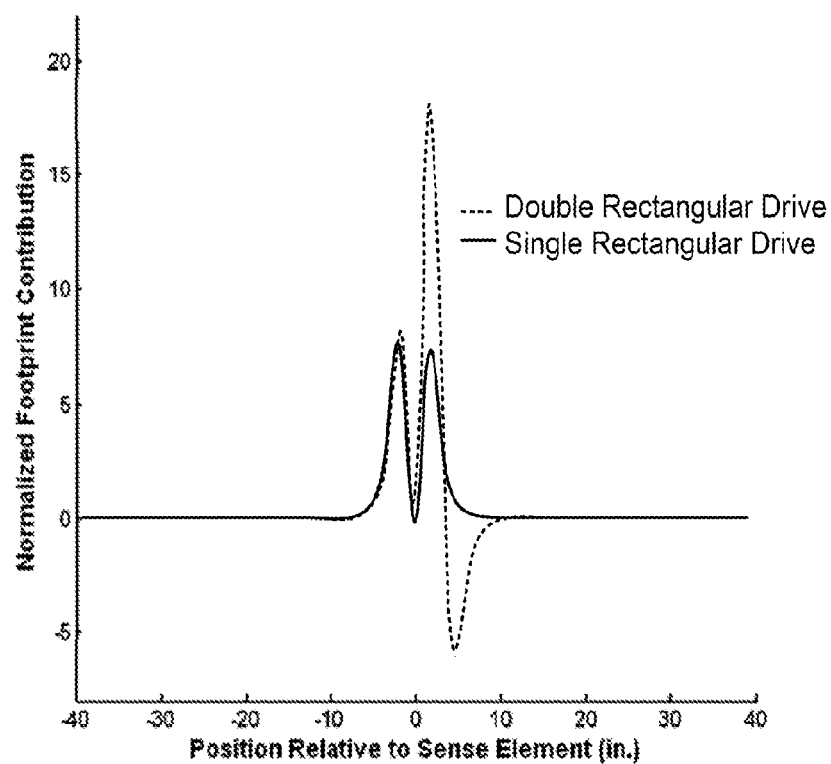

The placement of the conductors allows for the manipulation of the footprint perpendicular to the drive conductors. After trying many different drive configurations, the design converged on a double rectangular drive structure with the sense elements centered in one of the rectangles. The width of the rectangle was chosen to be 3.5" in order to achieve a similar sensitivity to steel thickness as the single rectangular sensor used in previous measurements. FIG. 14 shows the improvement of the sensor footprint. The main peak of the double rectangular footprint is over twice as tall as the taller peak of the single rectangular footprint, which indicates improved sensitivity to local perturbations.

It should be noted that while a large, narrow peak for the sensor footprint is desired, it should not be achieved at the cost of creating a differential sensor. In other words, the integral of the sensor footprint must not be close to zero. If this were the case, calibration in air would be impossible.

Figure 15:
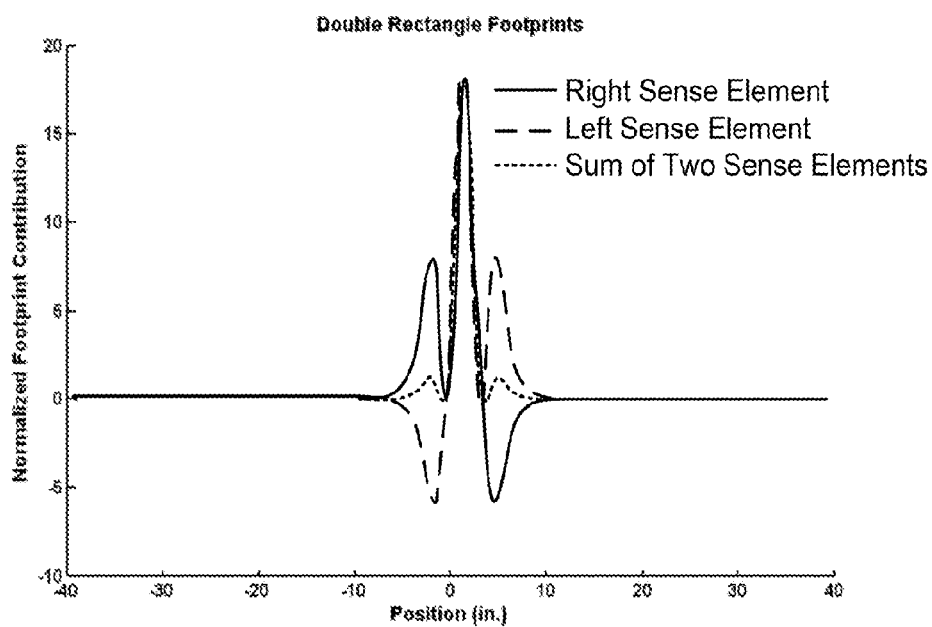

The double rectangular sensor has other desirable characteristics. First, there is only one side lobe on either side of the main lobe, and the lobes decay to zero quickly as compared to other designs. Another thing to notice is that the side lobes are anti-symmetric. That is, moving the sense elements into the other drive rectangle causes the side lobes to flip. By creating a sense element that is the combination of two sense elements, one in either rectangle, we are left with an even more ideal footprint. This is shown in FIG. 15. The combined sense element sensor has the advantage of the large peak without the large side lobes.

The benefit of having the side lobes cancel is very significant. In addition to eliminating secondary peaks in the response as seen with the single rectangular sensor, the combined sense element sensor also greatly reduces unmodeled behavior. The model assumes that the test object is a uniformly layered material: under this assumption the side lobes would cancel. Using a single sense element requires material on one side of the sensor to cancel with material on the other side of the sensor. If the material is varying, this does not happen, and the property estimates would be corrupted by the unmodeled behavior. However, combining the two sense elements cancels out the side lobes using the same material twice. Therefore, even if the material is varying from one side of the sensor to the other, the measurements will more closely adhere to the model.

Figure 16:
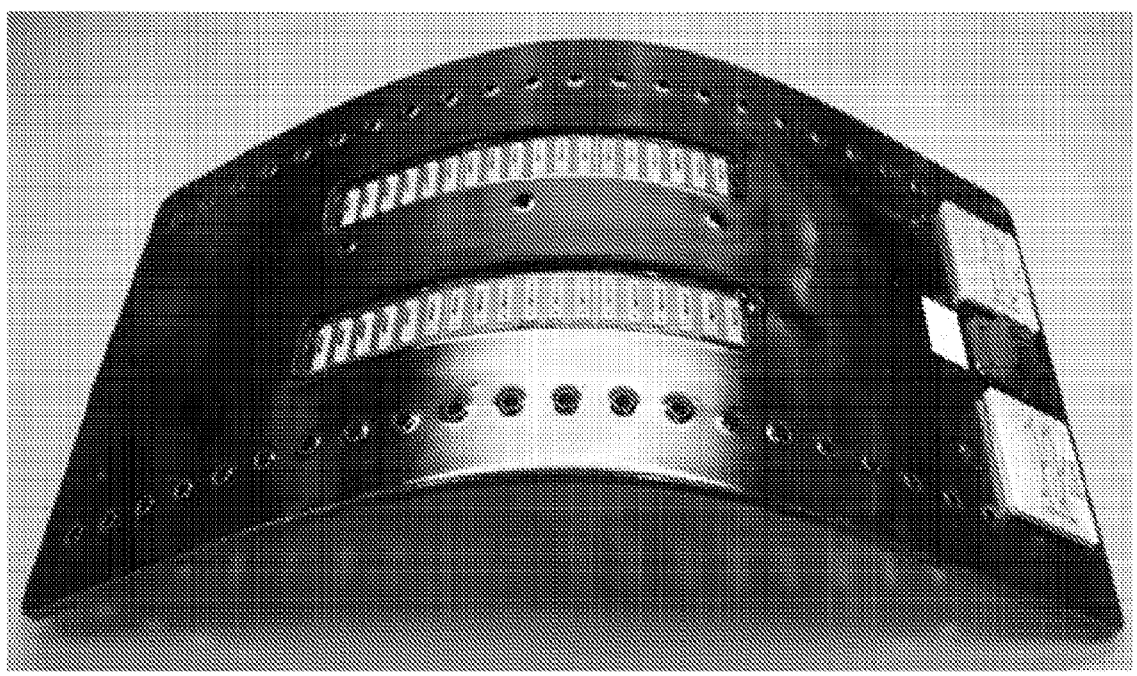
Figure 17:
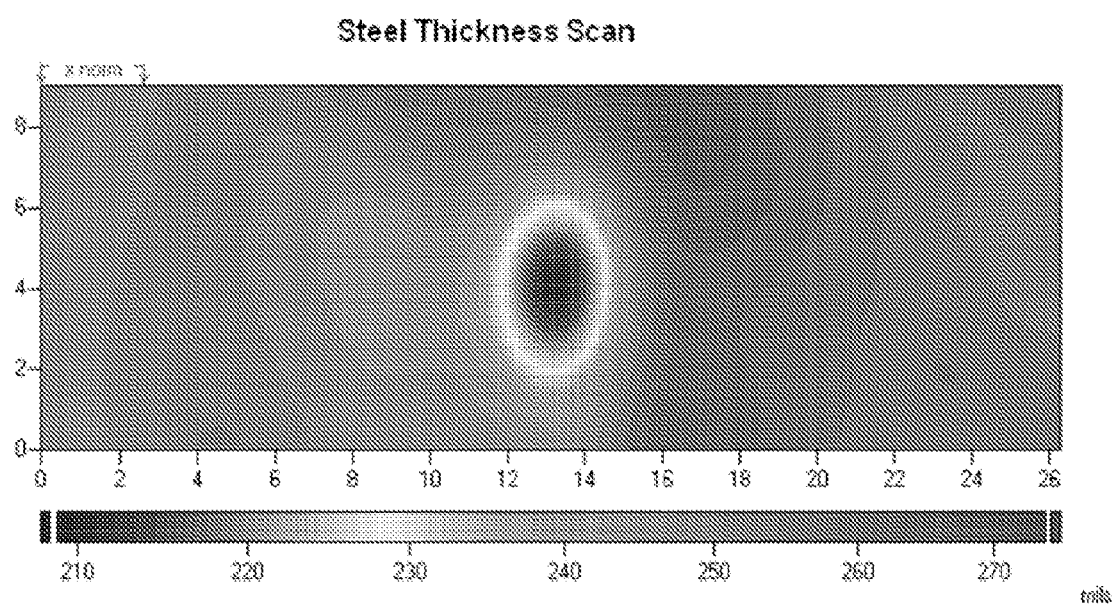

FIG. 16 shows a flexible double row, double rectangular MR-MWM-Array. The drive is not visible because it was potted in an opaque polyurethane. FIG. 17 shows the improvement in response when scanning this sensor over the same 0.25" flat plate with a 0.150" deep, 3" diameter defect at 2" of lift-off scanned in FIG. 4. The signal shape is much more representative and the response is 0.041" as compared to the previous response of 0.025". The improvement provides the required SNR to detect the target 2 inch diameter, 0.050" flaw.

The double-row sensor can be implemented without requiring twice as many channels by placing the elements in series (in the case of a inductive sense element) or by using an adder stage (in the case of an active sense element like the MR element). Having the independent information from both sensors, though, can provide information beyond simply adding the two results together. So doubling the channel count may be beneficial In the case of an active element, such as the MR sensor, that is sensitive to DC fields, the double row sensor has another large benefit. The two rows can be used to cancel unmodeled effects due to motion through a spatially varying DC fields. These spatially varying DC fields can be due to the Earth's magnetic field, perturbations of Earth's magnetic field due to magnetic objects such as steel objects, and other local magnetic fields. These unmodeled effects become more significant the larger the spatial variation and the faster the sensor is moving through them.

Sensor Manufacture

Normal (absolute) and tangential (differential) fields have different footprint (SD)

Figure 18:
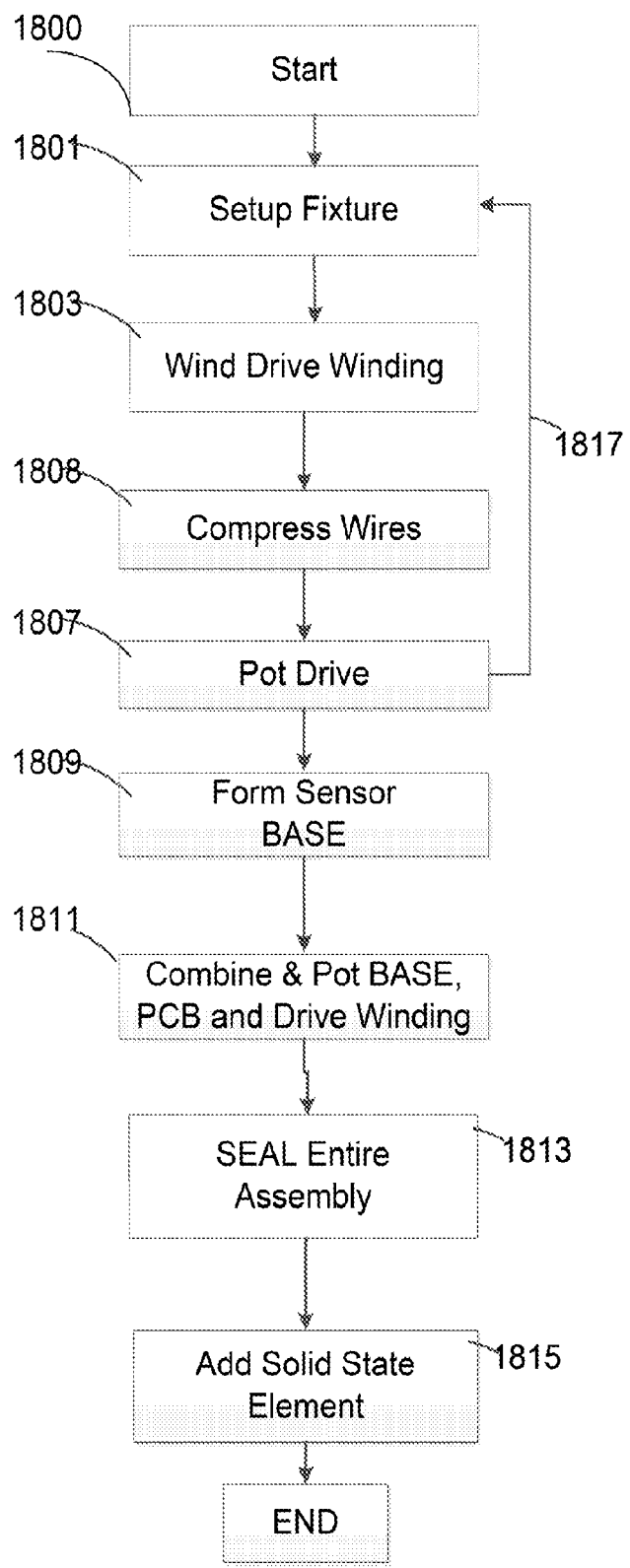

FIG. 18 shows a method of constructing a sensor.

At step 1801, the winding fixture is set up based on the length and width of the drive. The width of the drive is determined by the desired spatial wavelength of the sensor. The spatial wavelength is determined based on the intended application and may include such factors as the desired sensor liftoff and the thickness of the materials under test. The drive length is determined by the length of the sense element array, the spatial wavelength, the expected liftoff, and the electromagnetic properties of the material under test.

At step 1803, the drive winding is wound using an insulated wire. Individual turns of the drive winding are placed together, either by hand or in a jig, such that the outer wires of each drive are in contact with the wires of the adjacent turns. The wire may have an enamel coating to provide electrical isolation between adjacent windings. The cross section of the wire may be round, flat (i.e., rectangular), or any other suitable cross section. In some embodiments, the drive winding is wound with each wire laterally adjacent to the next. The tension on the wire may be controlled to ensure that the winding doesn't lose tension or otherwise deform. Control may be achieved by hand or using a using a spool tensioner. The tension on the wire may vary based on the sensor requirements. The number of turns in the drive winding is controlled by the sensor specification.

At step 1808, the wires are compressed to a pre-determined thickness so that each drive has an identical winding thickness.

At step 1807, the drives are potted using a suitable potting compound. For example, a flexible urethane rubber. The mold has alignment features so that the drives can be accurately positioned later in the assembly process. For example, posts can be added to the mold that produce holes in the rubber that can be placed onto alignment posts later in the assembly process. After the rubber has cured, the drive is removed and trimmed. For sensors with multiple drive windings, multiple windings are produced.

At step 1809 a thin bottom layer is applied to the bottom of the jig. This bottom layer can be pre-cut material or cast using a suitable potting compound (such as urethane rubber). For urethane rubber, the layer is allowed to partially cure. A partial cure allows subsequent layers to fully adhere to the bottom layer while allowing the bottom layer to have some stiffness.

At step 1811, a flexible PCB is placed on top of this bottom layer. The PCB has alignment features (similar to the drive winding) that allow it to be aligned relative to the rest of the assembly. The drive winding or windings are placed on top of the PCB using the same or other alignment features. The windings can be touching or separated by a fixed gap. A thin coating of urethane rubber is used between each layer to ensure that they adhere to each other. Strain on the PCB is reduced by placing the flexible PCB as close to the neutral bending plane of the sensor as possible.

At step 1813 rubber is poured over the assembly and allowed to cure.

At step 1815 MR sensors and connectors are soldered to the PCB.

Section C: Instrument

The inventors have recognized and appreciated the need for impedance instrument 117 to provide high data rates, good signal-to-noise levels, wide bandwidth frequency operation (including low-frequencies approaching DC), and colocation in time and space of impedance measurements.

Figure 19A:
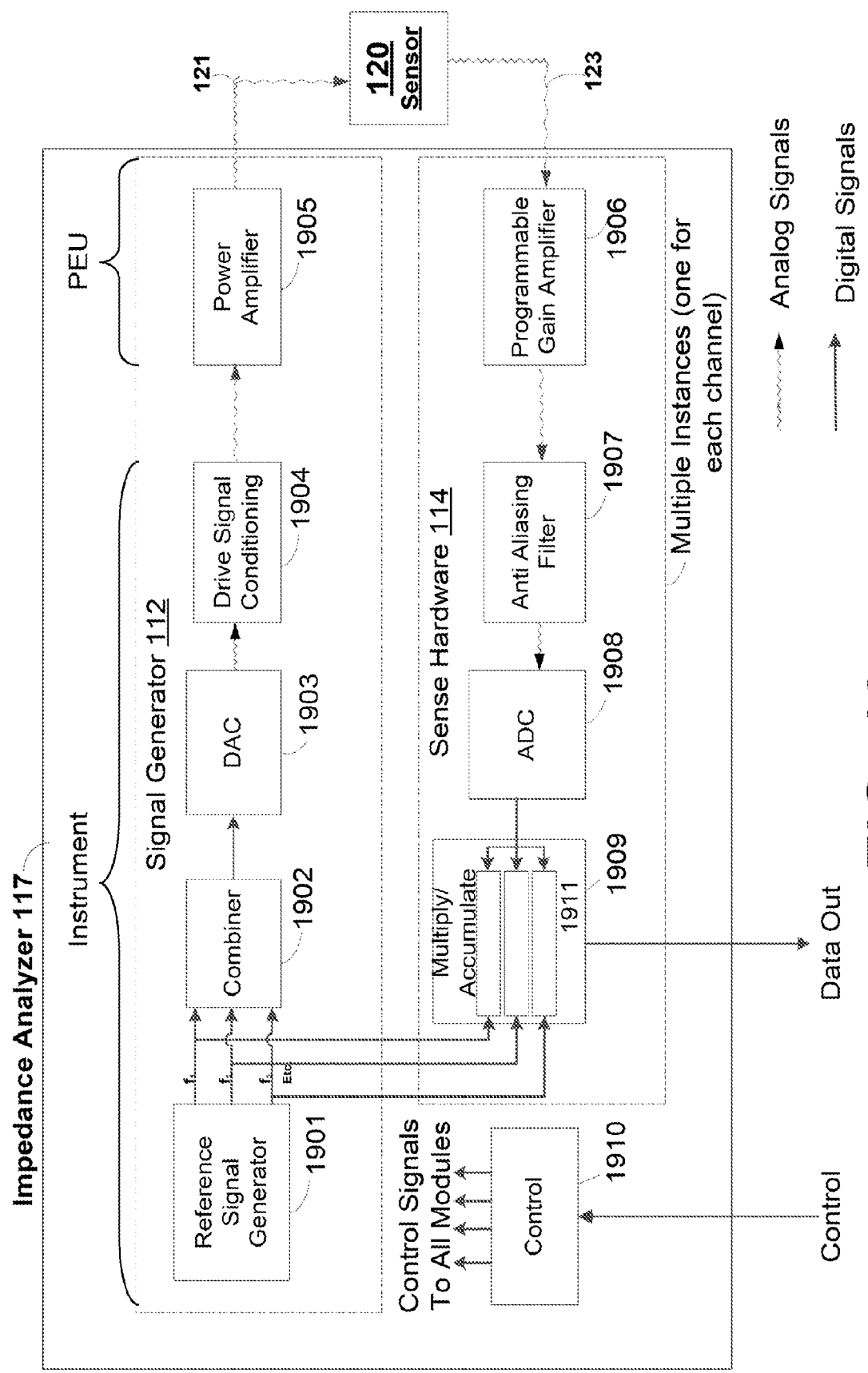

An embodiment of impedance analyzer 117 that achieves all of these objectives is presented with reference to FIG. 19A. Impedance analyzer 117 includes signal generator 112, sensing hardware 114, and control hardware 1910. Subcomponents of signal generator 112 may include reference signal generator 1901, combiner 1902, digital-to-analog converter (DAC) 1903, signal conditioner 1904, and power amplifier 1905. Subcomponents of sense hardware 114 may include programmable gain amplifier 1906, anti-aliasing filter 1907, analog-to-digital converter (ADC) 1908 and multiply/accumulate block 1909.

Signal generator 1901, combiner 1902, multiply/accumulate block 1909, and control hardware 1910 are implemented in field-programmable gate arrays (FPGA). In one embodiment all subcomponents are implemented within the same FPGA, though multiple FPGAs may also be used. A microprocessor based implementation of the digital components is also possible, though currently impractical at the required data rates. An embodiment of impedance analyzer 117 incorporates application-specific integrated circuits (ASICs), i.e., custom integrated circuits to carry out the function of some or all components and subcomponents. It should be appreciated that any suitable approach may be used.

The components and subcomponents of impedance analyzer 117 may be physically located in a single "box" or separated in any suitable way. In some embodiments, the components are divided into an "Instrument" and a "Probe Electronics Unit" (PEU), as indicated in FIG. 19A. In other embodiments all components are housed in a single common enclosure, reducing complexity, cost, and power consumption. Though it should be appreciated that other configurations may also be used. Some embodiments use a modular PEU design where a certain number of programmable gain amplifier 1906 are housed in a single unit and power amplifier 1905 is housed separately. This allows the number of channels and drives supported to be customized to a specific application by combining varying numbers of such PEU submodules.

Reference signal generator 1901 generates the signals, in digital form, that are used both to create excitation signal 121 ultimately applied to sensor 120 and as reference input to multiply/accumulate block 1909. The outputs of reference signal generator 1901 may include the in-phase and quadrature waveforms at one or more frequencies. The quadrature reference signal is a version of the in-phase reference signal shifted one-quarter period (i.e., 90 degrees). The in-phase signals are provided to both combiner 1902 and multiply/accumulate block 1909; the quadrature signals are provided to multiply/accumulate block 1909. These signals are synchronized, which allows for the fully parallel measurement of the real and imaginary components at all frequencies. Note that reference signal generator 801 may also be used to create other waveforms, e.g. ramps, in addition to sinusoidal signals. Reference signal generator 1901 may be implemented as a look-up table, i.e., where the output data is read from memory, as a real-time frequency generator that uses an algorithm to generate the data, or in any suitable way.

In some embodiments of reference signal generator 1909 all frequency generators may be clocked at the same clock frequency. The measurement frequencies are chosen such that the clock frequency, $f_c$, is an exact integer multiple of the measurement frequency, $f_m$. That is $f_x = n \times f_m$, where n is an integer. This results in all periods having the same number of samples per period, located at the same relative time positions. This is critically important to the ability to take accurate measurements at high data rates, as it allows the multiply/accumulate block 1909 to completely eliminate contamination from unwanted harmonic frequencies using only a single half-period of data. Though, measurement frequencies may also be used that are related to the clock frequency as integral fractions, i.e., $k \times f_c = n \times f_m$ where k and n are integers and k is a small number, in which case at least k periods would be needed per measurement. The number n may be chosen to be a power of 2 (2, 4, 8, 16 . . . ) because this significantly simplifies the hardware implementation of block 809, transforming needed division operations into simple bit shift operations.

The accuracy (i.e., number of bits) of the digital representation of the signals, both in the signal generator 112 and sensing hardware 114, is chosen such that the magnitude of the resulting quantization error is smaller than that of the minimum instrumentation noise due to the analog electronics. Some example embodiments use 16-bit accuracy, though other embodiments that use 14 bits have reduced power consumption with no loss of accuracy.

Combiner 1902 sums all the signals received from reference signal generator 1901. For example, combiner 1902 may combine signals of different frequencies. Combiner 1902 may apply different weights to the different signals in the summation. Weights may be chosen to improve the signal-to-noise ratios of the measurements at each frequency. If only one signal is provided by reference signal generator 1901, combiner 1902 may simply act as a pass through, or may scale the signal. If multiple frequencies are combined, an individual frequency's signal magnitude is less than what it would be if used alone, because the same output magnitude limit applies in both cases. Lower signal magnitude at a specific frequency can result in lower signal-to-noise ratio. In such cases it may be beneficial to carry out multiple frequencies sequentially. In some embodiments, combiner 802 may additionally apply phase shifts to the component signals.

The output signal of combiner 1902 is converted to analog form by DAC 1903.

Analog signals are represented by zig-zag lines in FIG. 19A, while digital signals are represented by simples lines.

The analog output of DAC 1903 is provided to drive signal conditioning module 1904. Module 1904 may include an anti-aliasing filter and a programmable attenuator stage.

The anti-aliasing filter is a low-pass filter that prevents aliasing by eliminating frequencies above one half of the sampling frequency. In some embodiments, the filter features multiple—feedback active filter stages and passive RLC stages. Though, any suitable filter design may be used.

The programmable attenuator stage is necessary to provide the sensor with the most appropriate drive level without reducing the magnitude of the DAC output, which would reduce accuracy. The programmable attenuation is controlled by the software. In one embodiment, the programmable attenuation stage is implemented as a sequence of multiple fixed-attenuation stages that may be selectively bypassed. In another implementation variable gain is achieved by selecting from multiple taps in a resistor divider ladder network. The multi-stage programmable attenuation architecture has significant advantages over traditional variable-gain amplifier (VGA) based implementations. These include much lower thermal drift (gain changing with temperature) and noise.

The conditioned signal is provided from module 1904 to power amplifier 1905 which uses it to generate excitation signal 121 applied to sensor 120. Power amplifier 1905 supplies excitation signal 121 with sufficient current as dictated by the sensor and application requirements. While sensor 120 is illustrated in this embodiment, it should be appreciated the any suitable device may be connected to impedance analyzer 117. For example, a device having two or more ports may be connected to impedance analyzer 117.

The impedance analyzer may have multiple signal generators 112, supplying excitation signals to more than one drive winding within the same sensor or device, or to multiple sensors/devices. The separate signal generators may operate at the same frequency or at different frequencies.

Sense hardware 114 receives response signal 123 from sensor 120. While only one response signal 123 is shown in FIG. 19A, it should be appreciated that sensor 120 may have more than one sensor output. In such case, sense hardware 114 may be multiplexed, may be replicated such that sense hardware 114 contains multiple channel paths, each comprised of blocks 1906, 1907, 1908, and 1909, or both multiplexing and parallel channel paths may be used. The channel paths may be identical, but may be adjusted for the respective response signal. For example, programmable-gain amplifier 1906 may have different setting in different channel paths.

Programmable-gain amplifier 1906 of sense hardware 114 receives response signal 123. Qualitatively, response signal 123 may be a very low-level signal—amplifier 1906 therefore provides amplification which allows conversion to digital form with improved resolution and low noise. The amplification factor (gain) is controlled by the software to select the most appropriate signal level to reach ADC 1908. Every channel can have a different gain setting. The highest signal-to-noise ratios are achieved when the signal magnitude at the input of the ADC is at the highest possible level without exceeding the maximum input level. Though, a safety margin, 20% in one embodiment, is used to reduce the risk of accidentally exceeding the maximum ADC input level. Programmable gain amplifier 1906 may be implemented as a sequence of fixed-gain stages, with digitally controlled switches controlling whether each stage is used or bypassed. The total gain of the programmable gain amplifier is the product of the gains of the individual non-bypassed stages. The individual stage gains are chosen such that an adequately wide range of total gain values can be achieved, with an adequate number of possible intermediate gain values. In one embodiment, the gains of the fixed-gain stages form a doubly-exponential sequence, e.g., $g$, $g^2$, $g^4$, $g^8$, $g^{16}$ . . . , resulting in possible gain values distributed evenly on a logarithmic scale. The multi-stage programmable gain architecture has significant advantages over traditional variable-gain amplifier (VGA) based implementations. These include much lower thermal drift (gain changing with temperature) and noise.

As noted above, in some embodiments, power amplifier 1905 and variable-gain amplifier 1906 are located in a probe electronics unit which may be physically closer to sensor 120 than the remaining components of impedance analyzer 117. Locating these components close to sensor 120 may improve signal-to-noise performance of impedance analyzer 117.

Anti-aliasing filter 1907 is typical of any analog-to digital conversion system and is used to prevent undesired frequency components contributing to the final result. Its operation is very similar to the anti-aliasing filter in DSC 1904. Though, the two amplifiers may be different, to accommodate their different positions in the signal chain and the different interface requirements of adjacent blocks. The analog signal is converted to digital form by the ADC 1908.

Figure 19B:
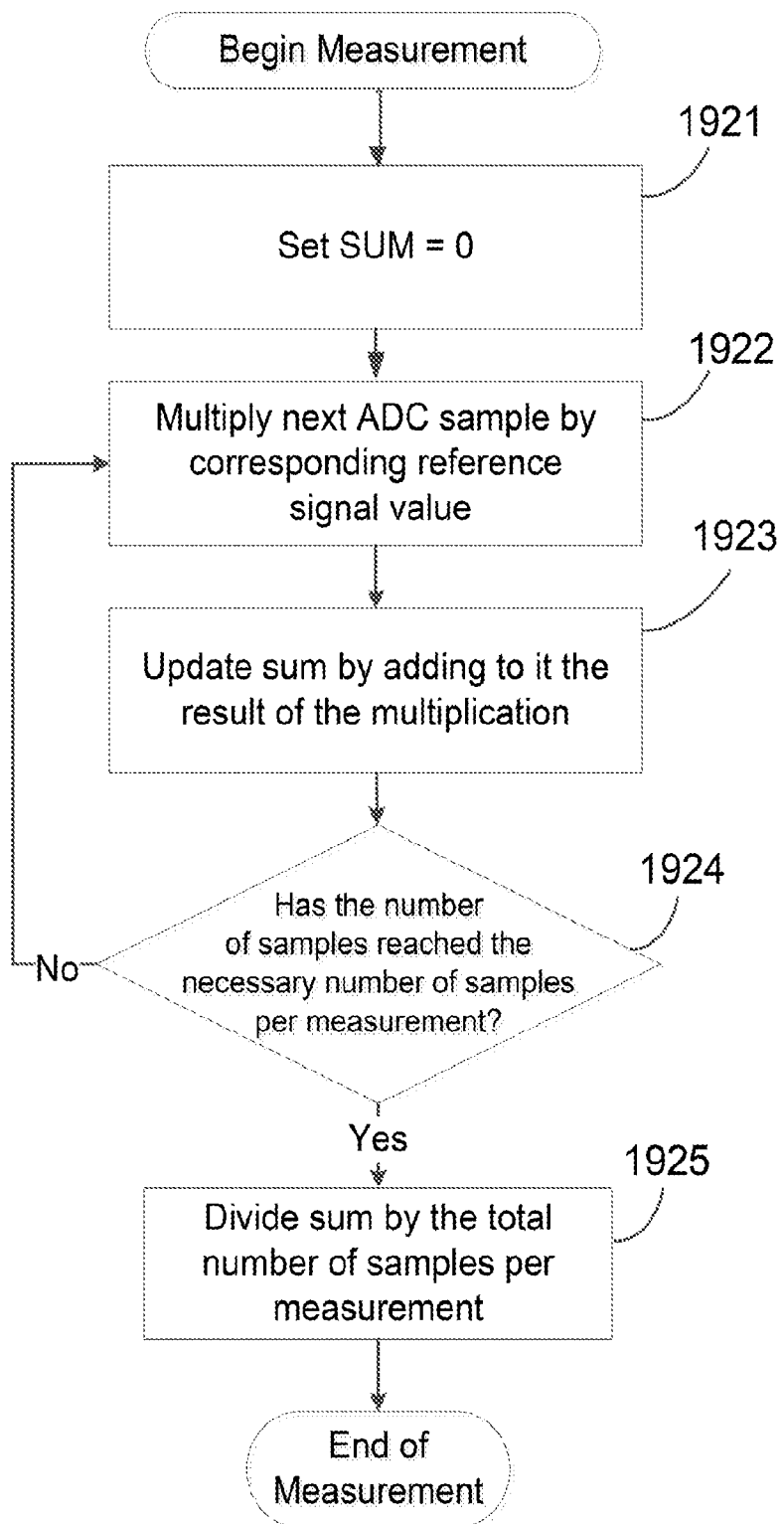

Multiply/accumulate block 1909 carries out the digital multiplication and low-pass filtering function analogous to those described with reference to FIG. 19B Block 1909 may include a separate parallel processing sub-block 1911-A for each component (real and imaginary) of each frequency. For example, in an embodiment that supports three frequencies, there will be a total of six instances of block 1911 in block 1909. Each block 1911 operates on the same input of digital samples from the ADC 1908. Each block 1911 uses a different reference signal obtained from reference signal generator 1901. For example, the block that computes the real component of the transimpedance at frequency $f_1$ uses an in-phase sinusoidal reference signal with frequency $f_1$, e.g., $\cos(2\pi f_1 t)$, and the block that computes the imaginary component of the transimpedance at frequency $f_1$ uses a quadrature (i.e., shifted in phase by 90° sinusoidal reference signal with frequency $f_1$, e.g., $\sin(2\pi f_1 t)$.

In typical legacy methods, all samples associated with a measurement must be collected before any processing (e.g., Fast Fourier Transform) can be performed. In the embodiment of impedance analyzer 117 described in connection with FIG. 19A, in each sub-block 1911 the data samples received from ADC 1908 are processed according to method 1920, described in connection with FIG. 19B. Advantageously, there is no requirement to buffer multiple samples from ADC 1908 before processing by module 1909. At the beginning of a measurement, the cumulative sum value is set to zero in step 1921. At every clock cycle, a new sample is received from ADC 1908. In step 1922, this sample value is multiplied by the corresponding reference signal value. After step 1922 is complete, the sample value is no longer needed and does not need to be saved. The result of the multiplication is added to the cumulative sum in step 1923. Steps 1922 and 1923 are repeated for each incoming sample until the prescribed total number of samples per measurement have been processed. The cumulative sum is divided by the total number of samples per measurement in step 1925. The result of this division is the output of method 1920, used by block 1911. The total number of samples per measurement is chosen such that it is an exact integral multiple of the number of samples per period for each frequency. This results in the earlier stated requirement $f_c = n \times f_m$. As noted above, the total number of samples per measurement is also chosen to be an exact power of 2, which substantially simplifies and speeds up the division operation in step 1925 of method 1920 by transforming the division operation into a simple bit shift operation.

As soon as method 1920 is complete and a measurement output value is obtained, method 1920 is executed again for the next measurement.

It is noted that all blocks 1911 operate in parallel on the same set of input samples. This process produces colocation in time and space of the real and imaginary components of the impedance at all frequencies, overcoming limitations of existing impedance analyzers that produce the real and imaginary parts of the impedance sequentially, inherently resulting in temporal differences and potentially resulting in spatial differences as well if, for example, the sensor is moving relative to the test object. Having the real and imaginary parts of the impedance at all frequencies be generated from the data taken at the same location at the same time may be used by algorithms, such as the multivariate inverse methods, which assume that the input quantities refer to the same location and the same point in time.

In some embodiments, block 1909 is implemented as an FPGA, allowing for the aforementioned parallel processing. Since these operations may be performed in real time, only the obtained transimpedance data need to be transmitted out of the instrument (rather than exporting all data samples). This allows for high data rates of, for example, 100, 1000s, or 10,000s of samples per second or more.

The control block 1910 configures and manages the operation of the other blocks in impedance analyzer 117, based on instructions received from instrument 110.

Section D: Detail of Data Processing

As discussed in connection with step 205 of method 200, impedance data produced by impedance analyzer 117 may be processed to produce estimated data. Estimate data may represent electromagnetic properties, geometric properties, material condition, or any type of measurement outcome. Like the impedance data, the estimated data may be registered in time and space.

Figure 20:
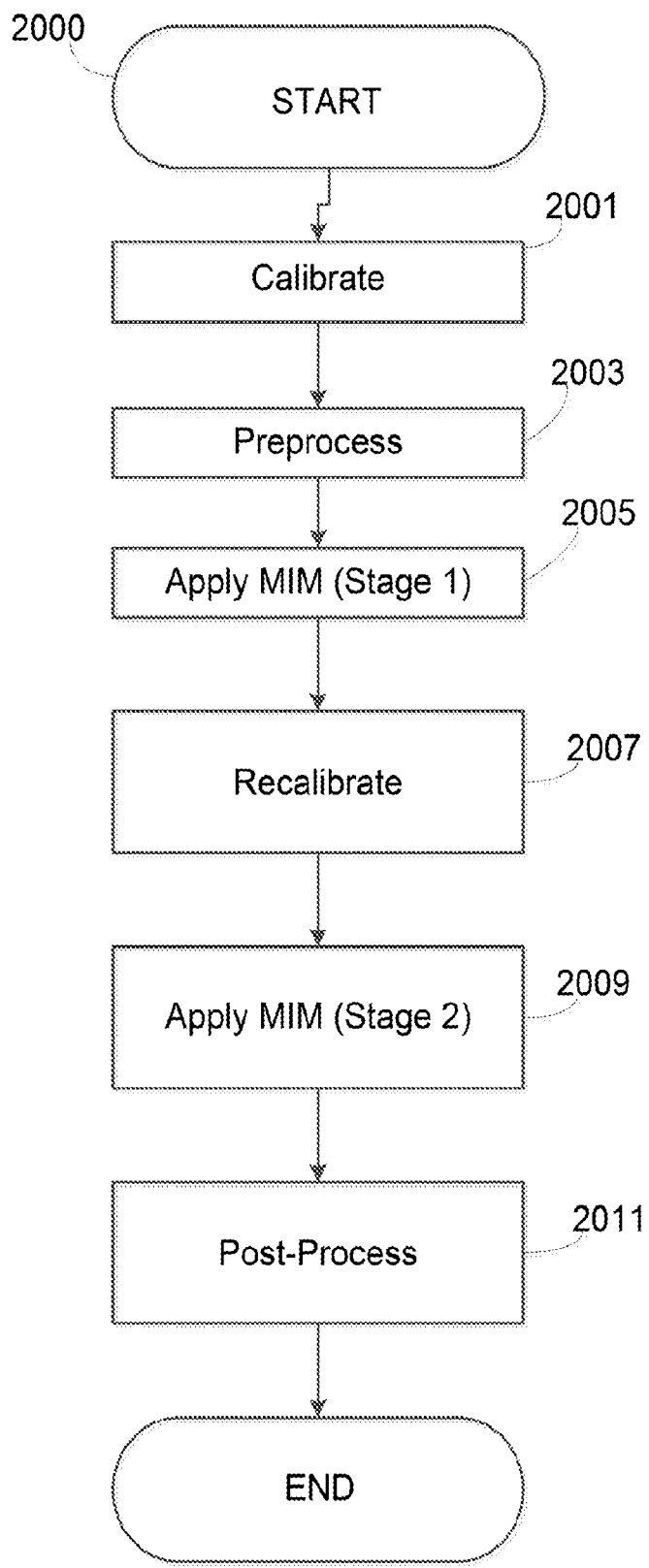

FIG. 20 shows method 2000 for transforming "raw" impedance data obtained from impedance analyzer 117 into the estimated data. As discussed in connection with step 207, this output may be presented through user interface 113 of instrument 110, or be passed to another apparatus for subsequent action. Method 2000 may be viewed as an embodiment of step 205 of method 200, though, method 2000 may be performed in isolation, or as part of any other suitable method.

At step 2001 raw impedance data is received and calibrated. Calibration procedures such as presented in [REFERENCE] may be used to convert the raw impedance data to "calibrated" impedance data. As discussed in REF, this step uses reference data obtained from on one or more known materials, possibly including only air, to inform a data transformation procedure. This procedure is tuned such that the transformed transimpedance values of measurements on the reference material(s) match those generated for the precomputed database at step 201 of method 200, FIG. 2 (e.g., calculated by a model).

At step 2003, the calibrated impedance data produced by step 2001 may be pre-processed. As multivariate inverse methods can, under certain circumstances, be very sensitive to instrumentation noise, i.e., signal variations that are not correlated with physical properties of the material under test. Accordingly, in some embodiments, a digital filter is applied to the calibrated impedance data. For example, a low-pass filter in time and/or space may be applied to the calibrated impedance data before it is converted to estimated data in subsequent steps. An example of such a filter is a weighted running average, with a weighting function such as a Gaussian "bell" curve or a "boxcar" function (equal weight given to all measurements in the window). Though, any suitable filter may be used.

In some embodiments at step 2001 calibrated impedance data from two or more channels is combined to produce a single impedance measurement. This step may be used, for example, to combine respective elements of arrays 307 and 308 of sensor 300, (shown in FIG. 3D of US Published application 2013/0124109) to achieve a narrower sensor footprint.

The output of step 2003 is pre-processed data. In some applications, such as for detection of corrosion under insulation, commonly observed material property variations ("material noise") may be so large as to mask the signal (e.g., the property variation) of interest for the application. A recalibration procedure involving steps 2005 and 2007 may be performed to improve visibility for such properties. In such embodiments, a subset of the pre-processed data is designated as a reference set. The reference set data may be taken from a location on the test object where additional assumptions can be made about the test object, further reducing the number of unknowns. This dataset may be obtained by acquiring data over sufficient area such that any defects have only a negligible contribution.

At step 2005 the reference set of pre-processed data is converted by a multivariate inverse method (MIM) into estimated material properties using the precomputed database generated at step 201 of method 200 and known property assumptions for the nominal test object properties. Alternatively, the known property assumptions may be incorporated into the database generation step, in which case that database will be utilized here at step 2005, while a second database that does not incorporate these assumptions is used at step 2009. The output of step 2005 is re-calibration data.

At step 2007 a second calibration (re-calibration) is applied to the pre-processed data from step 2003. The re-calibration uses the re-calibration data generated at step 2005. This step may be similar to step 2001, however, here the reference data is the re-calibration data obtained from test object itself rather than from a reference standard. As part of step 2007, but before the re-calibration data from the test object is used for re-calibration, each of the reference material properties may be averaged across channels (using the same value for each channel), or frequencies, or both. Using separate values for each channel makes it possible to account for actual channel-to-channel material variation in the reference data set. The output of step 2007 is re-calibrated data.

At step 2009, the re-calibrated data is processed using the multivariate inverse methods and precomputed databases. In some embodiments the number of unknown properties is greater than at step 2005 since the assumption that the properties are nominal may no longer be applied. The output of step 2009 is preliminary data.

At step 2011 the preliminary data is post processed to produce the estimated data. Similarly to step 2003, a digital filter or a running average may be applied to the preliminary data. In contrast to the treatment of instrument noise, which was addressed at step 2003, material noise, such as lift-off variation due to sensor motion or component surface roughness, is addressed at step 2011, after application of the multivariate inverse methods. The different treatment of instrument noise and material noise is because material noise associated with one property will appear only in the estimates of only that property. Whereas attempting to filter the impedance data to address such variations in one property can lead to inaccurate estimates in the other properties that are also part of the estimated data.

In some embodiments, at step 2011 a shape filter (reference needed) is applied to the preliminary data. Shape filtering cross-correlates the preliminary data with a "signature", i.e., known spatial variation of an estimated property that results from the presence of a discrete flaw, such as a crack or inclusion. Shape filtering results in sharper (higher magnitude, lower width) indications. Signatures may be stored in a library and extracted, possibly via interpolation, based on known or estimated material properties.

In some embodiments, at step 2011 application-specific filtering used to selectively reject invalid data, e.g., property variations due to unmodeled physical effects. For example, such a filter is used to reject CUI data in the vicinity of weather jacket straps, other pipes, physical supports, etc.

It should be appreciated that various embodiments of method 2000 may not include all steps presented here. For example, recalibration may not be required for some applications; accordingly, step 2005 and 2007 may be bypassed and the method may proceed directly to step 2009. The required steps may be determined by the specific application for which raw impedance data is being processed. Other variations will be apparent to one of skill in the art.

Figure 21:
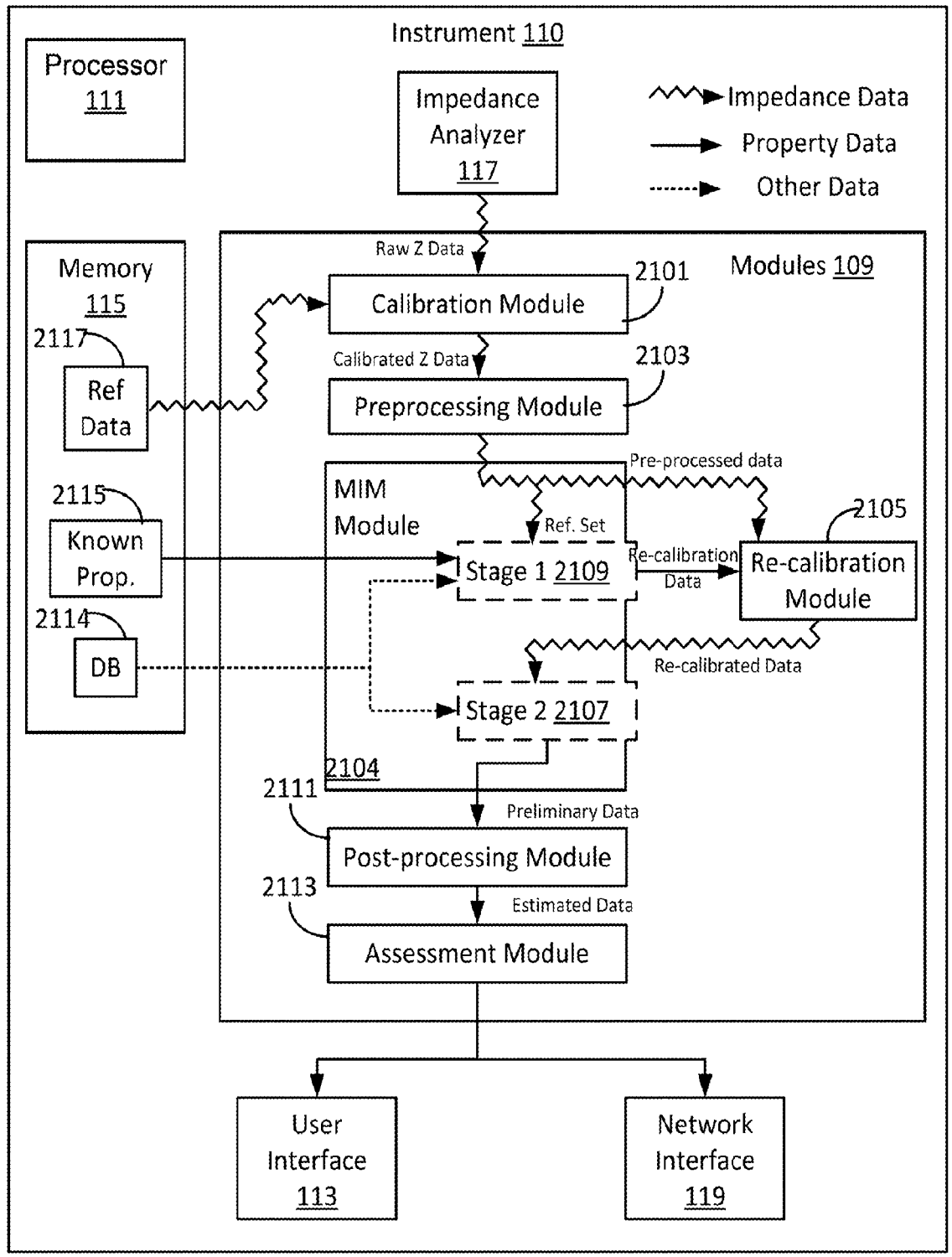

Turning now to FIG. 21, an embodiment of instrument 110 is discussed. Instrument 110 may be used to perform method 200, and method 2000. Instrument 110 may be similar to instrument 110 as described in connection with FIG. 1. Instrument 110 may include, for example, an impedance analyzer 117, processor 111, memory 115, user interface 113, network interface 119 and modules 109. Modules 109 may include a calibration module 2101, preprocessing module 2103, MIM module 2104, recalibration module 2105, post-processing module 2111, and assessment module 2113.

Impedance analyzer 117 may be an analyzer such as described above in Section C. Impedance analyzer 117 may be used to collect raw impedance data as described, for example, in connection with step 203.

Module 2101, is configured to implement step 2001 of method 2000. Specifically, calibration module 2101 calibrates raw impedance data received from impedance analyzer 117 using reference data 2117 which may be stored in memory 115.

Preprocessing module 2103 is configured to implement step 2003 of method 2000. Module 2103 receives calibrated impedance data provided by calibration module Q1 and performs pre-processing as described above. Preprocessing module generates pre-processed data. A subset of the pre-processed data is designated as the reference set.

MIM module 2104 performs a multivariate inverse method to estimate properties using pre-processed data provided by module 2103, a precomputed database 2114, and, optionally, property assumptions 2115. Module 2104 may be used to perform steps 2005 and 2009 of method 2000. To assist in illustration of data flow within instrument 110, a stage 1 block 2109 and stage 2 block 2107 are illustrated in module 2104. Block 2109 receives the inputs associated with step 2005, while block 2107 receives the inputs associated with step 2009. Specifically, as shown by block 2109, MIM module 2104 may receive the reference set of pre-processed data from preprocessing module 2103, database 2114, and property assumptions 2115 and perform a multivariate inverse method to provide recalibration data in accordance with step 2005. As shown by block 2107, MIM module 2104 may receive recalibrated data and database 2114 to provide preliminary data in accordance with step 2001.

Recalibration module 2105, may be configured to receive recalibration data from MIM module 2104 (see block 2109) to recalibrate pre-processed data. Recalibration module may be configured to implement step 2007 of method 2000.

Post processing module 2111 may be configured to implement step 2011 of method 2000. Module 2111 may be configured to receive preliminary data from MIM module 2104 and post-process the data to produce estimate data. The estimated data may be provided to assessment module 2113.

Assessment module 2113 may make an assessment of the estimate data. Module 2113 may be configured to perform step 207 of method 200, FIG. 2.

It should be appreciated that modules 109 of instrument 110 may include suitable modules to perform methods 200 and 2000 in any suitable way to implement.

3 Modeling of Eddy Current Sensors in Cylindrical Coordinates

The following sections describe a method for developing the precomputed databases of block 201 of FIG. 2. This is an extension into cylindrical coordinates of the Cartesian coordinate forward model of the eddy current sensor found in [1]-[3] and based on the transfer relations developed by Professor Melcher [4]. The cylindrical coordinate derivation is necessary for accurately modeling the eddy current sensor interaction when wrapped around a cylindrically shaped test object. Furthermore, since this model will be used in many applications where the material transport time interval determined by the characteristic length of the eddy current sensor divided by the scanning speed is comparable to the period of the sensor's current excitation, it will be important to incorporate the convective effect into the model [4].

The eddy current sensor is analyzed in the magnetoquasistatic (MQS) regime, which ignores the term due to displacement current in Ampere's law and assumes that the test object is comprised of very good conductors and very good insulators This assumes that the spatial period of the electromagnetic wave at the operating frequency is much greater than all other characteristic lengths including the spatial wavelength of the winding construct. Therefore, the electrodynamic contribution is negligible. Since the eddy current sensor is traditionally operated between DC and 40 MHz, and the period of the winding construct is generally on the order of a few inches or smaller, this assumption is always satisfied by at least 2-3 orders of magnitude. If the frequency is raised much above 40 MHz, capacitive effects need to be considered [1, 4].

The eddy current sensor is also analyzed in the sinusoidal steady state with angular frequency ω. Therefore, time dependent quantities can always be written in the following form in the frequency domain:

$$F(\vec{r},t) = \Re\{\hat{F}(\vec{r})e^{j\omega t}\} \quad (3.1)$$

where $\hat{F}$ is a complex amplitude function only of spatial coordinates $\vec{r}$. Therefore, derivatives in the time domain can be transformed into multiplications by $j\omega$ in the frequency domain.

The analysis of the eddy current sensor can be greatly simplified if the current density in each drive winding can be considered uniform, although this is not necessary for the precomputed database generation. This assumption provides a known current density whose spatial Fourier modes can be analyzed separately. The final magnetic field is simply the superposition of the individual solutions. The assumption is valid if the dimensions of the individual conductors are much smaller than the imposed spatial wavelength, the distance between the drive conductors and the secondary conductors, and the distance between the sensor conductors and the test object. This is the case for the sensors developed for CUI (where in this document CUI includes both internal and external corrosion related wall loss for inspection from the outside of a pipe, through insulation), for example. These models can be extended into the regime where these assumptions are invalid by using a collocation point method [1].

3.1 Motivation for the Cylindrical Eddy Current Sensor Model

Figure 22:
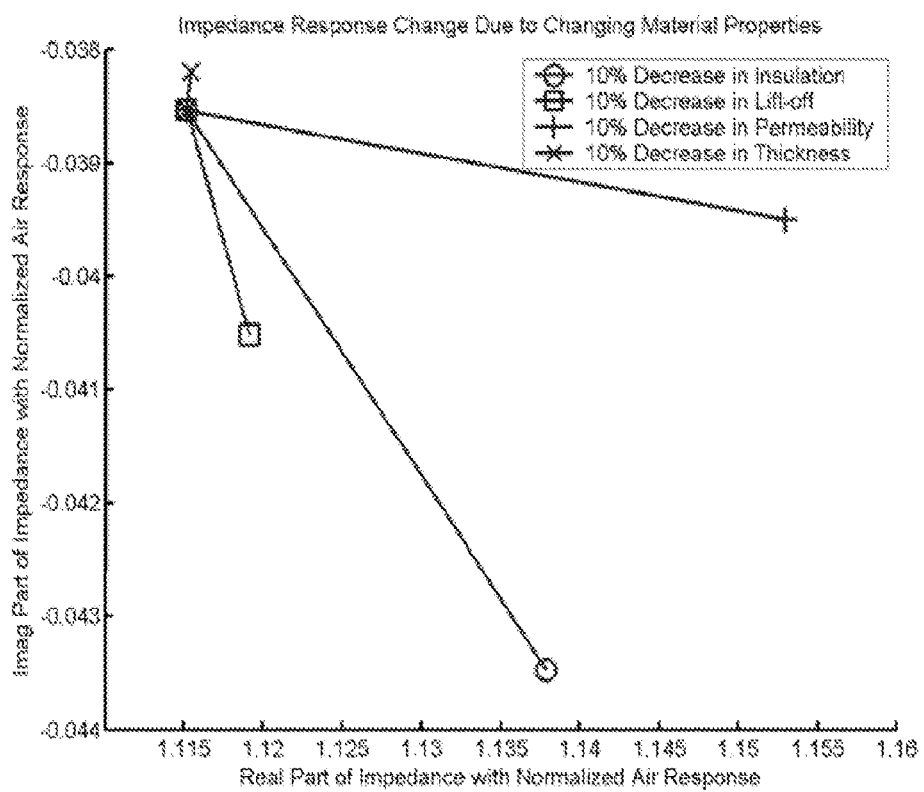

Most standard eddy-current methods use a reference calibration method when determining material properties or inspecting for flaws [Reference and Air calibration, sometimes called standardization, are defined in reference 7—ASTM Std E-2338]. They use a set of known standards and then empirically fit the resulting measurement to the known standard dataset. This often requires the assumption that properties other than the one of interest are constant. This is generally a terrible assumption—for the case of CUI, variations in insulation thickness can be dramatic from location to location and as described below the contribution of only a 10% insulation thickness variation is huge compared to thre response change due to a 10% wall thickness change). Simply moving from the top of the pipe (or pipeline) to the bottom can result in insulation changes on the order of inches due to sagging caused by the weight of the insulation itself FIG. 22 shows the relative impedance changes due to a 10% change in each material property for the CUI applications. All perturbations were around a nominal 0.5" thick steel plate with 2 inches of insulation, a 0.02" aluminum weatherjacket and a sensor lift-off of 0.5". The data is normalized so that the sensor response in air corresponds to 1+0 j. It is clear from this plot that, unless there is good correction (by deterministically removing the contribution from the response) for any variation in pipeline material properties, insulation thickness, and other relevant contributions, then small changes in thickness measurement will get swamped out by the these variations. Unfortunately, the property of interest is the property to which the impedance measured at the sensor terminals is the least sensitive—unless these contributions are deterministically removed. Since these material property variations are inevitable, a reference calibration method is not practical an the method ZZZ of calibrating in air and simultaneously estimating all properties using a multiple frequency inversion method is a justifiable approach. The goal is to enable the deterministic removal of the contributions of all major contributors to the impedance of the sensor, leaving only the wall thickness component. At the same time if each of these contributing elements, such as insulation thickness can be measured, their measurement provides a self-diagnostics capability since it is often known what there approximate values should be and what there allowable ranges are. Thus, in one embodiment of this invention not only are their contributions removed from the total response to enable measurement of the wall thickness, but also each of them are measured to support self-diagnostics for the system and the procedure as it is performed and in post inspection analysis.

As described in the following, the eddy current sensor models must be extended into cylindrical coordinates for applications such as CUI as the Cartesian-coordinate assumption is not valid when wrapping an eddy current sensor around a pipe or pipeline. The air-point itself can change by as much as 20% from a sensor being flat to being wrapped around a pipe. Simply trying to normalize this effect out by using an air-point calibration at the correct diameter could result in as much as a 50% error in property measurement.

Figure 23:
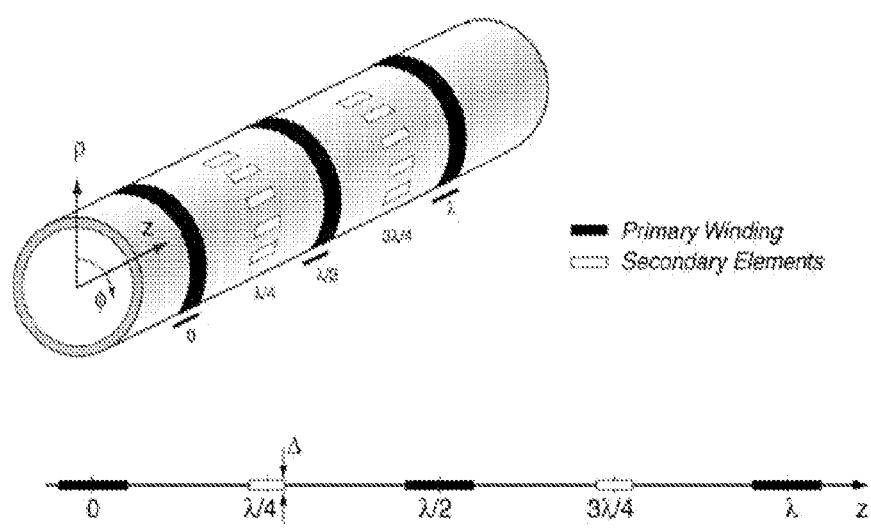

3.2 Eddy Current Sensor Forward Model in Cylindrical Coordinates: Drive Aligned with Φ-Axis This section contains the equations that predict the response of an eddy current sensor when wrapped around a cylindrical material in the typical scan orientation preferred for the most applications. The model assumes that the main legs of the primary winding are wrapped around the cylinder in the circumferential direction and that the periodicity of the primary winding is in the axial direction. Note that the periodic winding construct is later relaxed so that aperiodic winding constructs are also modeled. Secondaries are assumed to be on either side of the primary. Material properties are assumed to be independent of z, φ and time. Material interfaces are assumed to be at cylindrical surfaces of constant ρ. FIG. 23 shows the modeled eddy current sensor structure.

3.2.1 Maxwell's Equations

In the MQS regime, magnetic fields H in the presence of conducting materials must satisfy the magnetic diffusion equation:

$$\nabla^2 H - j\omega\sigma\mu H = 0 \quad (3.2)$$

When solving the magnetic diffusion equation, it is often easier to formulate the problem in terms of the magnetic vector potential A, defined as follows:

$$\nabla \times A = B \quad (3.3)$$

Combining this definition with Faraday's law:

$$\nabla \times E = j\omega B \quad (3.4)$$

results in the following:

$$\nabla \times E = \nabla \times (-j\omega A) \quad (3.5)$$

This states that E and $-j\omega A$ are vector fields with equal curl. Therefore, since vector fields with equal curl must be equal within an offset of a gradient of a scalar field, we can formulate results in the following:

$$E = (-j\omega A) - \nabla\Phi \quad (3.6)$$

where $\Phi$ is known as the electric scalar potential. Next we take into consideration Ampere's law, neglecting the term due to displacement current since we are in the MQS regime, $$\nabla \times H = J \quad (3.7)$$

We also require Ohm's law, including the term due to the current induced by the Lorentz force on the charge carriers, since the test object is in motion.

$$J = \sigma(E + v \times B) \quad (3.8)$$

Remembering $B = \mu H$ we can perform the following calculations:

$$\nabla \times \mu^{-1}(\nabla \times A) = -\sigma(j\omega A + \nabla \Phi - v \times B) \quad (3.9)$$

$$\nabla(\nabla \cdot A) - \nabla^2 A = -j\omega\mu\sigma A - \nabla(\mu\sigma\Phi) + \mu\sigma(v \times \nabla \times A) \quad (3.10)$$

$$\nabla^2 A - j\omega\mu\sigma A = \nabla(\nabla \cdot A + \mu\sigma\Phi) - \mu\sigma(v \times \nabla \times A) \quad (3.11)$$

It is important to note that these steps implicity assume that all layers of the test object are isotropic. That is, the off-diagonal terms of the conductivity and permeability tensor of each layer of the test object are zero. This is a good assumption for most applications and for most metals, including steel and aluminum and the materials used for insulating pipelines, satisfy this requirement.

Since Equation 3.3 only defined the magnetic vector potential with respect to its curl, we have the freedom to define the magnetic vector potential's divergence in order to uniquely determine it within a constant of integration. A convenient definition sets the first term of the RHS of Equation 3.11 to zero by letting $$\nabla \cdot A = -\mu\sigma\Phi \quad (3.12)$$

Therefore, we have reduced the problem to determining the magnetic vector potential that satisfies $$\nabla^2 A - j\omega\mu\sigma A = -\mu\sigma(v \times \nabla \times A) \quad (3.13)$$

In the limit where $v=0$, Equation 3.13 further reduces to:

$$\nabla^2 A - j\omega\mu\sigma A = 0 \quad (3.14)$$

Since the drive currents are only in the $\hat{\phi}$ direction and independent of $\phi$ as shown in FIG. 23, the magnetic vector potential solution to Equation 3.13 must also only have a $\hat{\phi}$ component and be independent of $\phi$. Also, since all quantities are independent of $\phi$, the $\hat{\phi}$ component of the velocity can be ignored, and we need only be concerned with the $\hat{z}$ component (i.e. $v = v_z \hat{z}$). So, Equation 3.13 reduces to:

$$\frac{1}{\rho}\frac{\partial}{\partial \rho}\left(\rho \frac{\partial A_\phi}{\partial \rho}\right) - \frac{A_\phi}{\rho^2} + \frac{\partial^2 A_\phi}{\partial z^2} - j\omega\mu\sigma A_\phi - \mu\sigma v_z \frac{\partial A_\phi}{\partial z} = 0 \quad (3.15)$$

It is important to note that when reducing Equation 3.13 to Equation 3.15, taking the Laplacian of a vector in cylindrical coordinates is not as simple as applying the cylindrical coordinate Laplacian to each component of the vector. Making this mistake will result in a differential equation with solution having an incorrect, non-physical $\rho$ dependence based on a zeroth order Bessel function as opposed to the correct $\rho$ dependence based on a first order Bessel function.

Using a separation of variables approach, we can postulate that A has the form $$A = A_{\phi_\rho}(\rho) A_{\phi_z}(z) \hat{\phi} \quad (3.16)$$

and therefore Equation 3.15 further reduces to:

$$A_{\phi_z}\left[\frac{1}{\rho}\frac{\partial}{\partial \rho}\left(\rho \frac{\partial A_{\phi_\rho}}{\partial \rho}\right) - \frac{A_{\phi_\rho}}{\rho^2} - j\omega\mu\sigma A_{\phi_\rho}\right] + A_{\phi_\rho}\left[\frac{\partial^2 A_{\phi_z}}{\partial z^2} - \mu\sigma v_z \frac{\partial A_{\phi_z}}{\partial z}\right] = 0 \quad (3.17)$$

We choose for the z dependency of $A_\phi$ to have the following form with period $\lambda$:

$$A_{\phi_{z_n}}(z) = e^{-jk_n z}, \quad k_n = \frac{2\pi n}{\lambda} \quad (3.18)$$

The Fourier harmonic wavenumbers, $k_n$, are used here as the periodicity in the $\hat{z}$ direction allows us to represent the magnetic vector potential as the superposition of the Fourier wavenumber modes, where n is any integer. Also, the sign of the exponent here is arbitrary since positive and negative complex wavenumbers need to be treated separately. This will be discussed later in this section.

Plugging Equation 3.18 into Equation 3.17, we are left with the following differential equation:

$$e^{-jk_n z}\left[\frac{\partial^2 A_{\phi_{\rho_n}}}{\partial \rho^2} + \frac{1}{\rho}\frac{\partial A_{\phi_{\rho_n}}}{\partial \rho} + \left(-k_n^2 - j\mu\sigma(\omega - v_z k_n) - \frac{1}{\rho^2}\right) A_{\phi_{\rho_n}}\right] = 0 \quad (3.19)$$

The above is a differential equation whose form is that of the transformed version of the Bessel differential equation given by [5].

$$\frac{d^2 y}{dx^2} - \frac{2\alpha - 1}{x}\frac{dy}{dx} + \left(\beta^2 r^2 x^{2r-2} + \frac{\alpha^2 - f^2 r^2}{x^2}\right) y = 0 \quad (3.20)$$

whose solution is $$y = x^\alpha [C_1 J_f(\beta x^r) + C_2 Y_f(\beta x^r)] \quad (3.21)$$

Equation 3.19 fits into this form where $x = \rho$, $y = A_{\phi_\rho}$, $\alpha = 0$, $r = 1$, $f = 1$ and $\beta = j\gamma_n$, and where the complex wavenumber $\gamma_n$ is defined as $$\gamma_n = \sqrt{k_n^2 + j\mu\sigma(\omega - v_z k_n)} \quad (3.22)$$

Therefore, the solutions to Equation 3.19 are linear combinations of $J_1(j\gamma_n \rho)$ and $Y_1(j\gamma_n \rho)$, Bessel functions of the first and second kind of the first order. Alternatively, the solution to Equation 3.19 can be written in terms of linear combinations of $I_1(\gamma_n \rho)$ and $K_1(\gamma_n \rho)$, modified Bessel functions of the first and second kind of the first order. Therefore the full solution for each mode of the magnetic vector potential can be written as $$A_n = [a_1 I_1(\gamma_n \rho) + a_2 K_1(\gamma_n \rho)] e^{-jk_n z} \hat{\phi} \quad (3.23)$$

It is interesting to note how velocity enters into the model. If a material is moving at velocity $v_z$ relative to a sensor, then the apparent frequency of excitation $\omega$ observed in that material is replaced by $\omega - v k_n$. This causes the presence of a non-zero velocity to break the symmetry around $n=0$ of the complex wavenumbers, requiring that positive and negative wavenumber modes be treated separately. This will be discussed further in Section 2.2.

Before continuing, there are a few internal consistencies and assumptions that need to be explored. First of all, the solutions for A provided by Equation 3.23 have zero divergence. Therefore, revisiting the gauge condition from Equation 3.12, the scalar potential $\Phi=0$, and Equation 3.6 can be rewritten as $$E = -j\omega A \tag{3.24}$$

Boundary conditions must be satisfied by Equation 3.24 in order for this model to be self consistent. First of all, at interfaces of conducting materials, where the tangential component of the electric field must be continuous, the boundary condition is satisfied as A has $\hat{\phi}$ component which is tangential to the interface boundaries. However, this is not necessarily the case at the sensor winding interface and in insulating regions near the sensor winding. Without an $\hat{r}$ component to A and, therefore, E it appears that electric field continuity cannot be maintained. However, when the conductivity of a layer is zero, the electric scalar potential $\Phi$ is not forced to zero by Equation 3.12. So the inconsistency is resolved by an appropriate solution to $\nabla^2\Phi=0$. Furthermore, the component of the magnetic field contributed by the non-zero electric scalar potential is disregarded in the MQS regime. One important consequence of this is that in order for the boundary condition at the winding surface to be met, the layers immediately adjacent to the winding must be insulating. This was already necessary, however, in order to contain the winding currents within the winding.

Plugging Equation 3.23 into Equation 3.3 we can also make some observations on the functional form of B.

$$B_n = -\frac{\partial A_{\phi_n}}{\partial z}\hat{\rho} + \frac{1}{\rho}\frac{\partial(\rho A_{\phi_n})}{\partial \rho}\hat{z} \tag{3.25}$$

$$= jk_n[a_1 I_1(\gamma_n\rho) + a_2 K_1(\gamma_n\rho)]e^{-jk_n z}\hat{\rho} +$$

$$\gamma_n[a_1 I_0(\gamma_n\rho) - a_2 K_0(\gamma_n\rho)]e^{-jk_n z}\hat{z}$$

At first glance it would appear that it is necessary to set $a_2=0$ in order to prevent both components of both A and B from diverging as $\rho\to 0$. However, doing so would make it impossible to satisfy all of the boundary conditions presented by a layered-material problem. This apparent discrepancy is resolved by noting that the material layers are varying in the $\hat{\rho}$ direction and, therefore, only one layer actually contains $\rho=0$. Only in that layer is it necessary for $a_2=0$. For numerical stability, it may be required to place a constraint on the minimum thickness of the layer surrounding $\rho=0$.

Furthermore, in order for the above MQS calculations to be valid, the materials must either be good conductors with only a $\hat{\phi}$ component to E or good insulators with only a normal component to E. Another way of formulating this is to say that the magnetic diffusion time, $\tau_m=\mu\sigma l^2$, must be much greater than the charge relaxation time, $\tau_e=\varepsilon/\sigma$, for any test object with a non-zero conductivity. The conductivities for which these two quantities become equal is determined by the following equation:

$$\sigma = \frac{1}{l}\sqrt{\frac{\varepsilon}{\mu}} \tag{3.26}$$

where l is a characteristic length scale such as the period of the magnetometer. Given the geometry of typical magnetometers, magnetic diffusion time is equal to charge relaxation time for conductivities on the order of 0.1-1 S/m. Therefore, the MQS approximation is valid for typical metals, which have conductivities in the mega-siemens per meter range, or for good insulators with a conductivity on the order of $10^{-12}$ S/m. For measurements on low conductivity materials, such as sea water, where the MQS approximation is not valid, the full set of Maxwell's equations must be considered.

3.2.2 Symmetry Considerations

To simplify the computational complexity of the semi-analytical solution to the eddy current sensor response, it is useful to exploit the symmetry of the sensor geometry. If the origin of our coordinate system is intelligently placed at the center of a primary winding as in FIG. 23, we can make some useful observations.

First, if motion is neglected, we can note that the symmetry constrains the $\hat{\rho}$-component of the magnetic flux density to be an odd function of z, and it constrains the $\hat{z}$-component to be an even function of z. This forces the exponential in the $\hat{\rho}$ term to simplify to a $\sin(k_n z)$ and the exponential in the $\hat{z}$ term to simplify to a $\cos(k_n z)$. In terms of the magnetic vector potential A, this can be formalized as $$\frac{\partial A_\phi}{\partial z}\bigg|_z = -\frac{\partial A_\phi}{\partial z}\bigg|_{-z}, A_\phi|_z = A_\phi|_{-z} \tag{3.27}$$

In order for this to be satisfied, according to Equation 3.23, A must be an even function of z More specifically, its z dependence is governed by $\cos(k_n z)$. Therefore, in a series expansion of A, only non-negative wavenumber modes need be considered.

While this is convenient to use in the simplified, stationary case, this symmetry breaks down in the presence of convection. When reflected across the $\phi$-$\rho$ plane, velocity in the $\hat{z}$-direction reverses and the even symmetry is broken. Therefore, in the presence of convection, positive and negative wavenumber modes must be considered separately.

The other symmetry to note is not broken by the presence of a non-zero velocity: a half period shift in the $\hat{z}$ direction reverses all currents, and, therefore, the sign of the magnetic vector potential. This can be formalized as $$A_\phi|_z = -A_\phi|_{z+\frac{1}{2}\lambda} \tag{3.28}$$

Since this translational symmetry condition cannot be satisfied by even wavenumber modes, only odd wavenumber modes need be considered.

3.2.3 Fourier Series Expansion

The magnetic field (and, therefore, the magnetic vector potential) can be represented as a superposition of all of the different Fourier wavenumber modes. Equation 3.23 provides the closed form solution for each individual mode. Therefore, the magnetic vector potential can be expressed as $$A_\phi(\rho, z) = \sum_{n=-\infty,odd}^{\infty} A_n(\rho)e^{-jk_n z} \tag{3.29}$$

As mentioned in the previous section, only odd wavenumber modes are required due to the translational symmetry condition in Equation 3.28.

3.2.4 Sensor Interaction with Material: Normalized Surface Reluctance Density Now that we have established a functional form for each wavenumber mode n, it is necessary to establish how the test object interacts with the eddy current sensor. All of this information is contained within the normalized surface inductance density, which is defined as:

$$L_n(\rho, z) = k_n \frac{A_{\phi_n}(\rho, z)}{H_{z_n}(\rho, z)} \quad (3.30)$$

In order to stay consistent with implementations of related models [1]-[3] we will use the inverse of the normalized surface inductance density, which has been referred to as the normalized surface reluctance density. Even though this is a slight misnomer (as the inverse of reluctance is permeance, not inductance), there is no better term for the inverse of inductance so it will be used in this document as well. The normalized surface reluctance density is defined as:

$$R_n(\rho, z) = \frac{1}{L_n(\rho, z)} = \frac{1}{k_n} \frac{H_{z_n}(\rho, z)}{A_{\phi_n}(\rho, z)} \quad (3.31)$$

Based on Equation 3.23, we can write $$A_{\phi_n}(\rho, z) = A_n(\rho) e^{-jk_n z} \quad (3.32)$$

where $$A_n(\rho) = a_1 I_1(\gamma_n \rho) + a_2 K_1(\gamma_n \rho) \quad (3.33)$$

From Equation 3.25, we can write $$H_{z_n}(\rho, z) = \frac{1}{\mu \rho} \frac{\partial (\rho A_{\phi_n})}{\partial \rho} = H_n(\rho) e^{-jk_n z} \quad (3.34)$$

where $$H_n(\rho) = \frac{\gamma_n}{\mu} [a_1 I_0(\gamma_n \rho) - a_2 K_0(\gamma_n \rho)] \quad (3.35)$$

Therefore, plugging Equations 3.32 and 3.34 into Equation 3.31 we can conclude that $$R_n(\rho, z) = R_n(\rho) = \frac{1}{k_n} \frac{H_n(\rho)}{A_n(\rho)} \quad (3.36)$$

Figure 24:
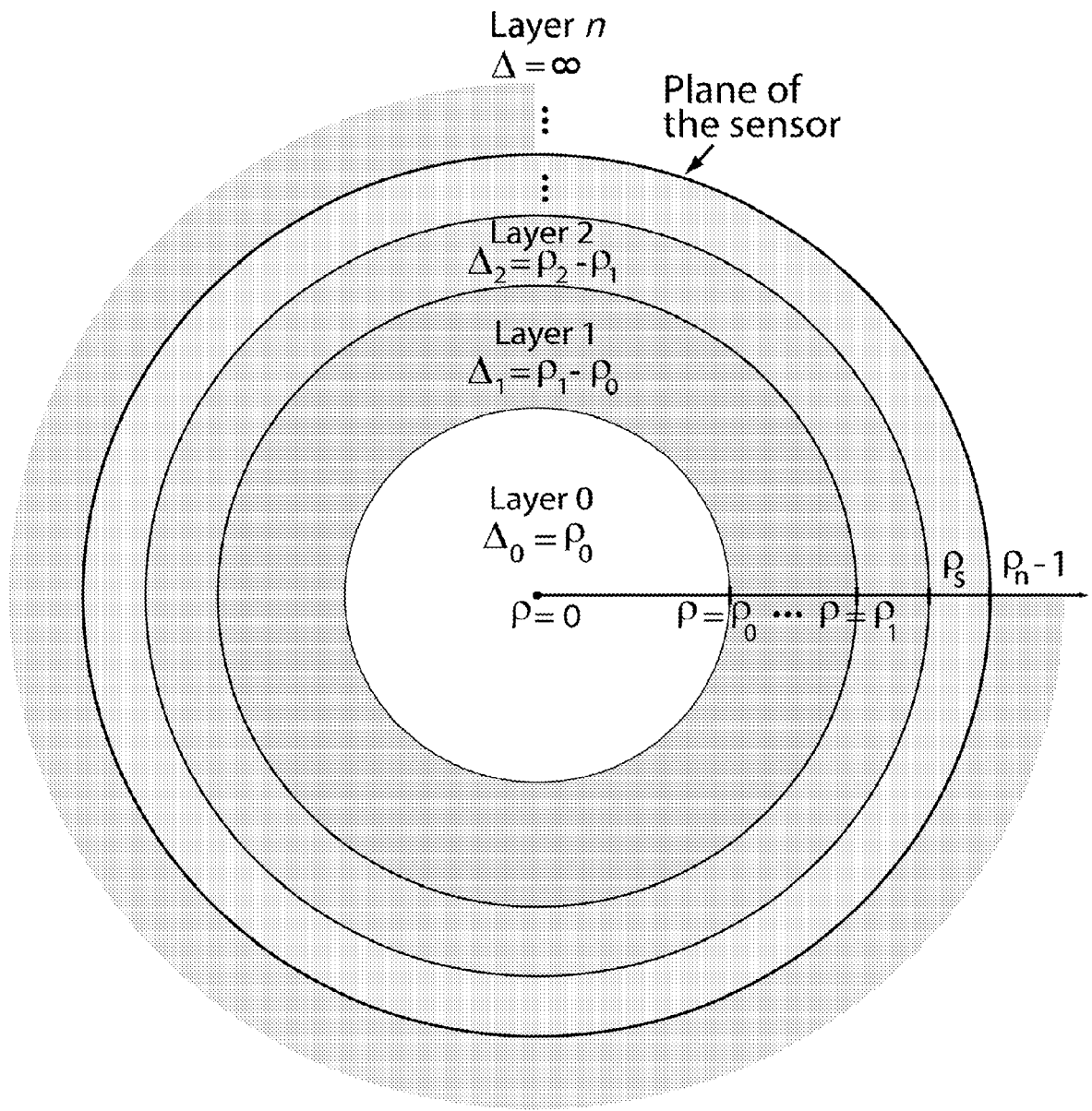

It is useful to first determine how $R_n(\rho)$ behaves at the first and last material interfaces, at $\rho=\rho_0$ and $\rho=\rho_{N-1}$ respectively, as shown in FIG. 24. In the innermost material layer which contains $\rho=0$, it is necessary for $a_2=0$, as $K(\gamma_n \rho)$ diverges at $\rho=0$. Therefore, at the innermost material interface $$R_n(\rho_0) = \frac{\gamma_n}{\mu k_n} \frac{I_0(\gamma_n \rho_0)}{I_1(\gamma_n \rho_0)} \quad (3.37)$$

In the outermost layer which contains $\rho=\infty$, $I(\gamma_n \rho)$ diverges as $\rho \to \infty$, so we can immediately say that $a_1=0$. Therefore, at the outermost material interface $$R_n(\rho_{N-1}) = -\frac{\gamma_n}{\mu k_n} \frac{K_0(\gamma_n \rho_0)}{K_1(\gamma_n \rho_0)} \quad (3.38)$$

One useful sanity check is that as $\rho$ gets large, the cylindrical case converges to the Cartesian case, which is indeed the case [2].

$$\lim_{\rho \to \infty} R_n(\rho) = -\frac{\gamma_n}{\mu k_n} \lim_{\rho \to \infty} \frac{K_0(\rho)}{K_1(\rho)} = -\frac{\gamma_n}{\mu k_n} \quad (3.39)$$

Given a transfer function that relates $R_n(\rho_i)$ at one interface of a layer of thickness t to the interface on the other side of the layer at $R_n(\rho_{i+1})=R_n(\rho_{i+t})$, it is possible to begin at the innermost and outermost layer, apply the transfer function across each layer consecutively, and end up with an expression for the surface reluctance density on either side of the plane of the sensor, $R_n(\rho_s^+)$ and $R_n(\rho_s^-)$. The difference between these two quantities, defined as $R_n$, can then be related back to the wavenumber mode of the surface current density in the plane of the windings, $K_S$, as follows:

$$R_n = R_n(\rho_s^+) - R_n(\rho_s^-) = \frac{1}{k_n} \frac{H_{z_n}(\rho_s^+, z) - H_{z_n}(\rho_s^-, z)}{A_{\phi_n}(\rho_s, z)} = \frac{1}{k_n} \frac{K_{S_n}}{A_n(\rho_s)} \quad (3.40)$$

where $$K_S(z) = \sum_{n=-\infty}^{\infty} K_{S_n} e^{-jk_n z} \quad (3.41)$$

The desired transfer relation can be derived from Equation 25 in Section 2.16 of [4] which formulates the magnetic vector potential everwhere in a layer in terms of its value at the two interfaces of the layer which are at $\rho=\rho_i$ and $\rho=\rho_i+t$:

$$A_n(\rho) = A_n(\rho_i) \frac{I_1(\gamma_n(\rho_i+t))K_1(\gamma_n \rho) - K_1(\gamma_n(\rho_i+t))I_1(\gamma_n \rho)}{I_1(\gamma_n(\rho_i+t))K_1(\gamma_n \rho_i) - K_1(\gamma_n(\rho_i+t))I_1(\gamma_n \rho_i)} - \quad (3.42)$$
$$A_n(\rho_i+t) \frac{I_1(\gamma_n \rho_i)K_1(\gamma_n \rho) - K_1(\gamma_n \rho_i)I_1(\gamma_n \rho)}{I_1(\gamma_n(\rho_i+t))K_1(\gamma_n \rho_i) - K_1(\gamma_n(\rho_i+t))I_1(\gamma_n \rho_i)}$$

We can see that this equation must be true as both $I_1$ and $K_1$ satisfy Equation 3.19 and it is self-consistent at the two interfaces of the layer. Using Equations 3.34, 3.36, and 3.42, we can formulate the following equations for the surface reluctance density at the two interface layers:

$$R_n(\rho_i) = -\frac{\gamma_n}{\mu^* k_n} \frac{I_1(\gamma_n(\rho_i+t))K_0(\gamma_n \rho_i) + K_1(\gamma_n(\rho_i+t))I_0(\gamma_n \rho_i)}{I_1(\gamma_n(\rho_i+t))K_1(\gamma_n \rho_i) - K_1(\gamma_n(\rho_i+t))I_1(\gamma_n \rho_i)} + \quad (3.43)$$
$$\frac{\gamma_n}{\mu^* k_n} \frac{I_1(\gamma_n \rho_i)K_0(\gamma_n \rho_i) + K_1(\gamma_n \rho_i)I_0(\gamma_n \rho_i)}{I_1(\gamma_n(\rho_i+t))K_1(\gamma_n \rho_i) - K_1(\gamma_n(\rho_i+t))I_1(\gamma_n \rho_i)} \frac{A_n(\rho_i+t)}{A_n(\rho_i)}$$

-continued $$R_n(\rho_i + t) = \tag{3.44}$$
$$-\frac{\gamma_n}{\mu^* k_n} \frac{I_1(\gamma_n(\rho_i + t))K_0(\gamma_n(\rho_i + t)) + K_1(\gamma_n(\rho_i + t))I_0(\gamma_n(\rho_i + t))}{I_1(\gamma_n(\rho_i + t))K_1(\gamma_n\rho_i) - K_1(\gamma_n(\rho_i + t))I_1(\gamma_n\rho_i)}$$
$$\frac{A_n(\rho_i)}{A_n(\rho_i + t)} +$$
$$\frac{\gamma_n}{\mu^* k_n} \frac{I_1(\gamma_n\rho_i)K_0(\gamma_n(\rho_i + t)) + K_1(\gamma_n\rho_i)I_0(\gamma_n(\rho_i + t))}{I_1(\gamma_n(\rho_i + t))K_1(\gamma_n\rho_i) - K_1(\gamma_n(\rho_i + t))I_1(\gamma_n\rho_i)}$$

Finally, we can combine Equations 3.43 and 3.44, eliminating $A_n$ from the expression, leaving us with a transfer function that relates the surface reluctance density at one layer interface to the next.

$$R_n(\rho_i + t) = G_n(\rho_i + t)F_n(\rho_i + t)\frac{G_n(\rho_i)}{R_n(\rho_i) - F_n(\rho_i)} \tag{3.45}$$

where $$F_n(x) = -\frac{\gamma_n}{\mu^* k_n} \frac{I_1(\gamma_n(\rho_i + t))K_0(\gamma_n x) + K_1(\gamma_n(\rho_i + t))I_0(\gamma_n x)}{I_1(\gamma_n(\rho_i + t))K_1(\gamma_n\rho_i) - K_1(\gamma_n(\rho_i + t))I_1(\gamma_n\rho_i)} \tag{3.46}$$

$$G_n(x) = +\frac{\gamma_n}{\mu^* k_n} \frac{I_1(\gamma_n\rho_i)K_0(\gamma_n x) + K_1(\gamma_n\rho_i)I_0(\gamma_n x)}{I_1(\gamma_n(\rho_i + t))K_1(\gamma_n\rho_i) - K_1(\gamma_n(\rho_i + t))I_1(\gamma_n\rho_i)} \tag{3.47}$$

3.2.5 Implementation and Validation

Since the current densities in the plane of the primary windings can be considered uniform for this model, as discussed earlier, the magnetic field at the sense element due to a unit current excitation in the presence of the test object can be determined using the following steps:
1. Define the current density in the primary windings based on knowledge of the sensor geometry and winding position and using the uniform current density assumption. Take the Fourier transform of the current density profile to determine the wavenumber modes of the surface current density.
2. For each wavenumber mode, start at the innermost and outermost material interface and apply the transfer functions defined in Section 2.4 to determine the surface reluctance density on either side of the plane of the primary windings.
3. Calculate the magnetic vector potential in the plane of the primary windings for each wavenumber mode using Equation 3.40. Convert this to the magnetic vector potential in the plane of the sense element using Equation 3.42.
4. Calculate the magnetic field for each wavenumber mode at the sense element using Equation 3.25.
5. Determine the total magnetic field at the sense element due to a unit current excitation by summing the individual wavenumber modes.

While the above steps are relatively simple to implement in Matlab or other such software packages, care must be taken to make the simulation efficient. The two most important parameters that can be adjusted to affect the trade-off between simulation time and simulation accuracy are the simulation extent and the sampling interval. Based on the size of the sensor, a simulation extent needs to be chosen such that the model assumption that the sensor is infinitely periodic, when the sensor is actually finite, does not degrade the simulation accuracy. Furthermore, a sampling interval must be chosen that is small enough so that the drive excitation can be accurately represented, and so that high enough wavenumber modes can be calculated. As expected, as the sampling interval decreases, or as the simulation extent increases for a given sampling interval, the simulation time increases. In practice, simulation convergence is accomplished when the simulation extent is 5-10 times the size of the sensor. For the sensor geometries used for the CUI application, a sampling interval of 1 mm is necessary.

Furthermore, Bessel functions are expensive (in terms of time) to calculate in Matlab. Much simulation time can be saved by taking into consideration the assymptotic nature of the modified Bessel function as their argument gets large [6]. It is interesting to note that this is the equivalent of using the Cartesian coordinate model for large ρ.

One of the main difficulties in validating the derived model was manufacturing an appropriate sensor. Many iterations were required before a sensor construct was created satisfying the requirements of the model. Thus, one embodiment of this invention is the iterative design of a sensor that has a response that matches the model predicted response, by empirically comparing the sensor and model responses and modifying the design to obtain close agreement using intuition gained from the models and empirical data. The two most difficult requirements were creating a many-turn drive winding where the location of each winding was accurately known and maintaining the sense element's position relative to the winding when the sensor is wrapped around a cylinder. FIG. 25 shows the first sensor that successfully matched the models. A flat wire with a 2:1 aspect ratio was used for the drive winding so that, when constructing a multiple turn winding, the position of each wire could be more easily controlled because each wire lies vertically next to the last. Other such designs that maintain the sensor winding positional integrity are also included in this invention. The flexible printed circuit board with the MR elements is potted with the drive winding such that the elements are on the same bending axis as the drive wire. Therefore, regardless of the radius of curvature, the MR elements are in the same cylindrical surface as the drive.

Figure 26:
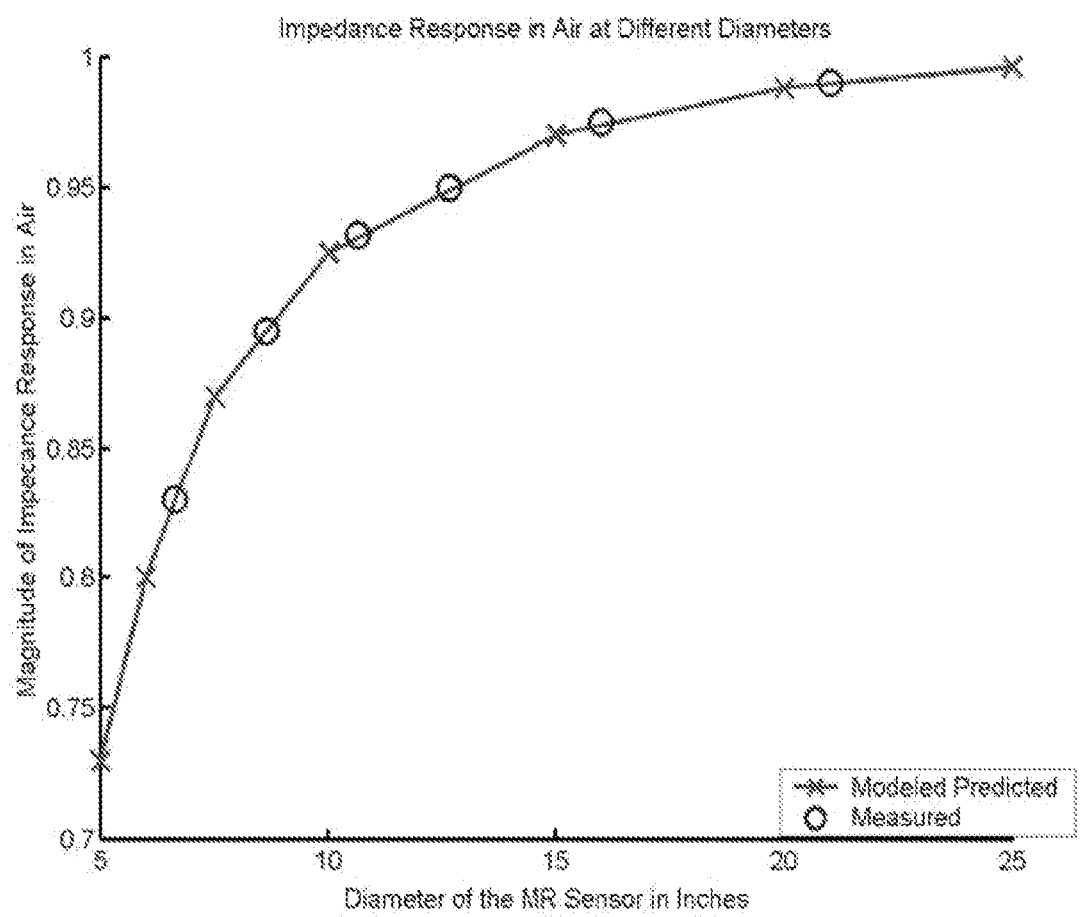
Figure 27:
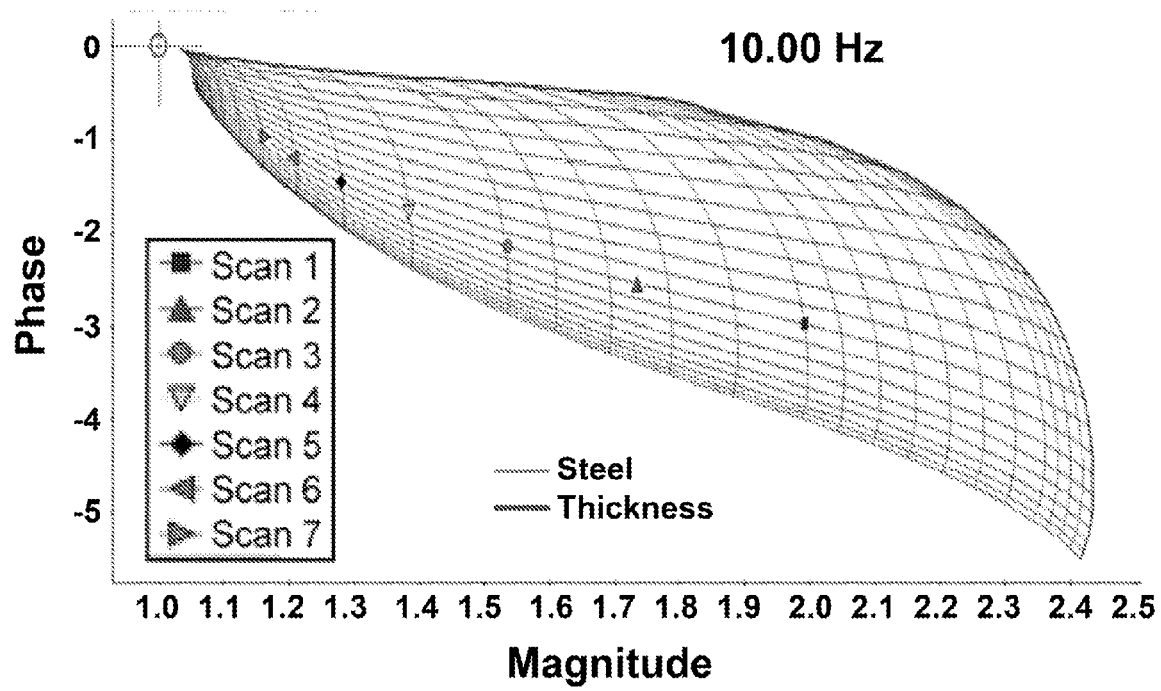

FIG. 26 and FIG. 27 show the results that validated the cylindrical model implementation. FIG. 26 shows that the model successfully predicts the air responses of the sensor when wrapped around plastic cylinders of varying diameters. The response of the sensor in air when flat was normalized to 1+0 j. Only the magnitude of the impedance response is plotted as the phase was always zero. The RMS error of the measured air responses as compared to the model-predicted air responses is under 0.05%. This is well within the tolerances of the experimental setup. FIG. 27 shows the results of taking measurements on a 6.625" diameter, 0.25" wall thickness pipe at varying lift-offs plotted on a lift-off/thickness grid. The air point represents the sensor's response in air when at a diameter of 10.625" (6.625" pipe+2" of insulation). As the lift-off is increased, the data follows the lift-off line up towards the air point. As the lift-off increased from 0.5" to 2.5", the estimated thickness varied only by ±0.002", with estimates ranging from 0.248" to 0.251". Lift-off lines are defined as lines in the visual representation of the precomputed database for which only the lift-off varies and other properties are constant.

Figure 28:
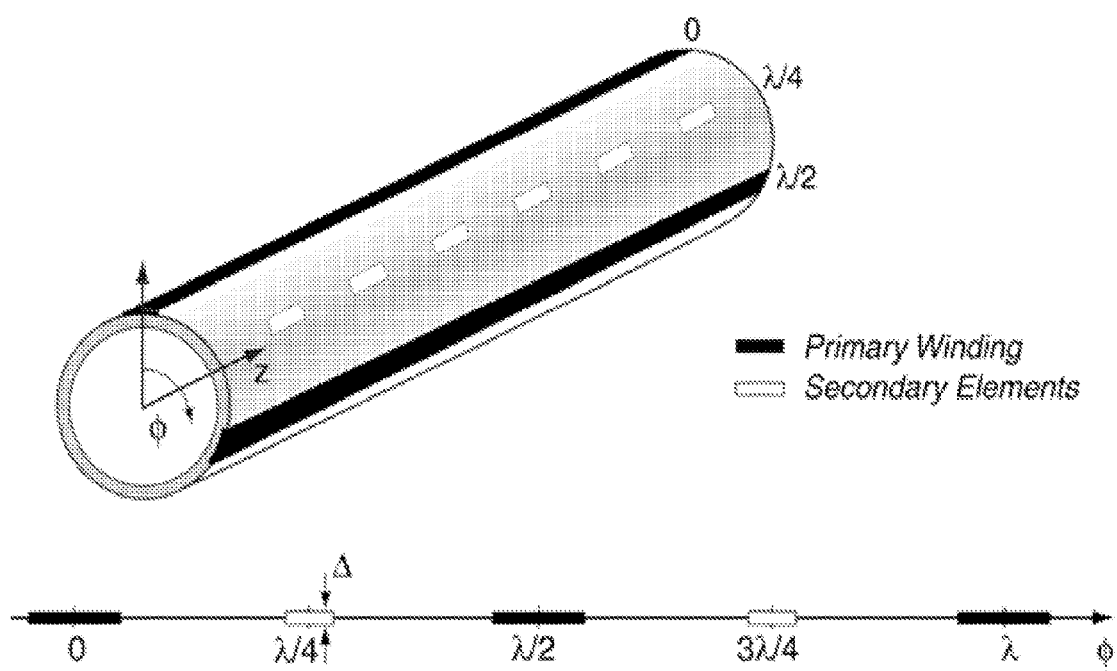

3.3 Eddy Current Sensor Forward Model in Cylindrical Coordinates: Drive Aligned with Z-Axis Depending on the specifics of an application, it may be necessary to scan a pipe or pipeline circumferentially, with the drive aligned along the pipeline's axis. This section contains the equations that predict the response of an eddy current sensor when wrapped around a pipe in this orientation. The model assumes that the main legs of the primary winding are aligned with the axis of the pipe and that the periodicity of the primary winding is in the circumferential direction. Secondaries are assumed to be on either side of the primary. Material properties are still assumed to be independent of z, $\phi$ and time and material interfaces are still assumed to be at cylindrical surfaces of constant $\rho$. FIG. 28 shows the modeled eddy current sensor structure.

3.3.1 Maxwell's Equations

In this formulation, we can begin with Equation 3.13. Assuming that the sensor is periodic in the $\hat{\phi}$ direction with period $\lambda$ and that the drive currents are only in the $\hat{z}$ direction and independent of z as shown in FIG. 28, the magnetic vector potential solution to Equation 3.13 must also only have a $\hat{z}$ component and be independent of z. Also, since all quantities are independent of z, the $\hat{z}$ component of the velocity can be ignored, and we need only be concerned with the $\hat{\phi}$ component (i.e. $v=v_\phi\hat{\phi}$). Furthermore, during scanning, the material moves with a common angular velocity (i.e. $v=\rho\omega_\phi\hat{\phi}$). So, Equation 3.13 reduces to:

$$\frac{1}{\rho}\frac{\partial}{\partial\rho}\left(\rho\frac{\partial A_z}{\partial\rho}\right) + \frac{1}{\rho^2}\frac{\partial^2 A_z}{\partial\phi^2} - j\omega\mu\sigma A_z - \mu\sigma\omega_\phi\frac{\partial A_z}{\partial\phi} = 0 \qquad (3.48)$$

For this geometry, it is important to note that the angular periodicity in the $\hat{\phi}$ direction must be limited to integer divisors of $2\pi$. That is, $$\lambda = \frac{2\pi}{n}\rho$$

where n=1, 2, 3 . . . .

We can use a separation of variables approach and postulate that A has the form $$A = A_{z_\rho}(\rho)A_{z_\phi}(\phi)\hat{z} \qquad (3.49)$$

and therefore Equation 3.48 further reduces to $$A_{z_\phi}\left[\frac{1}{\rho}\frac{\partial}{\partial\rho}\left(\rho\frac{\partial A_{z_\rho}}{\partial\rho}\right) - j\omega\mu\sigma A_{z_\rho}\right] + \qquad (3.50)$$
$$A_{z_\rho}\left[\frac{1}{\rho^2}\frac{\partial^2 A_{z_\phi}}{\partial\phi^2} - \mu\sigma\omega_\phi\frac{\partial A_{z_\phi}}{\partial\phi}\right] = 0$$

Knowing the structure of the sensor's periodicity in the $\hat{\phi}$-direction, we can say that the $\phi$ dependency of $A_z$ has the form $$A_{z_{\phi_n}}(\phi) = e^{-jn\phi} \qquad (3.51)$$

Similarly to the previous derivation, the sign of the exponent here is arbitrary since positive and negative complex modes need to be treated separately because of the lack of symmetry due to the velocity term.

Plugging Equation 3.51 into Equation 3.50, we are left with the following differential equation:

$$e^{-jn\phi}\left[\frac{\partial^2 A_{z_{\rho_n}}}{\partial\rho^2} + \frac{1}{\rho}\frac{\partial A_{z_{\rho_n}}}{\partial\rho} + \left(\frac{-n^2}{\rho^2} - j\mu\sigma(\omega - \omega_\phi n)\right)A_{z_{\rho_n}}\right] = 0 \qquad (3.52)$$

Equation 3.52 is in the familiar form of the tranformed Bessel function equation where x=$\rho$, y=$A_{z_\rho}$, $\alpha$=0, r=1, $f$=n and $\beta$=j$\gamma_{n'}$, where we define the complex wavenumber, $\gamma_{n'}$, as $$\gamma_{n'} = \sqrt{j\mu\sigma(\omega - \omega_\phi n)} \qquad (3.53)$$

Therefore, the full solution for the magnetic vector potential for the general case, with drive wires aligned axially, can be written as $$A_n = [a_1 I_n(\gamma_{n'}\rho) + a_2 K_n(\gamma_{n'}\rho)]e^{-jn\phi}\hat{z} \qquad (3.54)$$

The case where $\sigma$=0 must be considered separately as the arguments of the bessel functions would be equal to zero. In this case the solution to the magnetic vector potential is much simpler $$A_n = [a_1\rho^n + a_2\rho^{-n}]e^{-jn\phi}\hat{z} \qquad (3.55)$$

The angular velocity enters into this model in a similar manner as before. If a material is moving at angular velocity $\omega_\phi$ relative to a sensor, then the apparent frequency of excitation $\omega$ observed in that material is replaced by $\omega - \omega_\phi n$. This again causes non-zero velocity to break the symmetry around n=0 of the wavemodes, requiring that positive and negative wavemodes be treated separately. This will be discussed further in the next section.

Plugging Equation 3.54 into Equation 3.3 provides us with a formulation for B.

$$B_n = \frac{1}{\rho}\frac{\partial A_{z_n}}{\partial\phi}\hat{\rho} - \frac{\partial A_{z_n}}{\partial\rho}\hat{\phi} \qquad (3.56)$$
$$= -\frac{jn}{\rho}[a_1 I_n(\gamma_{n'}\rho) + a_2 K_n(\gamma_{n'}\rho)]e^{-jn\phi}\hat{\rho}$$
$$-\gamma_{n'}[a_1 I'_n(\gamma_{n'}\rho) - a_2 K'_n(\gamma_{n'}\rho)]e^{-jn\phi}\hat{\phi}$$

where $$K'_n(\gamma_{n'}\rho) = \frac{K_{n-1}(\gamma_{n'}\rho) + K_{n+1}(\gamma_{n'}\rho)}{2}, \qquad (3.57)$$
$$I'_n(\gamma_{n'}\rho) = \frac{I_{n-1}(\gamma_{n'}\rho) + I_{n+1}(\gamma_{n'}\rho)}{2}$$

It is necessary to set $a_2$=0 in the material layer that contains $\rho$=0 in order to prevent both components of both A and B from diverging as $\rho\to 0$. For numerical stability, it may be required to place a constraint on the minimum thickness of the layer surrounding $\rho$=0. For the case where $\rho$=0, Equation 3.56 leads to $$B_n = \frac{-jn}{\rho}[a_1\rho^n + a_2\rho^{-n}]e^{-jn\phi}\hat{z} - \frac{n}{\rho}[a_1\rho^n + a_2\rho^{-n}]e^{-jn\phi}\hat{\phi} \qquad (3.58)$$

3.3.2 Symmetry Considerations

The symmetry conditions in this model that persist in the presence of convection are analagous to the previous model.

A half-period shift in the $\hat{\phi}$ direction reverses all currents, and, therefore, the sign of the magnetic vector potential. This can be formalized as $$A_z|_\phi = -A_z|_{\phi+\pi} \tag{3.59}$$

Since this rotational symmetry condition cannot be satisfied by even wavenumber modes, only odd wavenumber modes need be considered.

3.3.3 Fourier Series Expansion

The periodicity of the sensor in the $\phi$ direction allows us to represent the magnetic field and the magnetic vector potential as a superposition of the different wavemodes. Equation 3.54 provides the closed form solution for each individual mode. The magnetic vector potential can be expressed as $$A_z(\rho, \phi) = \sum_{n=-\infty, odd}^{\infty} A_n(\rho) e^{-jn\phi} \tag{3.60}$$

As mentioned in the previous section, only odd wavenumber modes are required due to the translational symmetry condition in Equation 3.59.

3.3.4 Sensor Interaction with Material: Normalized Surface Reluctance Density

The test object's interaction with the eddy current sensor is characterized by the surface reluctance density, now defined as $$R_n(\rho, \phi) = \frac{1}{L_n(\rho, \phi)} = \frac{1}{k_n} \frac{H_{\phi_n}(\rho, \phi)}{A_{z_n}(\rho, \phi)} = \frac{\rho}{n} \frac{H_{\phi_n}(\rho, \phi)}{A_{z_n}(\rho, \phi)} \tag{3.61}$$

Our formulation follows the same logic as in the previous model. Based on Equation 3.54, we can write $$A_{z_n}(\rho, \phi) = A_n(\rho) e^{-jn\phi} \tag{3.62}$$

where $$A_n(\rho) = a_1 I_n(\gamma_n' \rho) + a_2 K_n(\gamma_n' \rho) \tag{3.63}$$

or when $\sigma=0$, $$A_n(\rho) = a_1 \rho^n + a_2 \rho^{-n} \tag{3.64}$$

From Equation 3.56, we can write $$H_{\phi_n}(\rho, \phi) = -\frac{1}{\mu} \frac{\partial A_z}{\partial \rho} = H_n(\rho) e^{-jn\phi} \tag{3.65}$$

where $$H_n(\rho) = -\frac{\gamma_n'}{\mu} [a_1 I_n'(\gamma_n' \rho) - a_2 K_n'(\gamma_n' \rho)] \tag{3.66}$$

or when $\sigma=0$, $$H_n(\rho) = -\frac{n}{\rho} [a_1 \rho^n - a_2 \rho^{-n}] \tag{3.67}$$

Therefore, plugging Equations 3.62 and 3.65 into Equation 3.61 we can conclude that $$R_n(\rho, \phi) = R_n(\rho) = \frac{\rho}{n} \frac{H_n(\rho)}{A_n(\rho)} \tag{3.68}$$

It is useful to first determine how $R_n(\rho)$ behaves at the first and last material interfaces, at $\rho=\rho_0$ and $\rho=\rho_{N-1}$ respectively, as shown in FIG. 24. In the innermost material layer which contains $\rho=0$, it is necessary for $a_2=0$, as K diverges at $\rho=0$ Therefore, at the innermost material interface $$R_n(\rho_0) = -\frac{\rho \gamma_{n'}}{\mu n} \frac{I_n'(\gamma_{n'} \rho_0)}{I_n(\gamma_{n'} \rho_0)} \tag{3.69}$$

or when $\sigma=0$, simply $$R_n(\rho_0) = -\frac{1}{\mu} \tag{3.70}$$

Note that in this case, $R_n$ has the opposite sign as compared to the analagous Cartesian and circumferential-drive cylindrical cases. This is because when the roles of $\rho$ and $\phi$ in the coordinate system are swapped, the right-hand rule requires that the normal component of the magnetic flux points in the opposite direction.

In the outermost layer which contains $\rho=\infty$, I diverges as $\rho \to \infty$, so we can immediately say that $a_1=0$ Therefore, at the outermost material interface $$R_n(\rho_{N-1}) = \frac{\rho \gamma_{n'}}{\mu n} \frac{K_n'(\gamma_{n'} \rho_0)}{K_n(\gamma_{n'} \rho_0)} \tag{3.71}$$

or when $\sigma=0$, simply $$R_n(\rho_{N-1}) = \frac{1}{\mu} \tag{3.72}$$

Once again we want a transfer function that relates $R_n(\rho_i)$ at one interface of a layer of thickness t to the interface on the other side of the layer at $R_n(\rho_{i+1}) = R_n(\rho_i + t)$. This would make it possible to begin at the innermost and outermost layer, apply the transfer function across each layer consecutively, and end up with an expression for the surface reluctance density on either side of the plane of the sensor, $R_n(\rho_s^+)$ and $R_n(\rho_s^-)$. The difference between these two quantities, defined as $R_n$, can then be related back to the wavenumber mode of the surface current density in the plane of the windings, $K_S$, as follows:

$$R_n = R_n(\rho_s^+) - R_n(\rho_s^-) = \frac{\rho}{n} \frac{H_{\phi_n}(\rho_s^+, \phi) - H_{\phi_n}(\rho_s^-, \phi)}{A_{z_n}(\rho_s, \phi)} = \frac{\rho}{n} \frac{K_{S_n}}{A_n(\rho_s)} \tag{3.73}$$

where $$K_S(\phi) = \sum_{n=-\infty}^{\infty} K_{S_n} e^{-jn\phi} \tag{3.74}$$

This transfer relation can be derived from the analagous equation to Equation 25 in Section 2.16 of [4] which formulates the magnetic vector potential everwhere in a layer in terms of its value at the two interfaces of the layer which are at $\rho=\rho_i$ and $\rho=\rho_i+t$:

$$A_n(\rho) = A_n(\rho_i)\frac{I_n(\gamma_{n'}(\rho_i+t))K_n(\gamma_{n'}\rho) - K_n(\gamma_{n'}(\rho_i+t))I_n(\gamma_{n'}\rho)}{I_n(\gamma_{n'}(\rho_i+t))K_n(\gamma_{n'}\rho_i) - K_n(\gamma_{n'}(\rho_i+t))I_n(\gamma_{n'}\rho_i)} - \tag{3.75}$$
$$A_n(\rho_i+t)\frac{I_n(\gamma_{n'}\rho_i)K_n(\gamma_{n'}\rho) - K_n(\gamma_{n'}\rho_i)I_n(\gamma_{n'}\rho)}{I_n(\gamma_{n'}(\rho_i+t))K_n(\gamma_{n'}\rho_i) - K_n(\gamma_{n'}(\rho_i+t))I_n(\gamma_{n'}\rho_i)}$$

We can see that this equation must be true as both $I_n(\gamma_n\rho)$ and $K_n(\gamma_n\rho)$ satisfy Equation 3.52 and it is self-consistent at the two interfaces of the layer. Using Equations 3.65, 3.68, and 3.75, we can formulate the following equations for the surface inductance density at the two interface layers:

$$R_n(\rho_i) = \tag{3.76}$$
$$\frac{\rho\gamma_{n'}}{\mu n}\frac{I_n(\gamma_{n'}(\rho_i+t))K'_n(\gamma_{n'}\rho_i) + K_n(\gamma_{n'}(\rho_i+t))I'_n(\gamma_{n'}\rho_i)}{I_n(\gamma_{n'}(\rho_i+t))K_n(\gamma_{n'}\rho_i) - K_n(\gamma_{n'}(\rho_i+t))I_n(\gamma_{n'}\rho_i)} - \frac{\rho\gamma_{n'}}{\mu n}$$
$$\frac{I_n(\gamma_{n'}\rho_i)K'_n(\gamma_{n'}\rho_i) + K_n(\gamma_{n'}\rho_i)I'_n(\gamma_{n'}\rho_i)}{I_n(\gamma_{n'}(\rho_i+t))K_n(\gamma_{n'}\rho_i) - K_n(\gamma_{n'}(\rho_i+t))I_n(\gamma_{n'}\rho_i)} \frac{A_n(\rho_i+t)}{A_n(\rho_i)}$$

$$R_n(\rho_i+t) = \frac{\rho\gamma_{n'}}{\mu n} \tag{3.77}$$
$$I_n(\gamma_{n'}(\rho_i+t))K'_n(\gamma_{n'}(\rho_i+t)) +$$
$$\frac{K_n(\gamma_{n'}(\rho_i+t))I'_n(\gamma_{n'}(\rho_i+t))}{I_n(\gamma_{n'}(\rho_i+t))K_n(\gamma_{n'}\rho_i) - K_n(\gamma_{n'}(\rho_i+t))I_n(\gamma_{n'}\rho_i)}\frac{A_n(\rho_i)}{A_n(\rho_i+t)} -$$
$$\frac{\rho\gamma_{n'}}{\mu n}\frac{I_n(\gamma_{n'}\rho_i)K'_n(\gamma_{n'}(\rho_i+t)) + K_n(\gamma_{n'}\rho_i)I'_n(\gamma_{n'}(\rho_i+t))}{I_n(\gamma_{n'}(\rho_i+t))K_n(\gamma_{n'}\rho_i) - K_n(\gamma_{n'}(\rho_i+t))I_n(\gamma_{n'}\rho_i)}$$

Finally, we can combine Equations 3.76 and 3.77, eliminating $A_n$ from the expression, leaving us with a transfer function that relates the surface reluctance density at one layer's interface to the next.

$$R_n(\rho_i+t) = G_n(\rho_i+t) + F_n(\rho_i+t)\frac{G_n(\rho_i)}{R_n(\rho_i) - F_n(\rho_i)} \tag{3.78}$$

where $$F_n(x) = \frac{x\gamma_{n'}}{\mu^*n}\frac{I_n(\gamma_{n'}(\rho_i+t))K'_n(\gamma_{n'}x) + K_n(\gamma_{n'}(\rho_i+t))I'_n(\gamma_{n'}x)}{I_n(\gamma_{n'}(\rho_i+t))K_n(\gamma_{n'}\rho_i) - K_n(\gamma_{n'}(\rho_i+t))I_n(\gamma_{n'}\rho_i)} \tag{3.79}$$

$$G_n(x) = -\frac{x\gamma_{n'}}{\mu^*n}\frac{I_n(\gamma_{n'}\rho_i)K'_n(\gamma_{n'}x) + K_n(\gamma_{n'}\rho_i)I'_n(\gamma_{n'}x)}{I_n(\gamma_{n'}(\rho_i+t))K_n(\gamma_{n'}\rho_i) - K_n(\gamma_{n'}(\rho_i+t))I_n(\gamma_{n'}\rho_i)} \tag{3.80}$$

For the case when $\sigma=0$, $$R_n(\rho_i+t) = \frac{1}{\mu}\frac{1 - \mu R_n(\rho_i)F_n\left(\frac{\rho_i+t}{\rho_i}\right)}{\mu R_n(\rho_i) - F_n\left(\frac{\rho_i+t}{\rho_i}\right)} \tag{3.81}$$

where $$F_n(x) = \frac{x^n + x^{-n}}{x^n - x^{-n}} \tag{3.82}$$

3.3.5 Implementation and Validation

The implementation procedure for this model parallels the previous model:

1. Define the current density in the primary windings based on knowledge of the sensor geometry and winding position and using the uniform current density assumption discussed earlier. Take the Fourier transform of the current density profile to determine the wavenumber modes of the surface current density.
2. For each wavemode, start at the innermost and outermost material interface and apply the transfer functions defined in Section 3.4 to determine the surface reluctance density on either side of the plane of the primary windings.
3. Calculate the magnetic vector potential in the plane of the primary windings for each wavenumber mode using Equation 3.73. Convert this to the magnetic vector potential in the plane of the sense element using Equation 3.75.
4. Calculate the magnetic field for each wavemode at the sense element using Equation 3.56.
5. Sum the magnetic fields due to each wavemode to determine the total magnetic field at the sense element due to a unit current excitation.

Since the procedure and equations are similar, the numerical implementation in Matlab has many of the same issues. Because of some of the extra terms in Equations 3.56, 3.75, 3.79, and 3.80, the efficient treatment of the Bessel functions is extra important. Taking into consideration the assymptotic nature of the modified Bessel function as their argument gets large [6] saves much simulation time. This is the equivalent of using the Cartesian coordinate model for large $\rho$.

The sensor shown in FIG. 25 was used to validate this model. Because no scanner was available to validate that the required symmetries were maintained after the sensor was wrapped around a pipe in this orientation, much care had to be taken to assure that the sensor's geometry matched the assumptions of the model. Specifically, care had to be taken to make sure that the sense elements remain in the same cylindrical plane as the drive wires when wrapped around the pipe.

Figure 29:
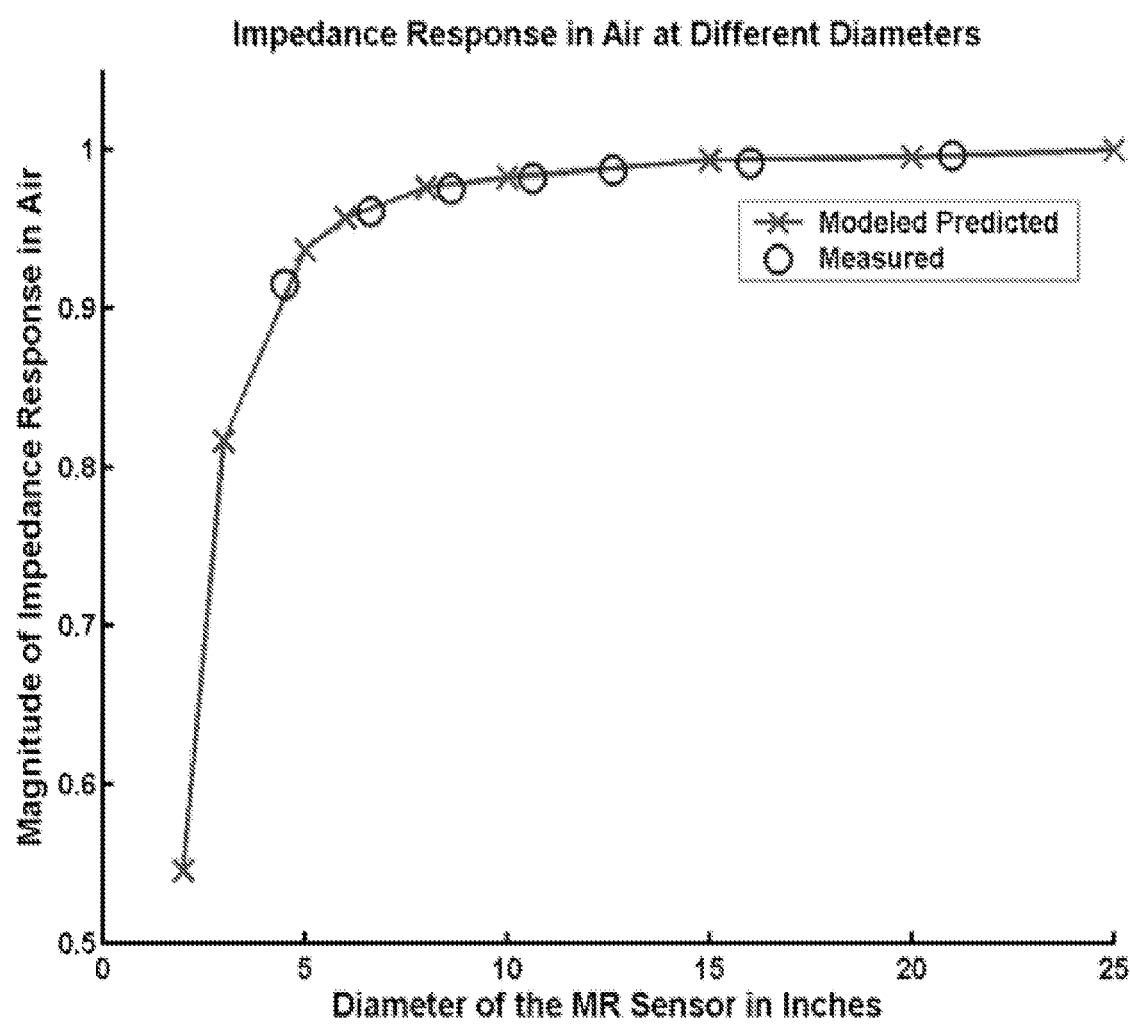
Figure 30:
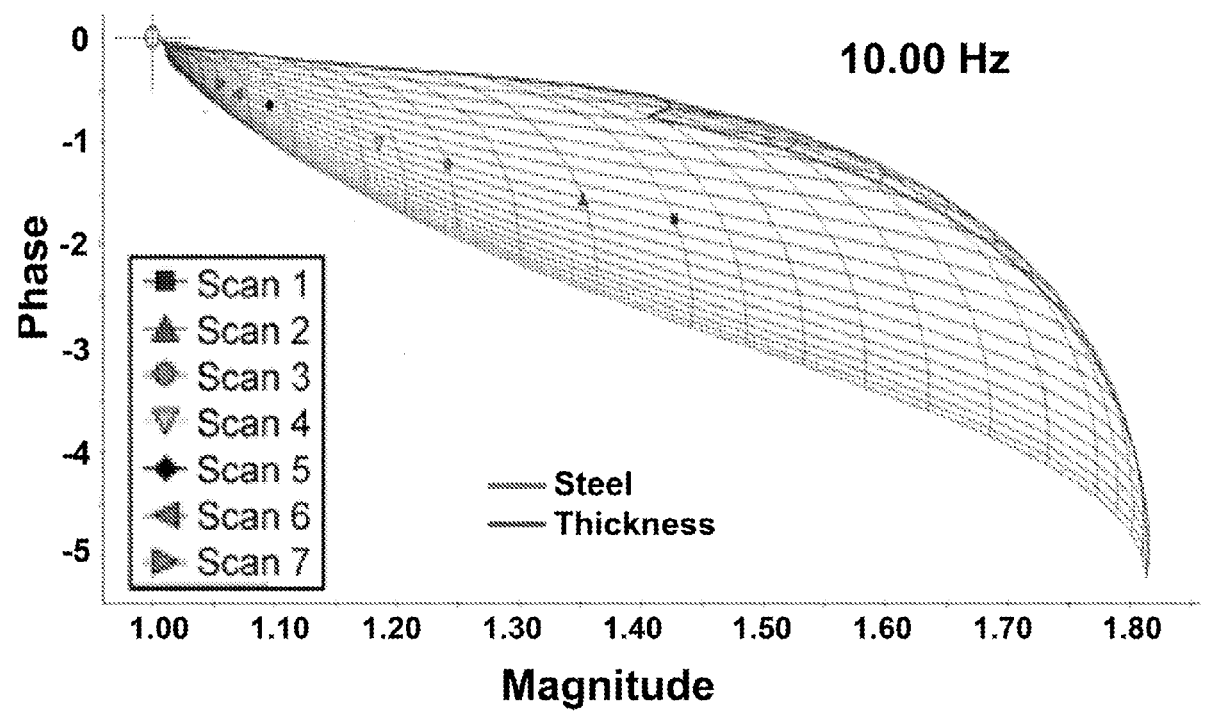

A similar measurement procedure was used to validate this model. FIG. 29 and FIG. 30 show the results that validated the cylindrical model implementation. FIG. 29 shows that the model successfully predicts the air responses of the sensor when wrapped around plastic cylinders of varying diameters. The response of the sensor in air when flat (before wrapping around the plastic cylinders) was normalized to 1+0 j. Only the magnitude of the impedance response is plotted as the phase was always zero. The RMS error of the measured air responses as compared to the model-predicted air responses is under 0.14%, which is within the tolerances of the experimental setup. FIG. 30 shows the results of taking measurements on a 6.625" diameter, 0.25" wall thickness pipe at varying lift-offs plotted on a lift-off/thickness grid. The air point represents the sensor's response in air when at a diameter of 10.625" (6.625" pipe+2" of insulation). The data follows the lift-off line up towards the air point. As the lift-off increased from 0.5" to 2.5", the estimated thickness varied only by ±0.004", with estimates ranging from 0.247" to 0.254".

SECTION REFERENCES

[1] N. J. Goldfine, "Uncalibrated, Absolute Property Estimation and Measurement Optimization for Conducting and Magnetic Media Using Imposed ω-k Magnetometry," Doctoral Thesis, Cataloged into the Massachusetts Institute of Technology Libraries, October 1992.
[2] Y. Sheiretov, "Deep Penetration Magnetoquasistatic Sensors," Doctoral Thesis, Cataloged into the Massachusetts Institute of Technology Libraries, June 2001.
[3] D. Schlicker, "Imaging of Absolute Electrical Properties Using Electroquasistatic and Magnetoquasistatic Sensor Arrays," Doctoral Thesis, Cataloged into the Massachusetts Institute of Technology Libraries, October 2005.
[4] H. Haus, J. Melcher, Electromagnetic Fields and Energy, Prentice-Hall Inc., New Jersey, 1989.
[5] F. Bowman, Introduction to Bessel Functions, Courier Dover Publications, 1958.
[6] F. Olver, L. Maximon, "Chapter 10: Bessel Functions," Digital Library of Mathematical Functions, http://dlmf-nist.gov/10, June 2013.
[7] ASTM Std E-2338
Section D-C: Calibration The inventors have recognized and appreciated the need for calibration, used in step 2001 and step 2007 of method 2000.

Sensor transimpedance data (Z) are obtained by applying a drive signal to the primary sensor winding. The resulting current in the primary winding (I) and voltage across the secondary winding (V) are measured and the transimpedance is calculated as the ratio of these two quantities, i.e., $$Z = V/I \qquad \text{Equation 1:}$$

It must be appreciated that all quantities discussed in this section are complex numbers, since in the sinusoidal steady state (SSS) regime, under which impedance analyzer 117 is operated, every signal is characterized by two values: a magnitude and a phase angle, or, equivalently, the real and imaginary components of a complex number.

In physical implementation, certain parasitic effects interfere with the ability of impedance analyzer 117 to measure V and I accurately. Therefore there is a need for a method to obtain Z from $I_m$ and $V_m$, which are the measured values of I and V, respectively.

The parasitic effects can be grouped in one of three classes, depending on how they contribute to the measured quantities.

Class 1: Scale factor. A number of different phenomena manifest themselves as scaling of the signal, i.e., multiplication of the voltage and/or current measurement by a complex number. For example, the instrumentation electronics have an overall gain and phase shift. As another example, the same model can be used for sensors that differ only in the length or number of secondary components, resulting in different multiplicative factors for each sensor. Cables can also introduce scaling and phase shift due to losses and to unmodeled capacitance or inductance of the cable. Since the scaling factor is a complex number, it can represent both scaling of the magnitude and changes in the phase of the signal.

Class 2: Parasitic coupling. Some of the measured voltage is the result of effects other than those due to the transimpedance of the sensor. For example, voltage can be induced in the secondary winding leads by the magnetic field of the drive winding or its leads. Furthermore, electronic components of the drive and sense electronics are located in close proximity and can couple to each other. This parasitic contribution to the voltage signal is proportional to the current I through the sensor. Note that it is theoretically possible to have parasitic voltage that is independent of I, or proportional to $I_m$ rather than I. Such effects are not observed in practice and are not addressed by this method.

Class 3: Parasitic current. The electronic components that measure the current can have a parasitic component, i.e., output a non-zero value even when the current though the sensor is zero. This is again due to non-ideal behavior of electronic components.

The parasitic effects can be represented by Equation 2 and Equation 3.

$$I_m = I + I_p \qquad \text{Equation 2}$$

$$V_m = \frac{1}{K}(ZI + Z_p I) \qquad \text{Equation 3}$$

In Equation 3, Class 1 effects are represented by the scaling factor 1/K. Class 2 parasitic coupling is represented by transimpedance $Z_p$. In Equation 2, Class 3 effects are represented by the parasitic current $I_p$. Equations 1, 2, and 3 are combined to obtain Equation 4 that is used to obtain Z from $I_m$ and $V_m$.

$$Z = K\left(\frac{V_m}{I_m - I_p}\right) - Z_p \qquad \text{Equation 4}$$

Figure 31:
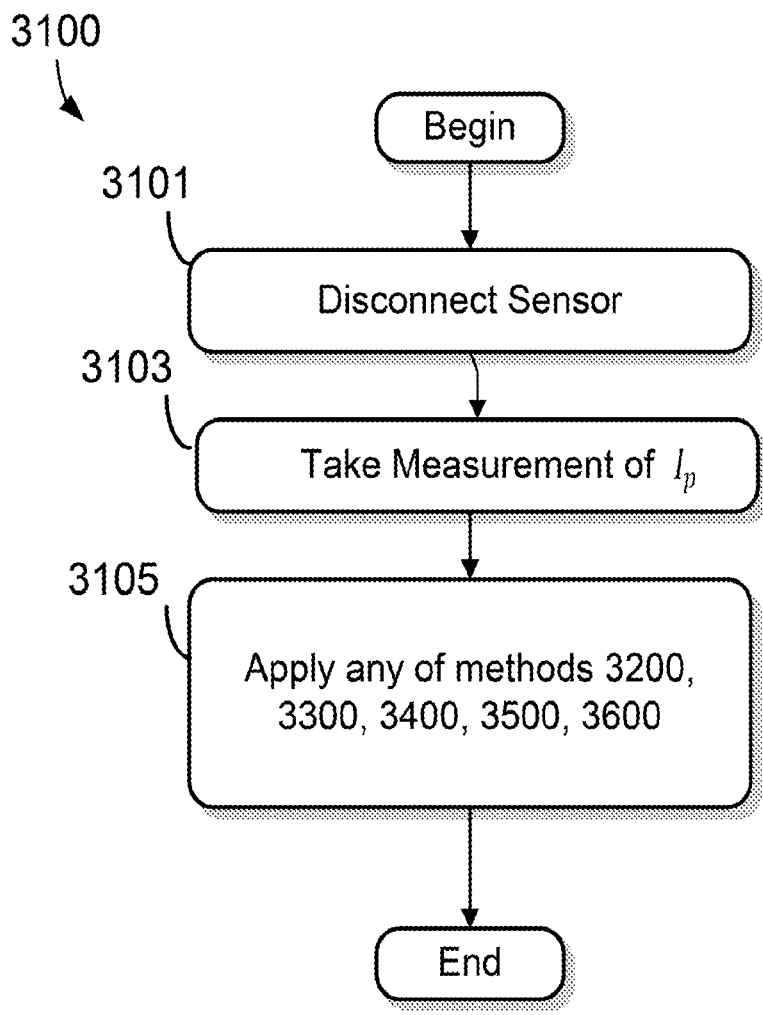

The calibration method constitutes application of Equation 4 to raw impedance data. It is therefore necessary to obtain the values of the three parameters K, $Z_p$, and $I_p$. This is accomplished using Method 3100 in FIG. 31.

To obtain the parasitic current $I_p$, a measurement is taken with the sensor disconnected. In this case the parasitic current $I_p$ is equal to the measured current $I_m$. This is accomplished in steps 3101 and 3103. Step 3105 is used to obtain K and $Z_p$. There are several possible methods for carrying out step 3105. These are methods 3200, 3300, 3400, 3500, and &3600, illustrated in FIG. 32, FIG. 33, FIG. 34, FIG. 35, and FIG. 36, respectively. Though, other suitable methods may be used in step 3105. The choice between these methods depends on the application.

It must be appreciated that if parasitic current $I_p$ is zero, or if the effect is ignored, then steps 3101 and 3103 of method 3100 may be omitted.

Methods 3200, 3300, 3400, 3500, and 3600 contain steps where measurements are taken in different configurations. The outcomes of these measurements are used by subsequent steps and are represented as transimpedance values $Z_m$ defined in Equation 5.

$$Z_m = \frac{V_m}{I_m - I_p} \qquad \text{Equation 5}$$

With this definition, Equation 4 can be written as Equation 6.

$$Z = KZ_m - Z_p \qquad \text{Equation 6:}$$

Methods 3200, 3300, 3400, 3500, and 3600 contain steps where simulated impedance values, a.k.a. precomputed sensor responses, are obtained from an analytical model, which computes the sensor's transimpedance in air ($Z_a$) or on reference materials ($Z_r$), as indicated in the flow charts. These precomputed sensor responses can be obtained by interpolating into a precomputed sensor database (PDB), or by direct application of the model. Since the methods can incorporate more than one measurement or simulation, numerical subscripts will be used to differentiate between them.

Figure 32:
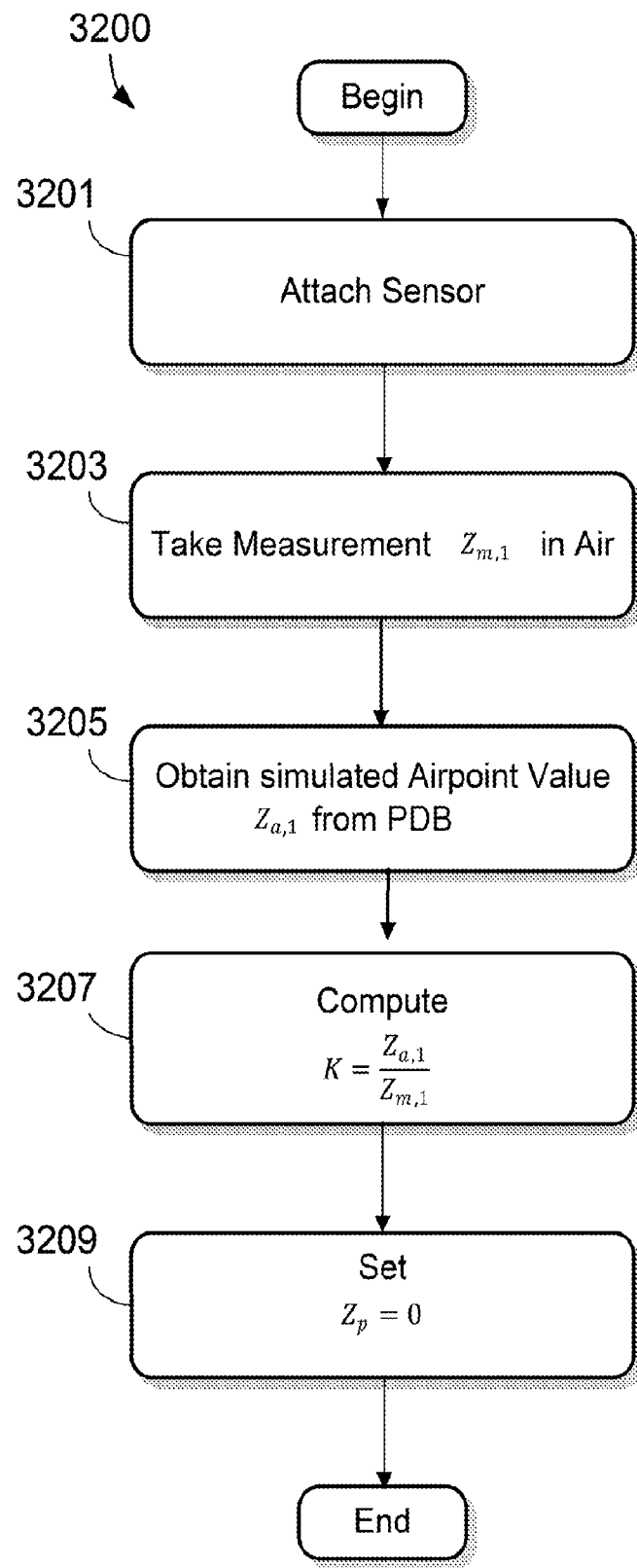

Method 3200, Air Calibration, is illustrated in FIG. 32. In this method a single data point is taken with the sensor in air. Since one measurement does not provide enough information to compute two parameters, only K is computed and the parasitic impedance $Z_p$ is set to zero. This method is appropriate when $Z_p$ is known to be negligible. The CUI application uses this method. Equations 7 and 8 are used by Method 3200.

$$K = \frac{Z_{a,1}}{Z_{m,1}} \quad \text{Equation 7}$$

$$Z_p = 0 \quad \text{Equation 8}$$

Figure 33:
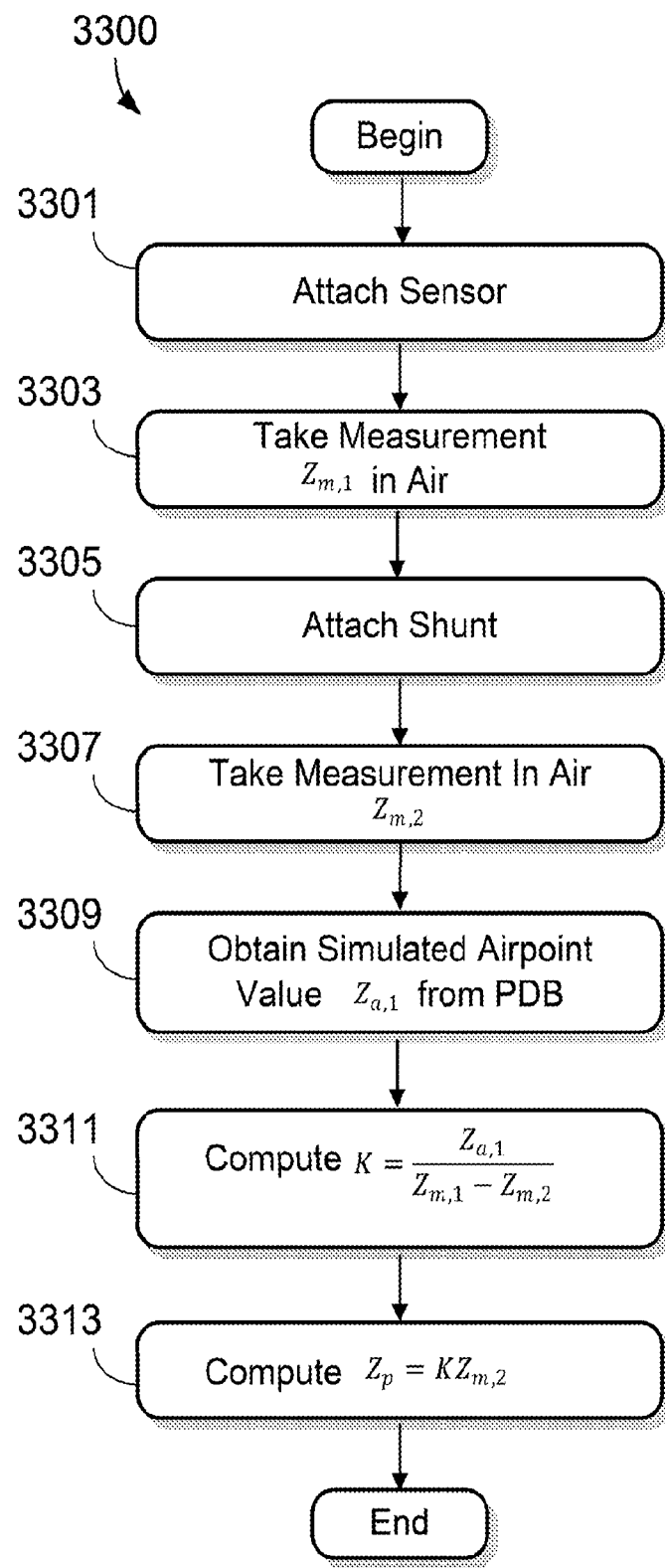

Method 3300, Air/Shunt Calibration, is illustrated in FIG. 33. In addition to a measurement with the sensor in air, this method also includes a measurement in air with a "shunt", which is a construct identical to the sensor except that the secondary windings are not connected to the leads. Under these circumstances the transimpedance Z is zero, effectively allowing for a direct measurement of $Z_p$, which is a scaled version of the impedance measured with the shunt. Equations 9 and 10 are used by Method 3300.

$$K = \frac{Z_{a,1}}{Z_{m,1} - Z_{m,2}} \quad \text{Equation 9}$$

$$Z_p = K Z_{m,2} \quad \text{Equation 10}$$

Figure 34:
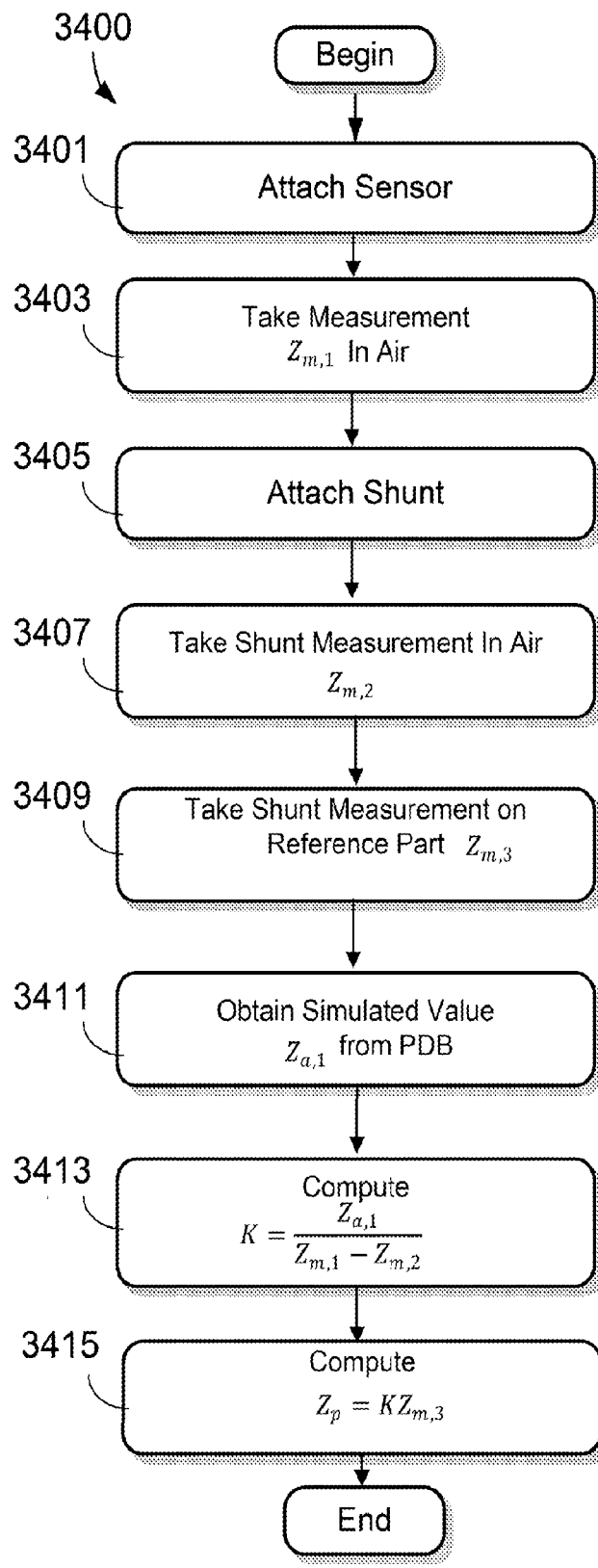
Figure 35:
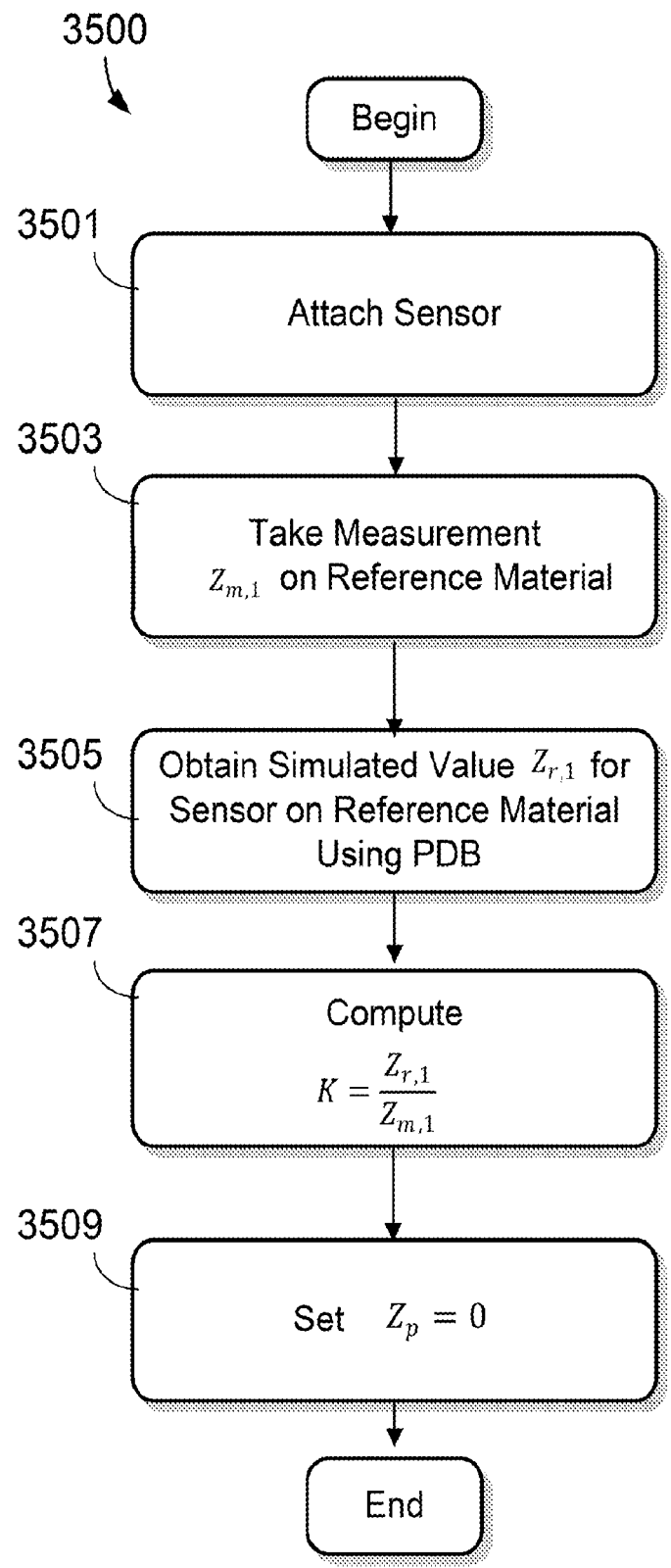

Method 3400, Air/Shunt/Shunt-on-Part Calibration, is illustrated in FIG. 34. This is a variation of Method &501. K is calculated in the same way using data from the first two measurements. A third measurement step is added, with the shunt placed on the object under test. The parasitic impedance $Z_p$ is calculated using data from this third measurement. This method is appropriate in situations where $Z_p$ is affected by the presence of the object under test. Therefore, one shunt measurement in air is needed as part of determining K, and one shunt measurement on the part is needed to determine $Z_p$ in the presence of the object under test. Equations 9 and 11 are used by Method 3400.

$$Z_p = K Z_{m,3} \quad \text{Equation 11:}$$

Figure 38:
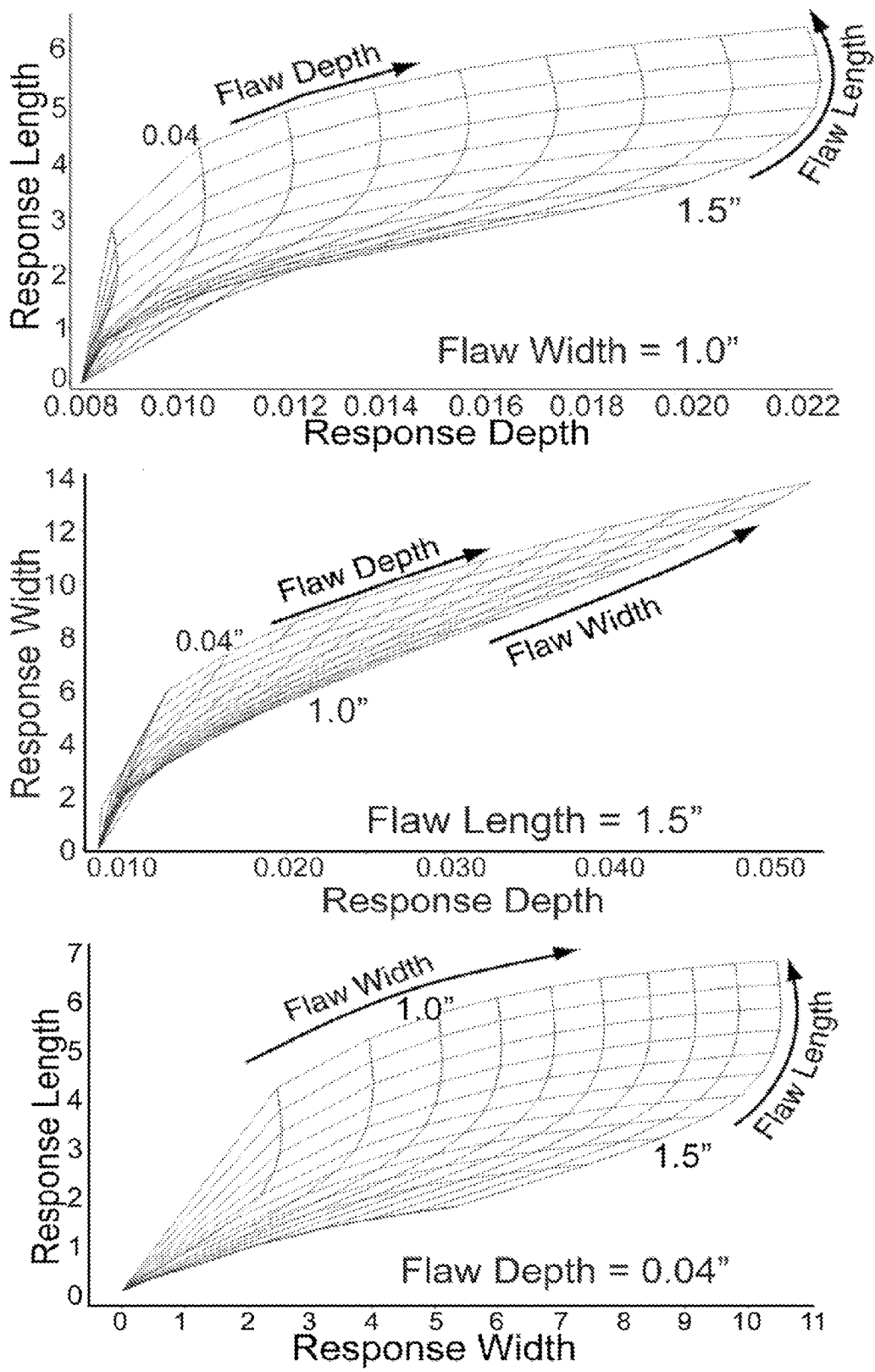

Method 3500, Single-Part Reference Calibration, is illustrated in FIG. 38. This is a variation of Method 3200, but instead of a measurement in air, the measurement is taken on a reference material or object, whose properties are expected to be similar to the test object. As in Method 3200, the parasitic impedance $Z_p$ is set to zero. For example, this method can be used in situations where the sensor cannot easily be removed from the scanning fixture. Equations 8 and 12 are used by Method 3500.

$$K = \frac{Z_{r,1}}{Z_{m,1}} \quad \text{Equation 12}$$

Figure 36:
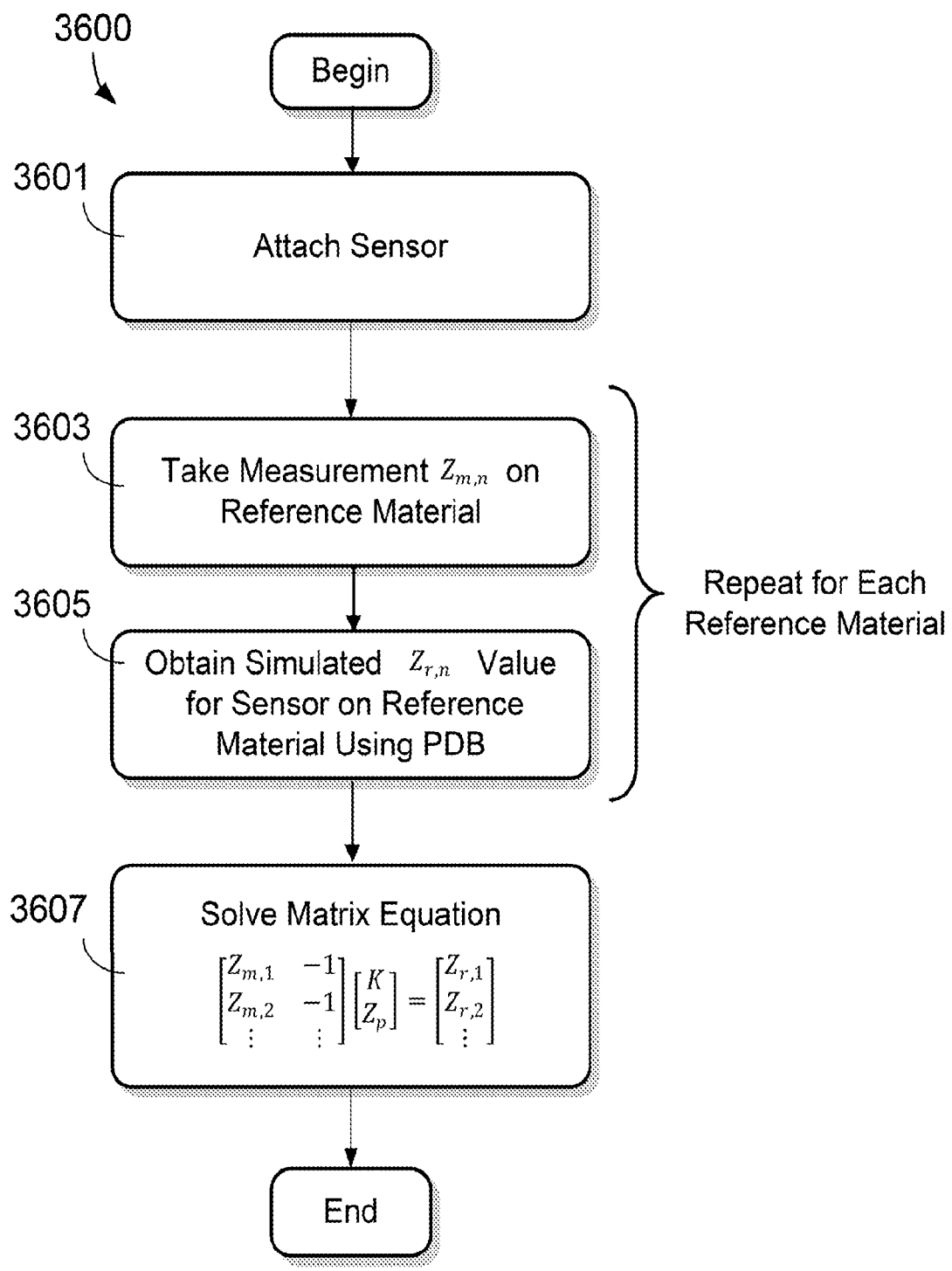

Method 3600, Reference Calibration, is illustrated in FIG. 36. Rather than obtaining $Z_p$ from a shunt measurement, as was done in methods 3300 and 3400, in this method $Z_p$ is computed indirectly, simultaneously with K, from measurement data with the sensor on two or more different reference material systems. Equation 6 is used once for each measurement, resulting in the matrix equation 13.

$$\begin{bmatrix} Z_{m,1} & -1 \\ Z_{m,2} & -1 \\ \vdots & \vdots \end{bmatrix} \begin{bmatrix} K \\ Z_p \end{bmatrix} = \begin{bmatrix} Z_{r,1} \\ Z_{r,2} \\ \vdots \end{bmatrix} \quad \text{Equation 13}$$

K and $Z_p$ are obtained by solving the matrix equation 7. Note that if more than two reference measurements are used, Equation 13 will not, in general, have an exact solution, in which case it must be solved in the least-squares sense, where the error is minimized.

Note that the two or more reference systems may differ only in the lift-off, i.e., the distance between the sensor and the reference material. In one embodiment, "shims", i.e., magnetically inert films of a known thickness, are used to provide a different lift-off for each reference measurement.

When calibration data on reference material systems is taken, to be used in methods 3200, 3300, 3400, 3500, and 3600, it is necessary that the reference systems be constructed in a way that matches the assumptions used by the analytical model. Specifically, if the model assumes a cylindrical geometry, e.g., for CUI measurements on pipes, then when the calibration data is taken in air, the sensor must be bent to follow a cylindrical surface with a radius matching the radius of the sensor when it is used on the pipe. Whereas it is possible to use a flat surface and a corresponding flat surface model to obtain calibration parameters, more accurate calibration will be achieved when the same sensor configuration is used to obtain calibration and measurement data.

Flaw Sizing

While the double-rectangular sensor design provides a more representative flaw response with minimal impact from unmodeled effects, the resulting response is still a "blurred" image of the actual flaw. Hence, the MR-MWM-Array approach to CUI requires an algorithm to provide accurate sizing information for detected flaws. The following describes Method DDD and demonstrates its successful implementation.

Proposed Lattice Approach for Flaw Sizing

By taking the computed footprints generated in the previous chapter and convolving them with simulated defects of various sizes, we can create a multidimensional database that can be used along with JENTEK's multivariate inverse methods, also known as grid methods, to produce flaw sizing estimates. JENTEK's grid methods are typically used to convert multifrequency transimpedance measurements into absolute material properties: for each frequency measured, the real and imaginary components of the impedance response provide two equations. Given sufficient selectivity (independent equations are provided by the multifrequency impedance data), n frequencies allow for the estimation of $2^n$ properties. The sensitivity and selectivity of a measurement can be analyzed using singular value decomposition of the Jacobian matrix [N. J. Goldfine, "Magnetometers for Improved Materials Characterization in Aerospace Applications," Materials Evaluation, vol. 51, no. 3, pp. 396, March 1993].

It is necessary to find a set of observable measurement characteristics that can be used to correlate to the flaw characteristics of interest. Since flaws can come in all shapes and depth profiles, assumptions need to be made about observed flaws. If each flaw is assumed to be discrete and of uniform depth over a rectangular area, then the flaw characteristics to be measured are well defined: length, width and depth. Therefore, it is necessary to determine three observable measurement characteristics for each flaw.

Length is defined to be in the circumferential direction of the pipeline and width is defined to be in the axial direction of the pipeline. Length and width can also be characterized relative to the sensor; length is in the channel direction and width is in the scan direction.

The proposed measurement characteristics can be determined using the following procedure for Method DDD:

Apply a threshold to the thickness image to identify the location of discrete flaws.

Determine the location of each discrete flaw and an estimated length and width of the response that exceeds the threshold.

Within the area of the flaw, determine the maximum flaw response.

Using this procedure, the generated flaw sizing lattice has three inputs and three outputs. The inputs are flaw response length and width below a given threshold, and maximum flaw depth. The outputs are estimated flaw length, width and uniform depth.

Lattice Generation and Orthogonality

In order to prove the validity of Method DDD, it is necessary to first generate a test lattice with sufficient sensitivity and selectivity to generate reliable flaw characteristic estimates given measured observations. For the following discussion, the inputs to the lattice, dependent variables in the forward model (measured signal width, length and uniform depth), will be referred to as signal characteristics, and the outputs of the lattice, independent variables in the forward model (estimated flaw width, length and uniform depth), will be referred to as flaw characteristics.

Sensitivity measures the resulting change in flaw characteristics due to small changes in signal characteristics. Low sensitivity (i.e. very large changes in flaw characteristic due to a perturbation) can result in a very unreliable measurement. A lattice's selectivity reflects the independence of the lattice's output parameters. A low selectivity lattice results in the lattice being multivalued (a set of measurement characteristics corresponding to more than one possible set of flaw characteristics) which causes the multivariate inverse method search algorithm to fail.

The sensitivity and selectivity of the lattice can be evaluated by visualizing the three-dimensional lattice in multiple two-dimensional slices. This is shown in FIG. 38 for a aflaw sizing lattice generated with an 0.015" threshold using the footprint generated by Method CCC for the sensor pictured in FIG. 43. The nominal pipe diameter was 6.625" and the pipe wall was 0.280" (this is a standard 6" schedule 40 pipe size). The flaws were assumed to be internal flaws, although the lattice change is minimal when external flaws are considered.

The selectivity of the lattice can be evaluated by looking at the lines of constant flaw characteristic property and looking to see if they are close to orthogonal to the other lines of constant flaw characteristic property (for example, seeing if a line of constant flaw length and width while varying depth is orthogonal to lines of constant flaw length and depth while varying width). If the lines are close to being parallel, then there is low selectivity and the nonlinear search algorithm will be unstable. In all three grid slices that are displayed in FIG. 38, the selectivity above a flaw width of 1", length of 1.5" and flaw depth of 0.040" should be sufficient for successful implementation.

Sensitivity can be determined by the size of the grid cells seen in the three slices displayed in FIG. 38. Again, the sensitivity seems acceptable above the same flaw sizes determined to be sufficient for selectivity.

Below these selectivity and sensitivity limits, it is unlikely that the flaw sizing algorithm will be reliable. However, these limits show feasibility for the algorithm to be able to size flaws that meet the application requirements. Given acceptable sensitivity and selectivity, since the lattice is not overconstrained (the number of inputs and outputs are equal), it follows that if the observed sensor response falls within the lattice, then there may be a unique solution. Furthermore, while sizing may not be reliable for flaws smaller than the limits defined in this section, detection still will be possible.

It is interesting that the selectivity and sensitivity are acceptable at a lower width threshold than length threshold. This makes sense, though, if we keep in mind that the footprint in the length direction is much bigger for this sensor than in the width direction. Therefore, in the width direction we have more sensitivity to local defects and can resolve them at smaller sizes.

Furthermore, it makes sense that there is enough independence in the length, width and depth of the flaws given the observed length, width and maximum depth of the flaw response. Based on the method of convolution, we can intuit the relationship between the input parameters of the lattice and the output parameters. As the flaw width changes, we would expect the width of the response and the depth of the response to change significantly and the length of the response to change minimally. Likewise, as the length of the flaw changes, we would expect the length of the response and the depth of the response to change significantly while the width of the response changes minimally. And finally, if the depth of the flaw changes, we would expect all three response characteristics to change. These three relationships would appear to be independent.

While this visualization shows feasibility, the accuracy of the method is still in question. This is analyzed in the following section.

Finite Element Method (FEM) and Measurement Validation of Sizing Approach

Using the footprint convolution method for sizing requires a more stringent validation. The width, length and depth of a sensor's response must match the result of convolving the sensor's footprint with a simulated flaw to an accuracy that allows the multivariate inverse methods to effectively use the generated lattice.

Figure 43:
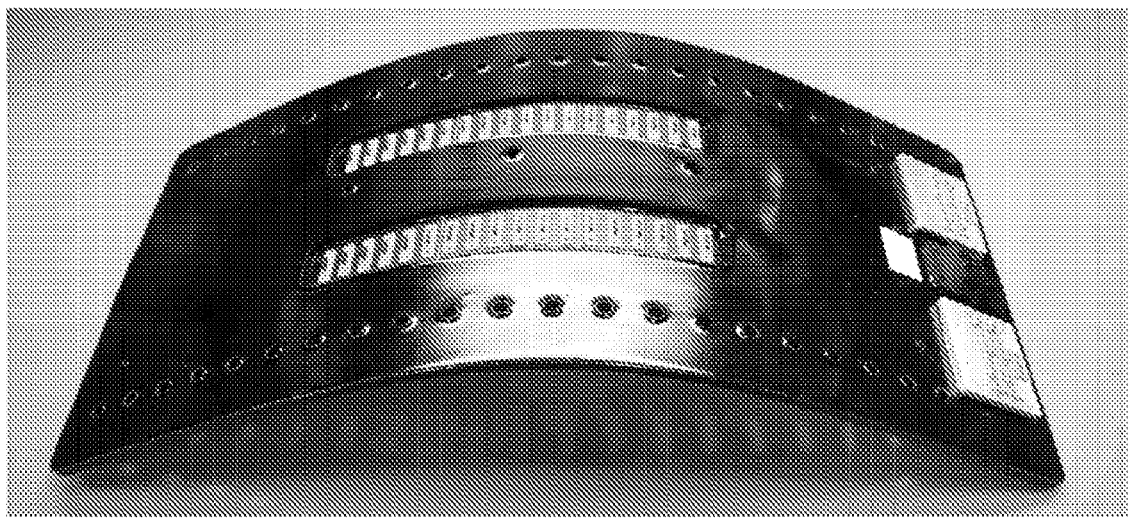

Since it is not practical (from both a cost and time perspective) to create a large number of sample flaws of varying sizes and depths, FEM simulation was used to predict the response of the sensor pictured in FIG. 43 to an array of flaw sizes and depths in flat steel plates 0.25" thick with 2" of lift-off. These simulations used the commercial package Faraday, a three-dimensional eddy current solver from Integrated Engineering Software. The boundary element method was used with this package to determine the magnetic field distributions since it does not require as much memory or processing time as finite element model packages. These simulations used a self-adaptive mesh with an accuracy setting 0.0003 to refine the mesh density for the computation in the areas where the fields were changing relatively rapidly and an accuracy/speed factor of 3. A smaller accuracy setting or a larger speed factor reduces the numerical error in the calculation at the expense of using more memory and a longer processing time; previous work had shown that settings that were used were reasonable for this geometry. Note that typically 2-8 GB of RAM were required for these simulations.

Because FEM simulations converge very slowly, simulating a scan over a single flaw would take nearly a month of computation time (15 minutes per measurement, 0.5 inch measurement spacing, 24 by 24 inch measurement grid, 8 flaw sizes, 10 flaw depths). A more practical use of FEM simulation for validating the footprint convolution sizing method is to simulate only the point of maximal response for each flaw. Since both the footprint model and initial measurements agree on the position for this maximal response this is a reasonable approach. 20 Hz was the simulation frequency.

Figure 39:
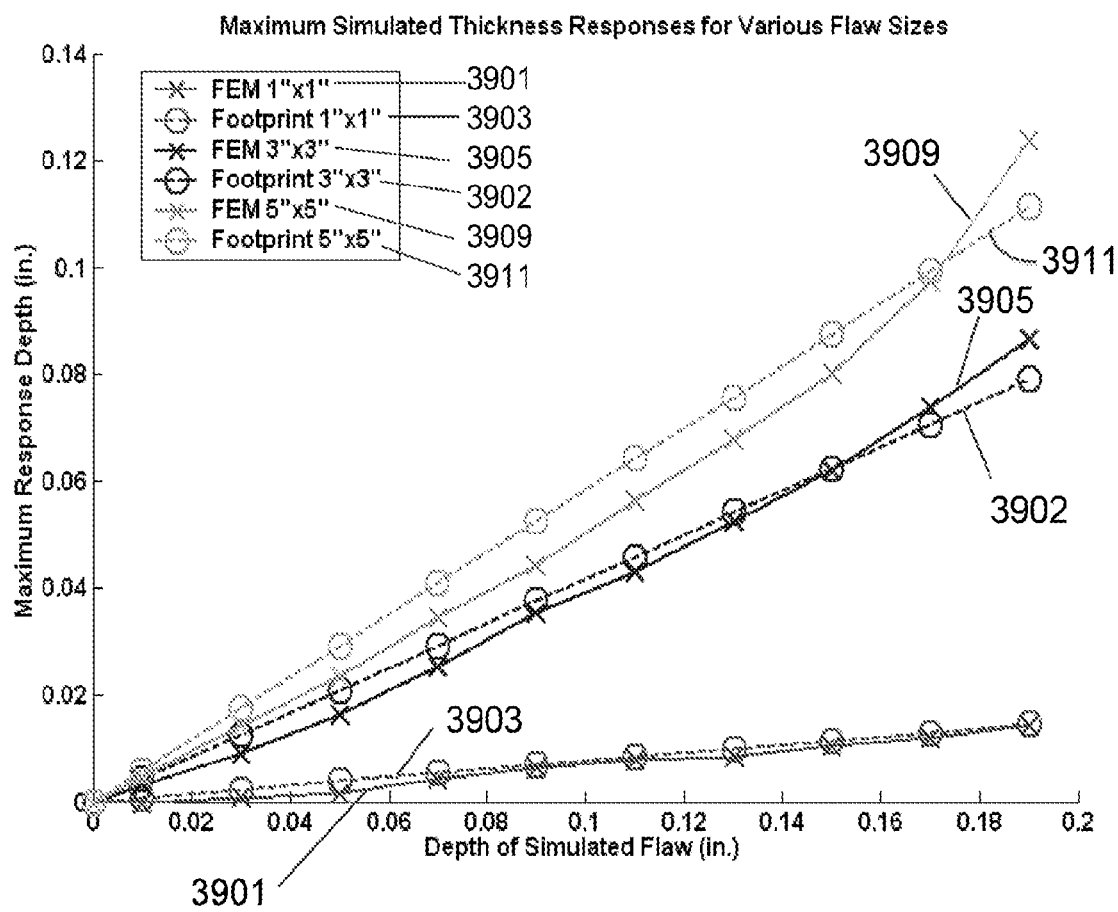
Figure 40:
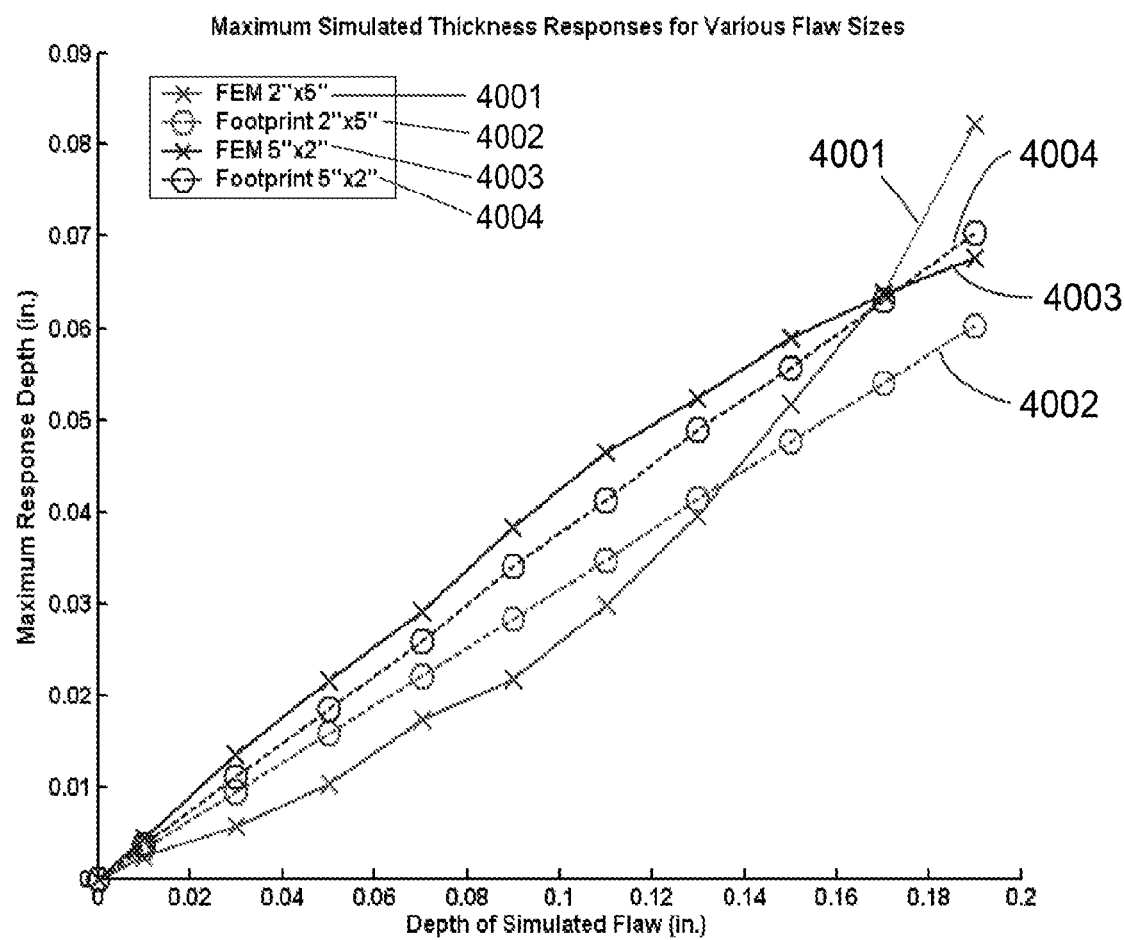

FIG. 39 and FIG. 40 summarize these results. What we see is good agreement between the simulated measurements and the footprint model convolution for flaws of varying sizes and aspect ratios: there is a linear relationship between flaw depth and response maximum, and the slope is determined by the area of the flaw. However, the linearity of the FEM simulations starts to break down for the small aspect ratio flaws with large depth. This is likely due to a numerical noise issue in the FEM simulation: it was difficult to get convergence in these cases.

Figure 41:
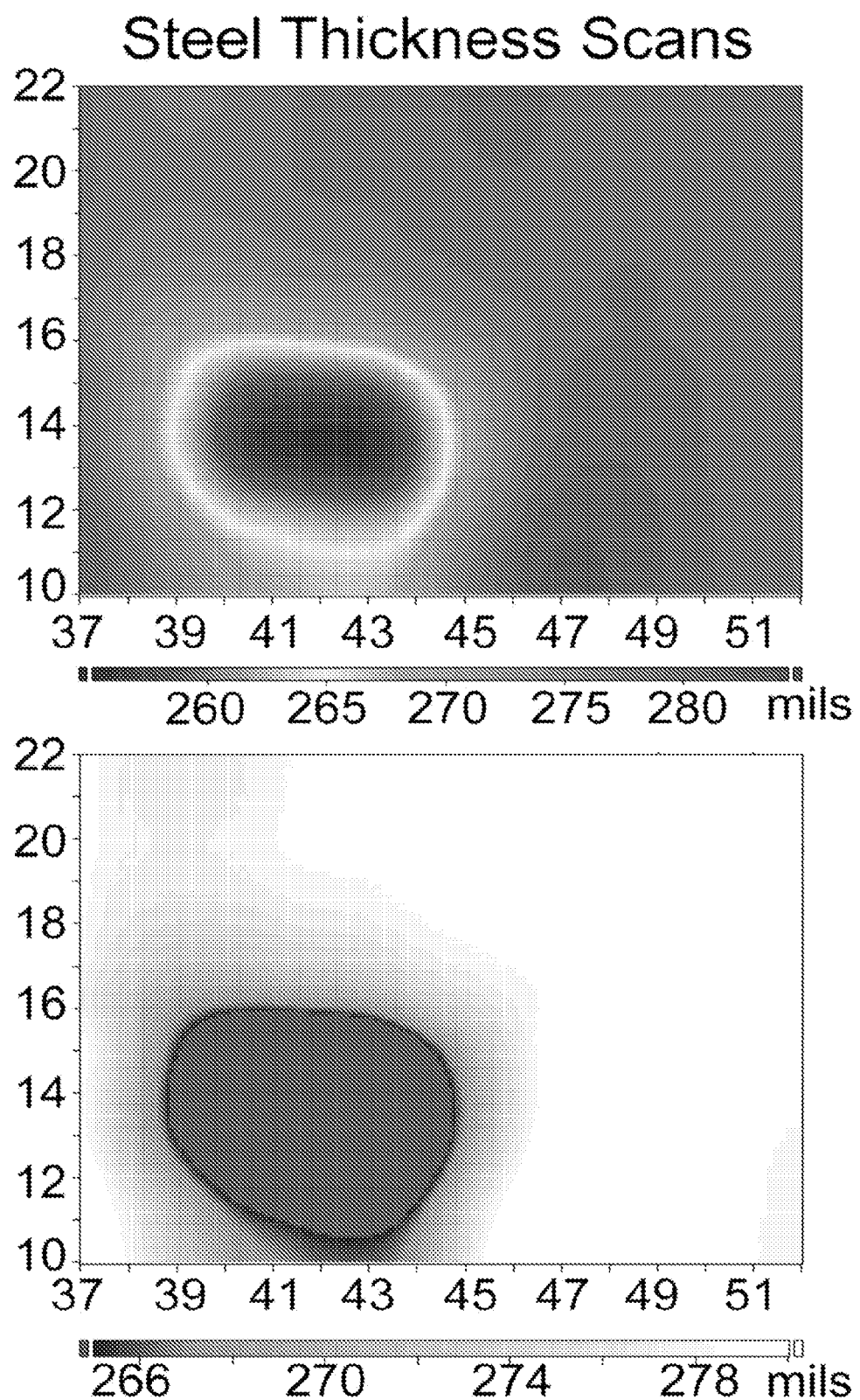

With demonstrated agreement between the models and the simulated measurements, and a lattice that has reasonable sensitivity and selectivity, the final verification step is to try to process actual measurements. A 4" long (circumferential), 6" wide (axial), 0.100" deep flaw in a 6.625" diameter, 0.280" thick pipe was scanned with 2" of insulation and standard weather jacketing. The flaw response, shown in FIG. 41 (left) was thresholded with a 0.015" threshold, and the thresholded image is shown in FIG. 41 (right). The flaw response had a measured length of 5.3", width of 5.9" and maximum depth of 0.0248". These numbers were processed through the footprint sizing lattice and the estimated flaw size was very reasonable. Perturbations were applied to the measurement responses to verify acceptable sensitivity and selectivity of the lattice. Small changes in response sizes resulted in acceptably small changes in flaw estimate size. These results are summarized in FIG. 42.

Section E: Applications

Section E-B: In-Line Inspection (ILI)

In-line inspection (ILI) devices are a type of tool configured for traveling inside of a pipe or pipeline. One type of ILI tool is configured to identify locations of pipe wall loss due to corrosion within a pipe based on the principles of magnetic flux leakage (MFL). These tools offer the state of the art performance for inspection of both liquid and gas pipelines using magnetic fields. However, they have many limitations. The MFL mode provides both internal and external corrosion imaging capability and very limited crack detection capability. Using a constant field produced by permanent magnets and an array of hall sensors located to provide circumferential coverage and to measure the magnetic field response at each circumferential location, a relatively high-resolution corrosion image is achieved as the tool travels axially down a pipeline. Recent advances include dual field modes implemented by Rosen, but similar to the dual spatial wavelength and segmented field methods described by Melcher and later by Goldfine respectively; the dual orientation methods, or single orientations (e.g., at 45 degrees) to detect both axial and circumferential cracks, implemented by TDW, but also previously introduced by many for other applications, including by Goldfine. The eddy current mode introduced over the last decade by many offers high resolution internal geometry mapping, but in the implemented format is limited by the eddy current winding construct, electronics architecture, and data analysis algorithms used.

Major limitations for the MFL mode include (1) the need for the magnets to provide near saturation level fields and therefore needing large and heavy magnets and introducing difficulties associated with large magnets, such as the potential to become lodged in the pipeline and variation in magnet strength, (2) poor modeling of the physics due to the inclusion of difficult to model field constructs resulting in difficult data interpretation, (3) relatively poor crack detection capability because of wide spacing of the hall sensors and the difficulty of detecting cracks (such as tight internally initiated cracks) with a constant field mode even with two orientations, (4) false indications caused by inconsequential magnetic anomalies in the material, and (5) poor defect sizing due to limited available information from the MFL mode even with dual orientations or dual field modes.

Poor defect sizing is alleviated slightly by the combined use of the eddy current and MFL modes, but due to the limits of the implemented eddy current mode, this is also limited. Conventional eddy current sensing methods used with MFL tools have many limitations including (1) loss of calibration with variations in magnetic permeability of the pipe wall because the lift-off line orientations vary with magnetic permeability, (2) inability to properly scale material loss anomalies or crack like features with lift-off due to curvature of lift-off lines and the inability to properly determine the lift-off value, (3) cross-talk between closely spaced coils, (4) variation of response for defects directly over a coil versus defects between coils, (5) difficulty modeling and predicting the sensor response for varied material under test conditions and operating conditions, such as temperature, due to the coil geometry selection, and (6) use of electronics that is switched between sensing elements and that does not enable simultaneous measurement of both impedance magnitude and phase (or real and imaginary part of the complex impedance, defined as the ratio of the sensing element voltage to the drive current). The last limitation introduces both coverage and data interpretation limitations that are severe for high speed tools.

Perhaps the biggest deficiency of both the MFL and conventional eddy current methods is the lack of reproducibility. Changes in the field strength or changes in the gap between the sensing elements and the wall or the magnets and the wall, as well as tilting and off-center positioning of the tool so that all sensing elements are not equal distance from the internal wall will produce variations in the MFL and conventional eddy current sensor responses. These variations make it difficult to compare runs from past inspections with the current inspection. It is common for service providers to find that corrosion defects appear to get smaller (a physical impossibility) using these currently available ILI tools.

Another major issue with ILI tools, including MFL tools, ultrasonic tools and more recent EMAT tools is their length and ability to be reduced in size for small diameter pipeline inspections. The length and weight of these tools requires relatively long and costly "pig launchers." The weight, length and complexity of these tools require substantial logistics support for transport and handling. Thus, these tools are typically run on a pipeline once every 3-6 years. It is not practical to run existing tools often, due to logistics costs, and repeated runs cannot be practically compared for MFL tools due to lack of repeatability, and many pipelines sections do not have the required pig launchers.

Having appreciated these deficiencies, the inventors provide a miniaturized electronics configuration that provides fully parallel sensing element electronics and support for multiple synchronized drive conductor segments, allowing simultaneous measurement of the real and imaginary part of the complex impedance on numerous channels.

Figure 44:
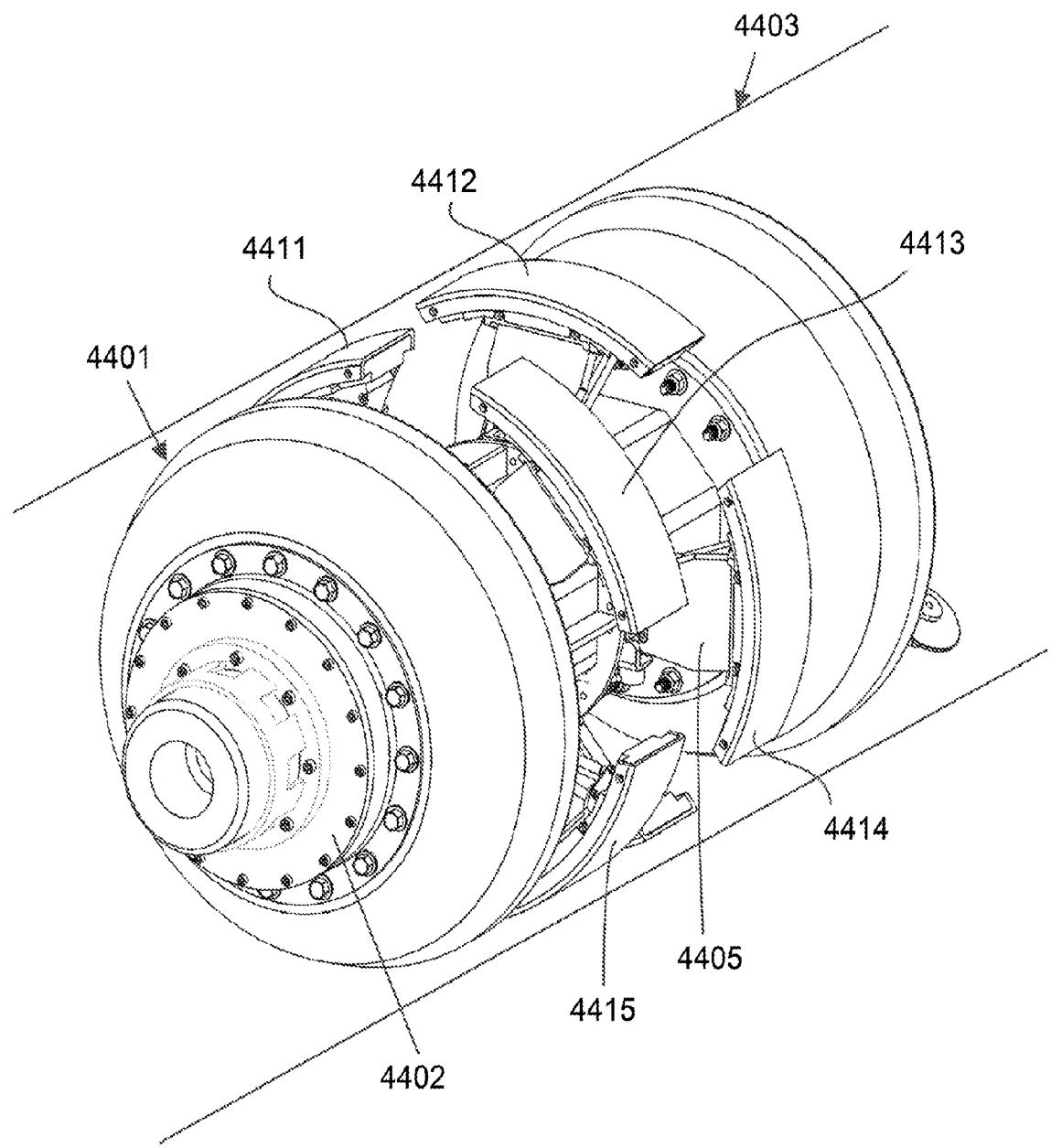

FIG. 44 shows an ILI tool 4401 within a pipe 4403 according to some embodiments. Tool 4401 includes a tool body 4402, with system electronics, a plurality of sensors 4411-4415, and support armatures 4405. In some embodiments sensors 4411-4415 include a drive winding with an arc-shaped segment. The arc-shaped segment may be curved to match the internal pipe diameter, but offset to account for the designed average gap between the arc the internal surface of the pipe wall. Each arc-shaped segment may include an independently driven drive winding and an array of sensing elements at a fixed distance from the drive. For example, an MWM®-Array sensor may be used. The drive winding may form a single rectangle, a dual rectangle configuration, or any other suitable drive winding configuration (see FIG. 3 of US Patent Publication No. 2013/0124109). Those of skill in the art will appreciate that tool size constraints, among other factors, may affect the selection of one drive winding configuration over another.

Using a dual rectangle drive construct, two rows of sensing elements may be incorporated into sensors 4411-4415 (one linear array within each of the two dual rectangles as shown in FIG. 3D of US Patent Publication No. 2013/0124109). A precomputed database of sensor responses, similar to that presented in Goldfine et al. (U.S. Pat. No. 5,629,621) and refined in subsequent patents, may be used to estimate the lift-off between each sensing element and the internal pipeline wall surface at each impedance measurement location, and the same precomputed database is used to estimate a second property of interest.

The second property of interest may be the magnetic permeability in the direction perpendicular to the drive segment. In some embodiments the arc-shaped drive winding segment is oriented circumferentially (similar to FIG. 3G of US Patent Publication No. 2013/0124109) to estimate the magnetic permeability in the axial direction. In another embodiment, the arc-shaped drive segment is oriented at an angle, such as 45 degrees, to enable detection of cracks in both the circumferential and axial orientation and the measurement of stress components in both the hoop (circumferential) and longitudinal (axial) directions.

Two rows of sensors 4411-4415 may be included to enable full coverage circumferentially and to allow the drive segment on each arc to extend beyond the last sensing element to improve the model accuracy for the models used to generate the precomputed databases. As illustrated in FIG. 44, sensors 4411, 4413, and 4415 form one row of sensors offset circumferentially from a second row formed by sensors 4412 and 4414. Of course, other sensors, not shown in FIG. 44, may be present to complete circumferential coverage.

Figure 45:
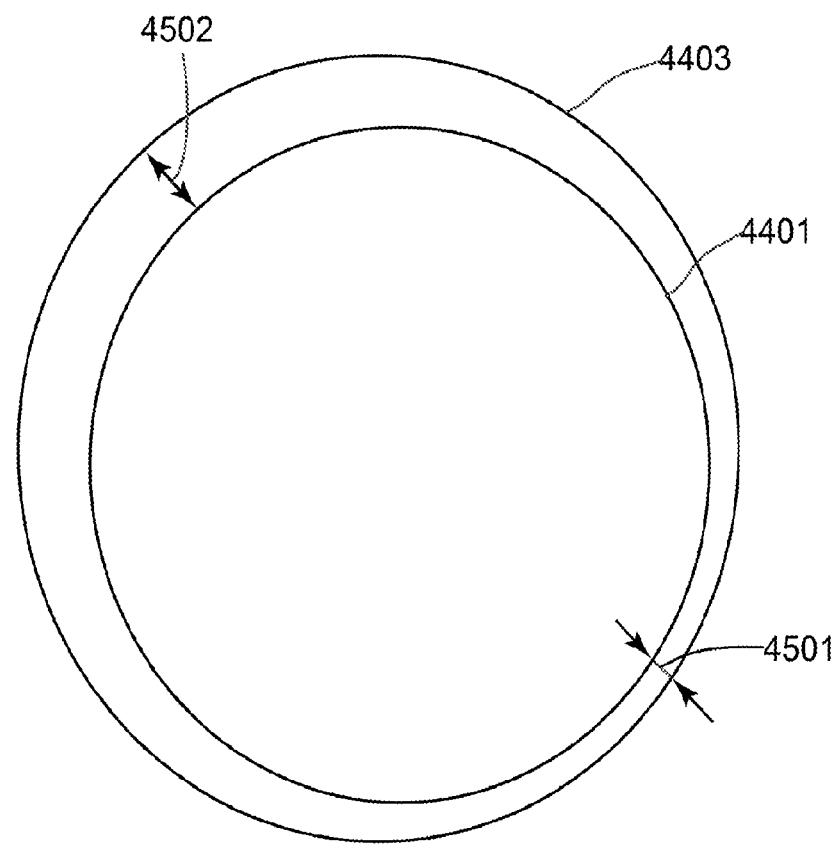
Figure 46:
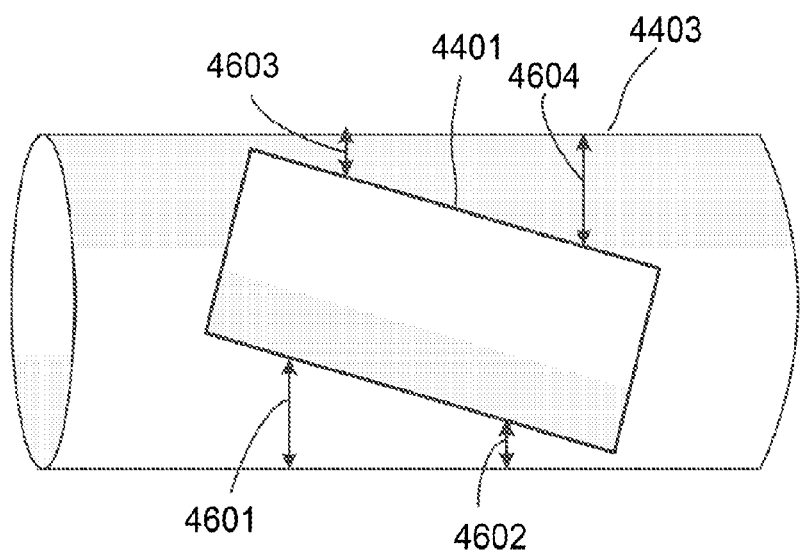

ILI tool 4401 may have flexibility to permit variation of pipe circumference, passing turns, curves, and other pipeline features. FIGS. 45 and 46 illustrate how this flexibility may result in offset from the center of the pipe and tiling, respectively. Lift-off at each sensing element may be used to determine both the location of the tool within the pipeline and the tilting of the tool. For example, in FIG. 45, lift-off 4501 and 4502 can be used to determine the offset of the tool 4401 within the pipe 4403. Also, in FIG. 46, lift-off data at two or more axial locations maybe be used to determine the tilt of the tool 4401 within the pipe 4403. This information is in turn used to improve the magnetic permeability estimates, accounting for the effects of the pipe wall curvature, the offset of the tool from the center of the pipe, the tilting of the tool and the retraction of the mechanical arms for each individual arc.

System electronics of ILI tool 4401 may be configured to provide a single relatively high frequency excitation sign to sensors 4411-4415. Here, a high-frequency is a frequency at which the depth of penetration of the magnetic field into the material is less than 2 mm for pipes and this is less than the wall thickness. The lift-off may be estimated at each sensing element along with the magnetic permeability in the direction perpendicular to the drive conductor arc-shaped segments, and the lift-off is used to estimate the internal corrosion associated wall loss. The magnetic permeability may be used to detect cracks. The drive conductor oriented circumferentially allowing improved detection of seam weld defects and other axially oriented linear defects including cracks and lack of fusion. In another such embodiment, the drive conductor is oriented at 45 degrees to the pipe axis to enable detection of both girth weld cracks and seam weld cracks as well as other crack like defects in circumferential and axial orientations. In another such embodiment a meander drive or interdigitated rectangle drive is used to create a spatially periodic field around the circumference such that the meander drive longer winding segments are aligned axially so that they are most sensitive to the magnetic permeability variations in the circumferential direction. In one such embodiment the magnetic permeability is used to detect circumferentially oriented cracks. In another such embodiment the circumferential component of the magnetic permeability is used to estimate the hoop stress.

In one embodiment, the tool provides only a high frequency mode because the lower allowable frequency is constrained by the requirement to provide high data resolution in the transit (axial) direction. The lower allowable frequency is defined for this tool as being at a frequency above that needed so that one complete cycle for the drive current is completed within the tool transit time interval that allows the tool to travel a distance that less than the required axial data resolution at the maximum anticipated tool speed. For example, if the maximum tool transit speed is 20 meters/second, and the required data resolution in the transit direction (axial) is 2 mm, then the minimum frequency of operation is 20 kHz. Under some special circumstances, impedance estimation can be provided using half a cycle (period) to provide higher resolution, but this may result in a substantial data quality reduction. Given the lower allowable frequency and the skin depth associated with magnetoquasistatic sensing field penetration into typical pipe steel, the inventors provide that this tool embodiment provides detection of internal corrosion, internally initiated cracks, internal stress and other such internal properties or defects of the pipeline material that can be interrogated with magnetic fields that are limited in their depth of penetration by the skin depth (or depth of penetration) of the applied fields at the prescribed input current frequency. In one embodiment of this invention, the miniaturized electronics and the use of precomputed databases allows the tool to provide sufficient reproducibility to provide a quantitative estimate of defect growth rates and to improve the confidence in defect sizing and detection by providing multiple inspections of the same defect. In another such embodiment the reproducibility of the data enables detection of changes in the pipeline magnetic permeability due to the stress condition associated with land movement, seismic events, mechanical damage, or operations.

The value of providing a tool that can only detect internal defects and internal stress condition is significant for applications where conventional tools cannot provide the performance needed for such defects to ensure pipeline integrity. One example is sour gas pipelines with variable elevation. For such sour gas lines, internal cracking and corrosion can impact pipeline integrity. MFL tools require relatively constant speed and have limited detection sensitivity and reproducibility and require long pig launchers. Thus, for many such sour gas pipelines with variable elevation, tool speed cannot be sufficiently controlled and MFL performance is not sufficient. For such applications, there is a need for a tool that can be run frequently, provides reproducible results for internal defects and stress imaging that allow comparison between runs for quantitative determination of the growth of defects and changes of stress conditions.

Figure 48:
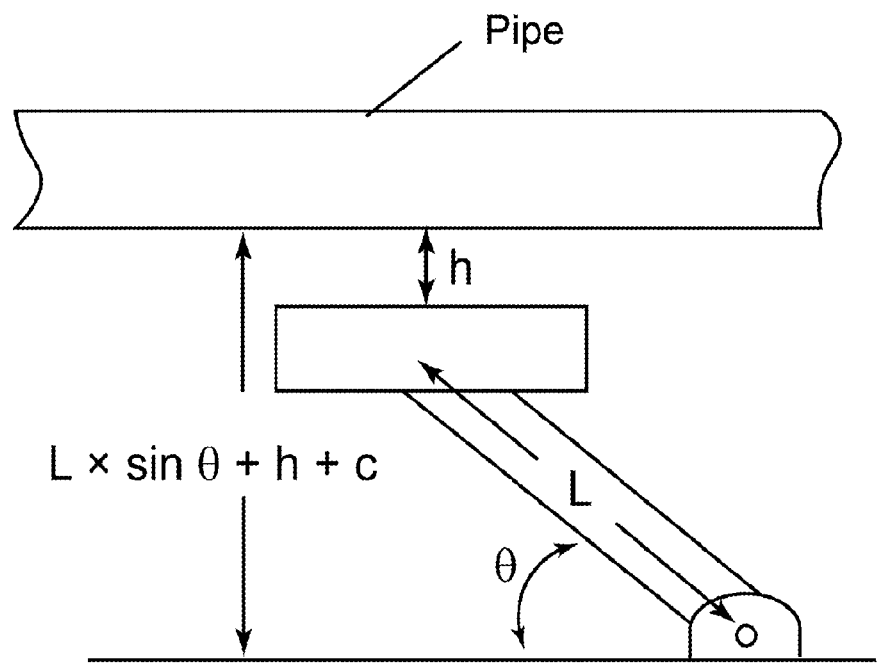
Figure 49:
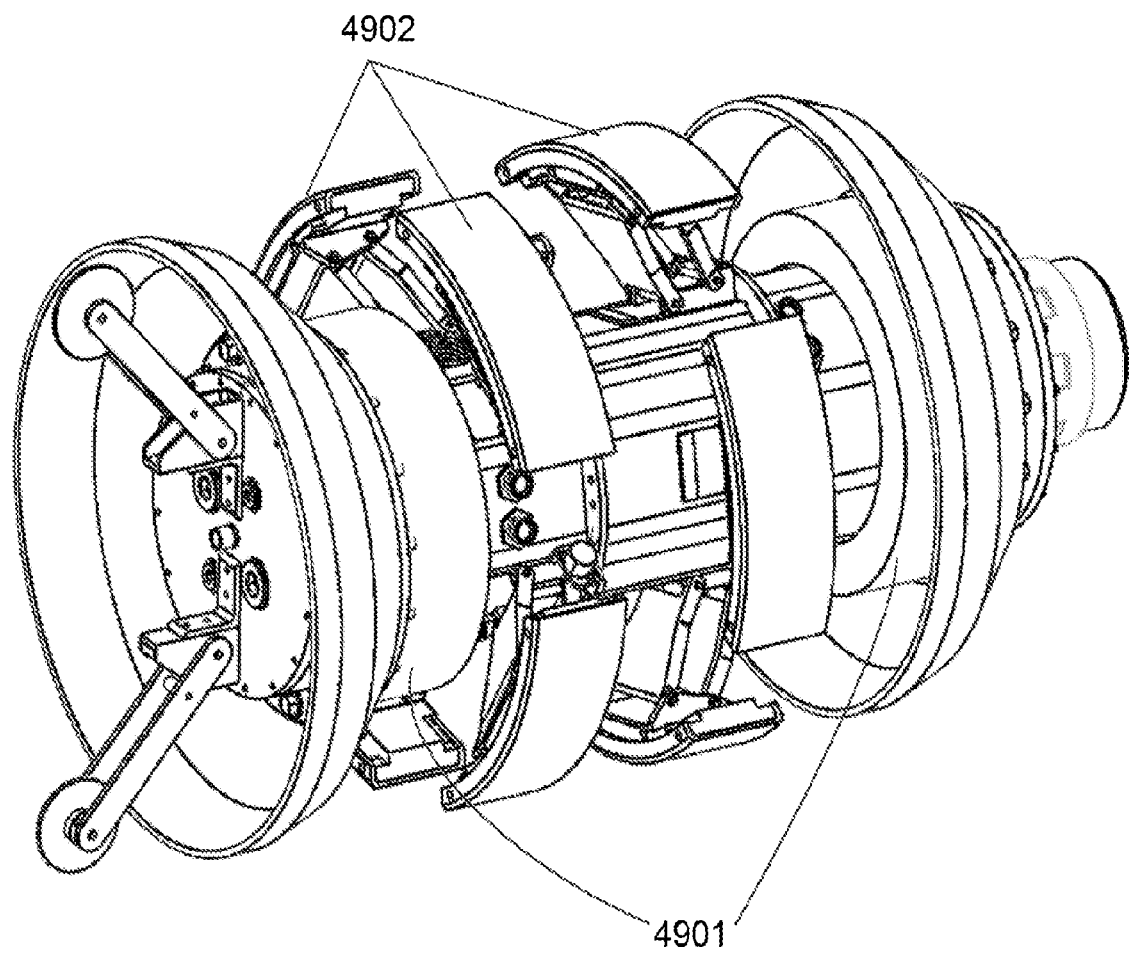

In one embodiment of the tool for internal damage and stress imaging, as well as for other tool constructs, the position of the retractable mechanical arms and the lift-off measurement information is used to provide the internal profile of the pipe for the purpose of assessing corrosion, mechanical damage (such as dent size), and ovality of the pipe. FIG. 48 shows how the distance from the tool body to the pipe can be estimated using the arm length (L), the arm angle (θ), the sensor liftoff (h), and the offset (c, which accounts for fixed portions of the assembly). By using multiple sensor heads placed around the tool body and by assuming the geometry of the tool body, the shape of the inner surface of the pipe can be estimated. Local changes in the inner surface would indicate corrosion, particularly if the change was radially outward. Local changes that are radially inward or are associated with large permeability changes are likely mechanical damage sites. In one such embodiment, tilting of the tool is also accounted for using two rows of arcs that are offset axially both to allow full circumferential coverage as described earlier and to provide the estimation of the tilt angle relative to the pipeline centerline. This enables correction of the profile computation to provide improved estimation of dent geometry. In another such embodiment, the magnetic permeability measurements provided using the precomputed database described earlier are used to estimate the stress distribution at and near a mechanical damage site In one embodiment, the inventors provide a purely electromagnet driven in-line inspection tool with no permanent magnets, but including an MFL emulation mode with constant fields, as well as an eddy current mode. In this case, constant means that a constant current is driven into a coil to produce a constant magnetic field. FIG. 49 shows a typical configuration showing the eddy current sensors (4902) and two fixed coils around the tool body (4901). The constant field may be produced by the same drive windings as the eddy current sensors (4902) or by the fixed coils around the tool body (4901). The same winding (4902 or 4901) may be used to provide sinusoidal magnetic fields at one or more prescribed frequencies. In some embodiments, one or more additional windings are included to provide additional field modes at prescribed frequencies and at constant field, as needed to provide the information needed to characterize the defects of interest. For example, multiple fixed coils could be used to produce high fields and low fields to further characterize ID and OD defects. These fields could be produced on the same module or on a different module (each module is an independent tool that are strung together to make a larger tool).

Bucking coils can be used to enable MR sensors to operate within the large fields. These bucking coils are coils of wire placed around the sensing elements. A current is driven into the coils such that the field produced by the bucking coil cancels the field produced by the MFL emulation electromagnets.

In some embodiments, the power supply is recharged during operation. Recharging may be achieved by wheels riding along the inside of the pipe wall to run a generator that charges the batteries. Alternatively, the generator may provide direct power through a power supply circuit.

In some embodiments, there is a single drive coil for multiple sensing elements, and the sensing elements are magnetoresistive. In another such embodiment the sensing elements are of a different variety including anisotropic magnetoresistors (AMR), giant magnetoresistors (GMR), hall sensors, inductive coils or other sensing elements for measuring one or more properties of the magnetic field such as the magnetic field amplitude, phase, direction, or rate of change of the magnetic field. Sensing elements may be configured in an array to enable building of images. In some embodiments the sensing elements are configured to measure the radial component of the magnetic field or the rate of change of the magnetic field. In some embodiments the sensing elements are configured to measure the component of the magnetic field perpendicular to a linear drive conductor. In another such embodiment, two components of the magnetic field or the rate of change of the magnetic field are measured.

Figure 50:
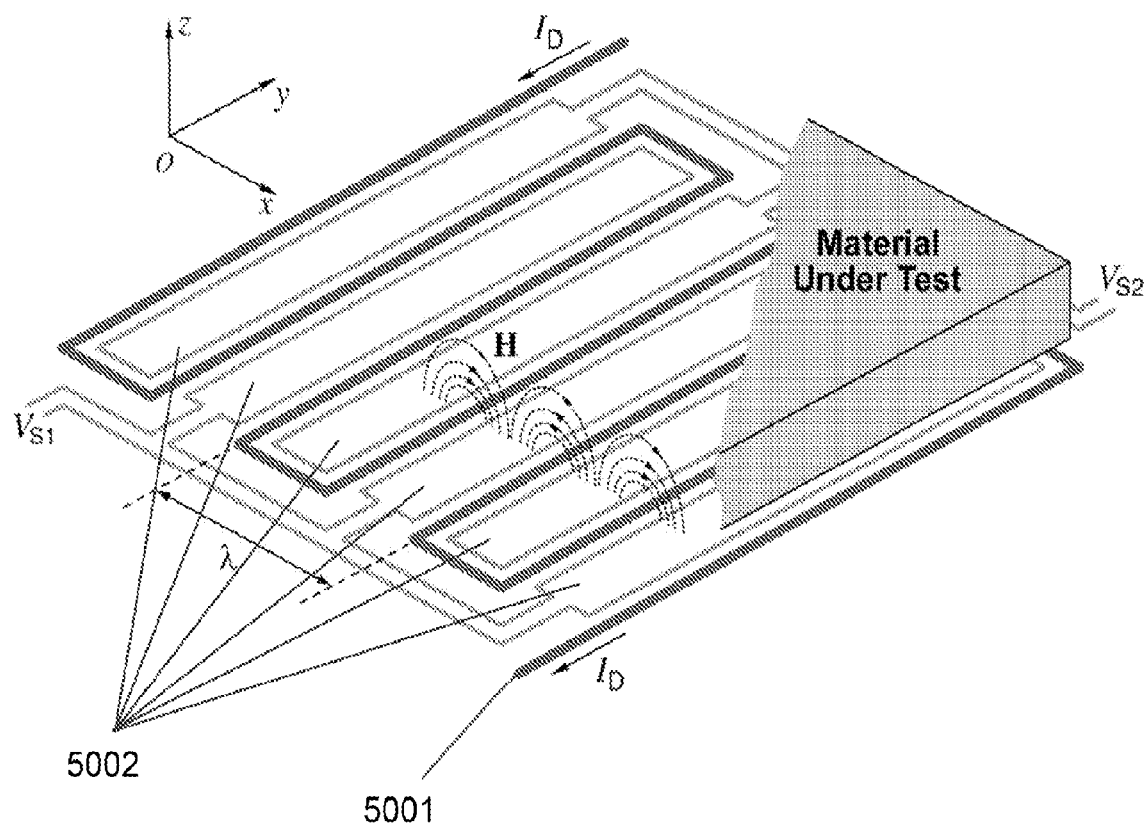

In another embodiment, each sense element has its own associated drive. FIG. 50 shows an example of a sensor that has a single drive winding (5001) and a single sense element (5002). In this example, multiple loops are connected in series to produce a single effective sense element.

Figure 51:
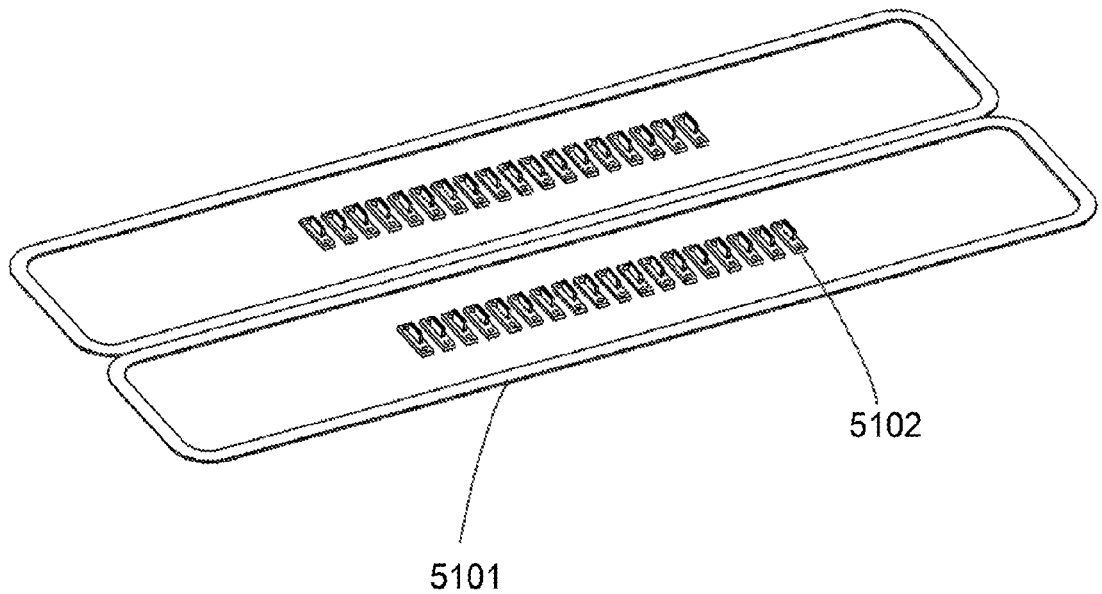

In yet another embodiment, dual rectangle drive conductors are used to provide both the constant and prescribed frequency modes to enable high-resolution imaging and reliable detection of external defects, mid-wall defects, and internal defects including corrosion, cracks, mechanical damage and manufacturing anomalies—all of these either at welds, near welds or away from welds in the base material. FIG. 51 shows the dual rectangle drive conductor (5101) and the array of sense elements (5102). In this example, the sense elements are MR, but alternative sense elements can be used. A row of sense elements is shown in the center of each rectangle of the drive winding, although these sense elements can be offset from the center.

Figure 52:
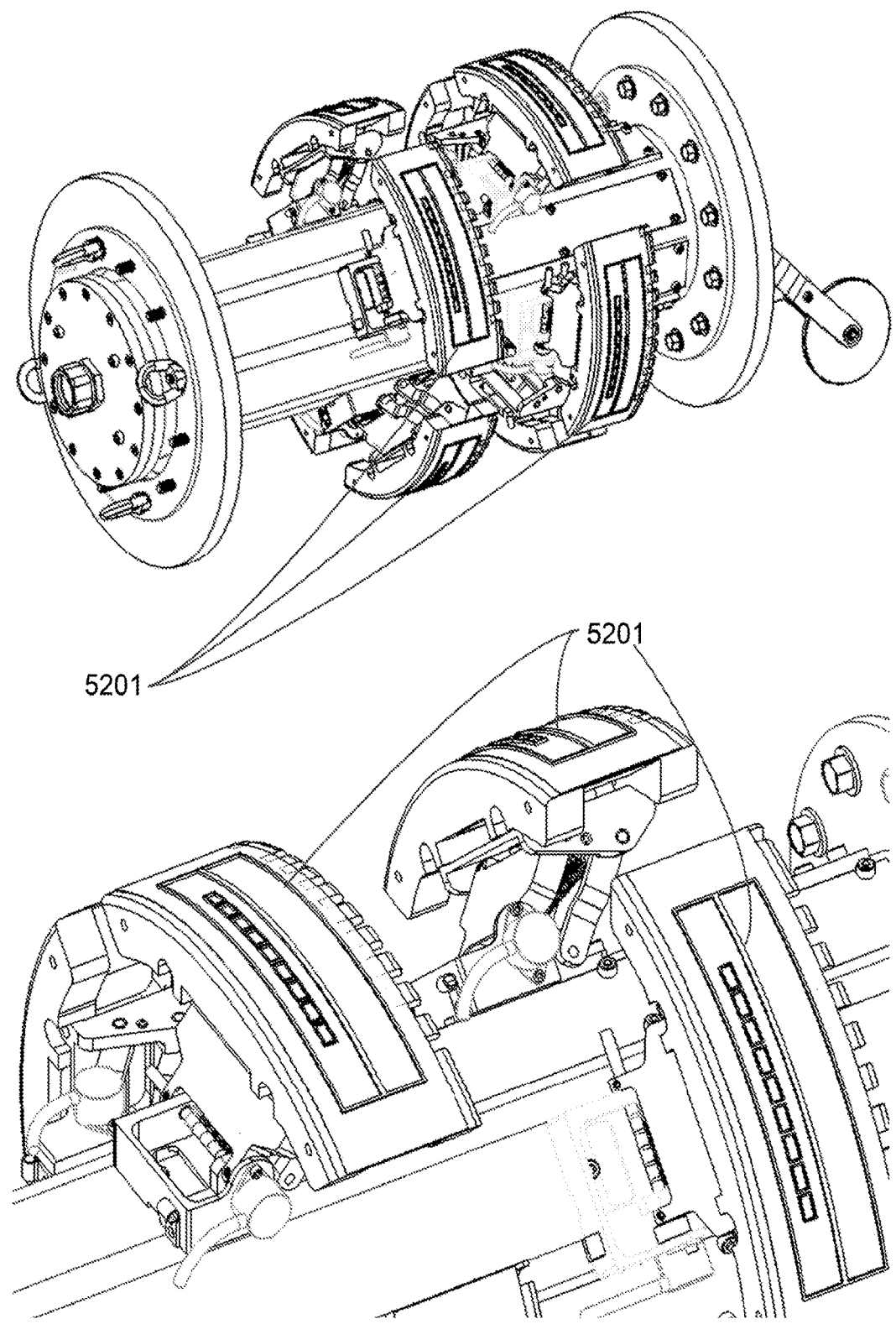

In some embodiments, the windings are oriented circumferentially to enable imaging of longitudinal stresses by estimating the longitudinal magnetic permeability using a multi-variate inverse method with a precomputed database for estimating the lift-off, permeability and wall thickness or other sets of properties as needed. FIG. 52 shows a tool with a circumferential drive (5201). This embodiment enables detection of residual and applied stress variations associated with mechanical damage, welding and post weld heat treatment, land motion, elevation and elevation variations/land slope, and other sources.

A cylindrical coordinate model may be used to estimate parameters such as sensor lift-off and pipe properties. For example, the model may be used to generate precomputed databases which are used in conjunction with multivariate inverse methods to process sensor data. Though, other methodologies to estimate the parameters of interest from sensor data may be used (regardless of whether they utilize a cylindrical coordinate model).

In using the cylindrical coordinate model, a correction factor may be provided for circumferential and/or axial misalignment (i.e., lack of concentricity) of the tool within the pipe. As previously described, two rows of MWM-Arrays may be used in the determination of the axial misalignment with the internal pipe wall. Similarly, the lift-off at each sensing element may be used to correct for the non-concentricity of the tool with the internal pipe wall.

In another embodiment, the position and misalignment of the tool is estimated using the lift-off data estimated using a relatively high drive frequency. This position information is used along with the multivariate inverse method and a constant field mode (which may be an MFL emulation mode or an alternative constant field mode) to provide wall thickness estimation. A complete image of the tool position and the pipe wall is built for all inspected segments of the pipeline.

The MFL emulation mode replicates the results of conventional MFL tools, providing an alternate means of compliance with existing standards. The field needed to provide a sufficient MFL emulation mode is substantially reduced by replacing the MFL hall sensing elements with the more sensitive MR sensing elements. A low-field tool uses lower power in a constant field mode (MFL emulation mode) to extend the time that batteries can operate without recharging or to limit the recharging capacity needed in the tool.

A tool adapted to provide the low-field mode may be configured to perform method 5400 shown in FIG. 54. In this mode, the magnetic permeability and the wall thickness of the pipe as well as the sensor lift-off are estimated from sensor measurements. In some embodiments, the high frequency is used to estimate the lift-off and provide a first guess for the permeability. The magnetic permeability and the nominal wall thickness can be used to adjust the amount of field being generated in order to minimize the power consumption. Then the constant field sensor response is used to estimate the thickness and correct the permeability.

FIG. 53 shows the process for estimating the conductivity of the pipe. A first guess for the wall conductivity is used to determine wall thickness or it can be estimated using the nominal wall thickness estimated in regions away from likely defects. In this nominal wall thickness method for conductivity estimation, the better the nominal thickness is known, then the less error is introduced into the other property estimates.

In some embodiments a uniform layered media model is used for the initial estimation of lift-off, wall thickness, and permeability and then a stored database of numerically simulated defect responses is used to correct the defect size estimates (e.g., the depth of a corrosion defect or the length and depth of a crack). An empirical result set may be used for the detect size correction instead of the numerical simulations. In yet another embodiment, a calibrated formula is used to correct the defect size; for example, the formula may be the ratio of the effective sensor footprint size to the estimate defect surface extent.

In some embodiments method 5300 is used to correct the permeability estimates around a mechanical damage defect or a weld to provide residuals stress estimates.

In one embodiment, the longitudinal stress is estimated using a relatively high frequency mode to estimate the residual stress at a weld to assess the post-weld heat treatment (PWHT). Stress assessment may be accomplished using an eddy current sensor at a high enough data rate to obtain at least 4 data points within the weld heat affected zone. At least four data points are needed to provide shape characteristics of the stress variation associated with PWHT. Both the higher frequency and constant current modes may be used to characterize the PWHT. In another such embodiment the quality of the welding is assessed instead of the PWHT. The weld quality is assessed using the shape of the magnetic permeability response as the tool travels across the weld. Characteristics of the shape are used to assess the weld quality. In one such embodiment the maximum weld permeability and the width of response at half the peak value are used to provide a measure of the weld quality. It has been shown in the past that such features correlate with lack of fusion or other such defects.

In some embodiments the electronics, processors, sensors, and storage media are miniaturized to fit into a single module suitable for integration with a cleaning tool scrubber or utility PIG format. In this embodiment, performance is compromised as needed to achieve a small enough module size to enable access with normal cleaning PIG launchers, not the more complex inspection PIG launchers. For example, combining many of the electronic components onto a single circuit board (and eliminating the interconnections) reduces the size of the electronics. Reducing power consumption and using high energy density batteries reduces the size of the batteries. Also, eliminating the magnets used in typical MFL tools provides more space in the interior of the tool.

A preferred means is to develop dedicated chip sets to further miniaturize the electronics and reduce power requirements. For example, the analog-to-digital converters, the processor, and the communications functions can be combined into a single chip that has a more desirable form factor. The cost of such an implementation is prohibitive but the concept is included in the disclosed invention.

In one embodiment, structured waveforms (in terms of the drive current or voltage) are used to drive the drive windings to achieve improved wall thickness, magnetic permeability, or defect detection performance. One such structured waveform is a DC bias field with a single frequency superimposed. The impedance instrument independently measuring the DC field response and the real and imaginary part of the transinductance associated with the single frequency. Another structured waveform further includes a second superimposed frequency to estimate the wall thickness of the pipe.

For robotic tools or slowly moving tethered tools, both MR and inductive sensing elements may be used, but for fast moving tools, the preferred method is inductive at high frequency drive current (e.g. providing shallow penetration) and using a very high data rate for recording for the sensor impedance (or transinductance measurements). In some embodiments filtering is included near the sensor for data taken at a high data rate to improve the signal to noise.

In one embodiment for estimating permeability and conductivity independently for the pipe wall, the constant field and both a low frequency and higher frequency mode are used to provide independent estimates of the liftoff, conductivity, permeability and pipe wall thickness. This four unknown problem requires two frequencies and the constant field mode. Since the impedance measurement requires a full period, the data rate at the lower frequency will be very low, which will produce very coarse data density. The property estimates produced by the low frequency can be used by the constant field and high frequency modes to provide improved defect size estimates.

In another embodiment, other complex excitation modes are used. In one such embodiment, a constant ramp of current is used with two separate ILI tool modules that excite a saw tooth ramp so that one ramp is always varying with a constant slope to enable complete internal coverage. The ramp mode is unique in that it enables the penetration of the wall, but the first derivative of the field is constant, thus the eddy current patterns and the inductive coil response are simplified. In this mode, the two separately excited ramps must be synchronized and out of phase. The advantages of this mode are both the simplified eddy current patterns and the ability to provide high data rates, as with MFL, but still excite the eddy currents to improve defect sensitivity. For crack detection, this mode is of particular value since eddy currents can be induced throughout the wall thickness enabling higher sensitivity to linear crack like defects. This is of particular interest for ERW pipe seam welds and girth weld cracks.

Figure 47:
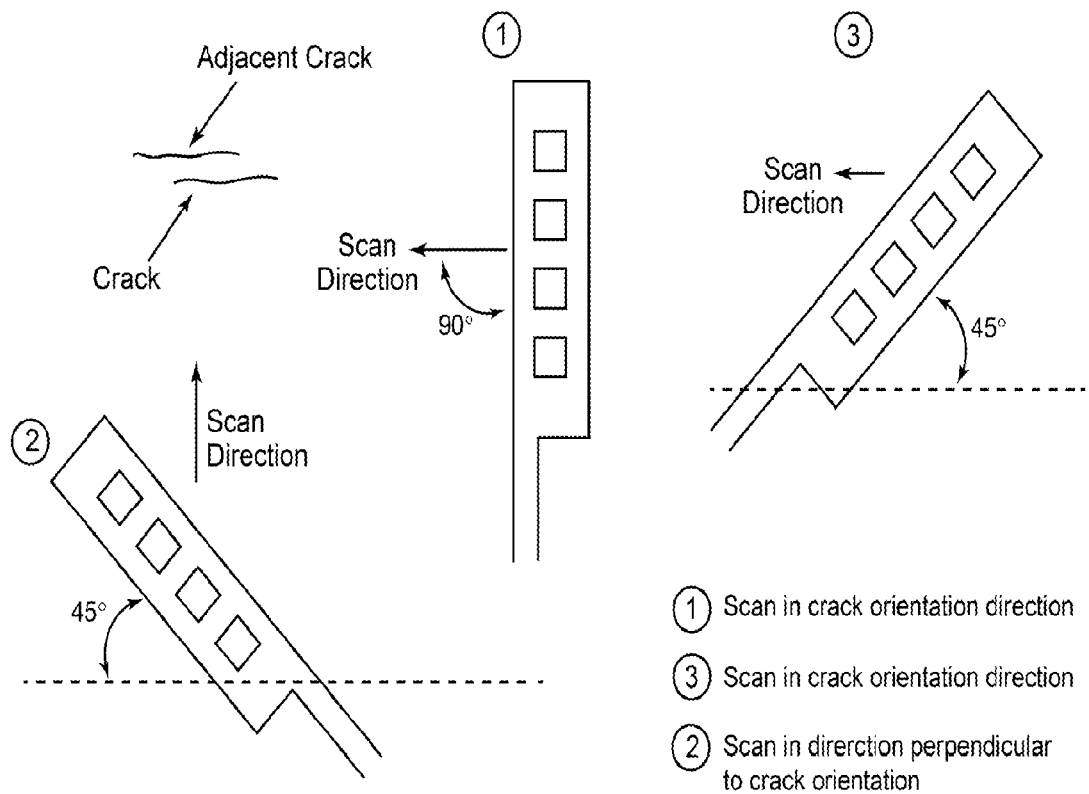

For crack detection, the orientation of the array relative to the orientation of the crack will affect the magnitude of the response. In FIG. 47, scan orientation 1 shows the scanner traveling in the same direction as the length of the crack with the drive winding oriented perpendicular to the crack, which will provide the highest sensitivity to single cracks. For crack clusters (two or more cracks in close proximity), the crack response from the two cracks will combine if the cracks are too close together. Scanning at an angle relative to the crack length will decrease the magnitude of the crack response, but increase the effective resolution of the scan. This increased resolution can be used to differentiate between cracks and provide independent measurements of crack location and crack depth. In FIG. 47 scan orientation 3 shows the scanner traveling in the same direction as the length of the crack with the drive winding oriented at 45° to the crack. Another methods is shown in FIG. 47, scan orientation 3, where the scanner traveling perpendicular to the length of the crack with the drive winding oriented at 45° to the crack.

Section E-I: Thin Sheet Inspection

Figure 62:
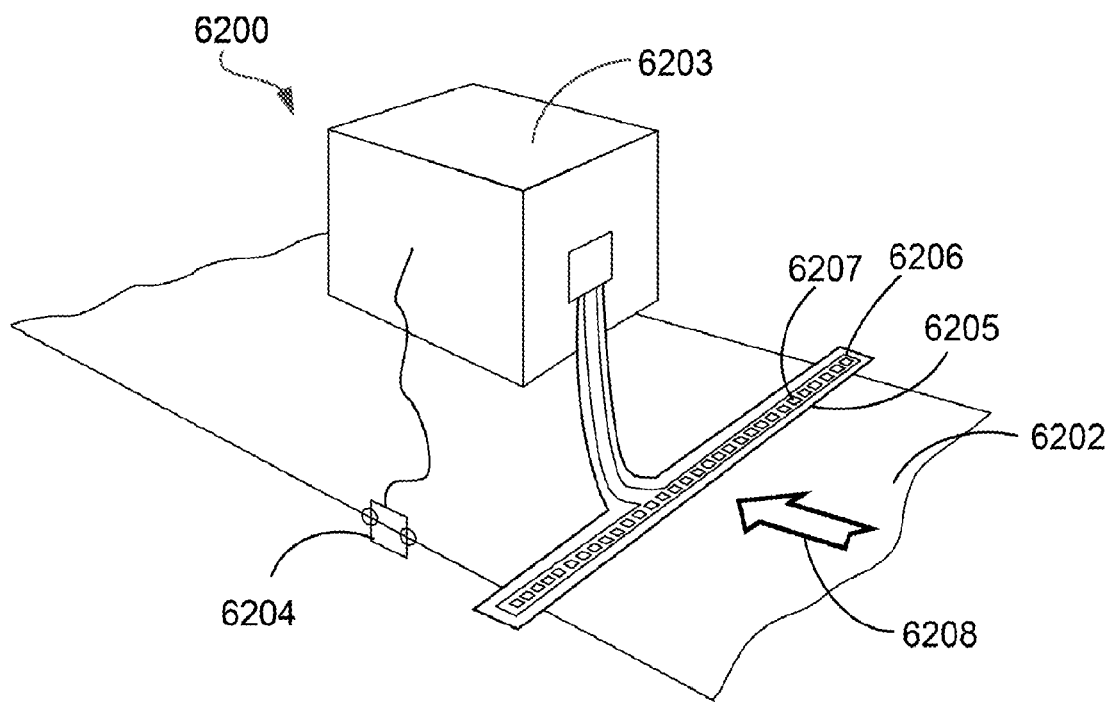

FIG. 62 shows a system 6200 for inspecting a thin sheet of conducting material 6202. The system includes an instrument 6203, sensor 6205, and motion encoder 6204 that may be similar to instrument 110, sensor 120 and motion encoder 143 shown in FIG. 1.

Thin sheet 6202 may be moving relative to sensor 6205 as indicated by arrow 6208. Arrow 6208 indicates the scan direction. In some embodiments, such as that shown in FIG. 62, thin sheet 6202 moves perpendicular to the direction of an array of sensing elements 6207 in sensor 6205. In some other embodiments, sensing element array 6207 is at an angle with respect to the scan direction of thin sheet 6202 (e.g., 45 degrees). Encoder 6204 may record the movement of thin sheet 6202 and instrument 6203 may store the position of thin sheet 6202 in association with each sensor measurement and/or derivatives thereof (e.g., properties, states, conditions).

A drive winding 6206 of sensor 6205 may be driven by instrument 6203 with an electrical current at an excitation frequency which produces a depth of penetration (DOP) between 50% and 150% the nominal thickness of thin sheet 6202. DOP is defined as follows:

DOP=1/$Re\{\Gamma_1\}$ where:

$$\Gamma_n = \sqrt{(2\pi n/\lambda)^2 + j2/\delta^2} \text{ and } \delta = \sqrt{\frac{1}{\pi f \mu \sigma}}$$

In this equation $\lambda$ is a characteristic length of a sensor, $f$ is the frequency of the input current, $\sigma$ is the electrical conductivity of the thin sheet, n is 1, j is the imaginary unit, and $\mu$ is the magnetic permeability of the thin sheet. The characteristic length of a linear drive eddy current sensor is defined as 4 times the distance between the linear drive portion of the drive winding and the center of the sensing elements.

Figure 64:
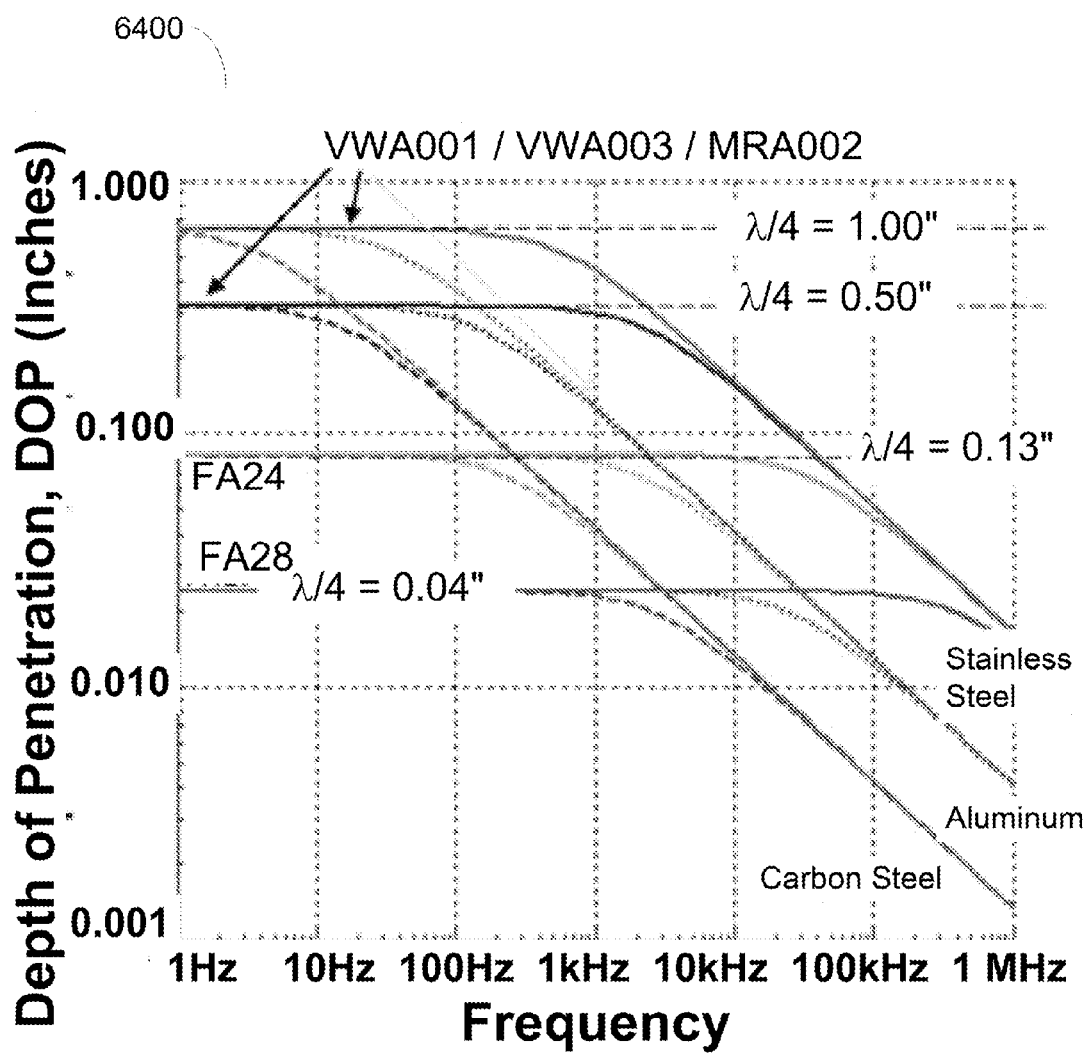

FIG. 64 shows a plot 6400 showing the depth of penetration as a function of frequency for several characteristic sensor lengths and materials. Note that plot 6400 is a log-log plot.

Figure 65:
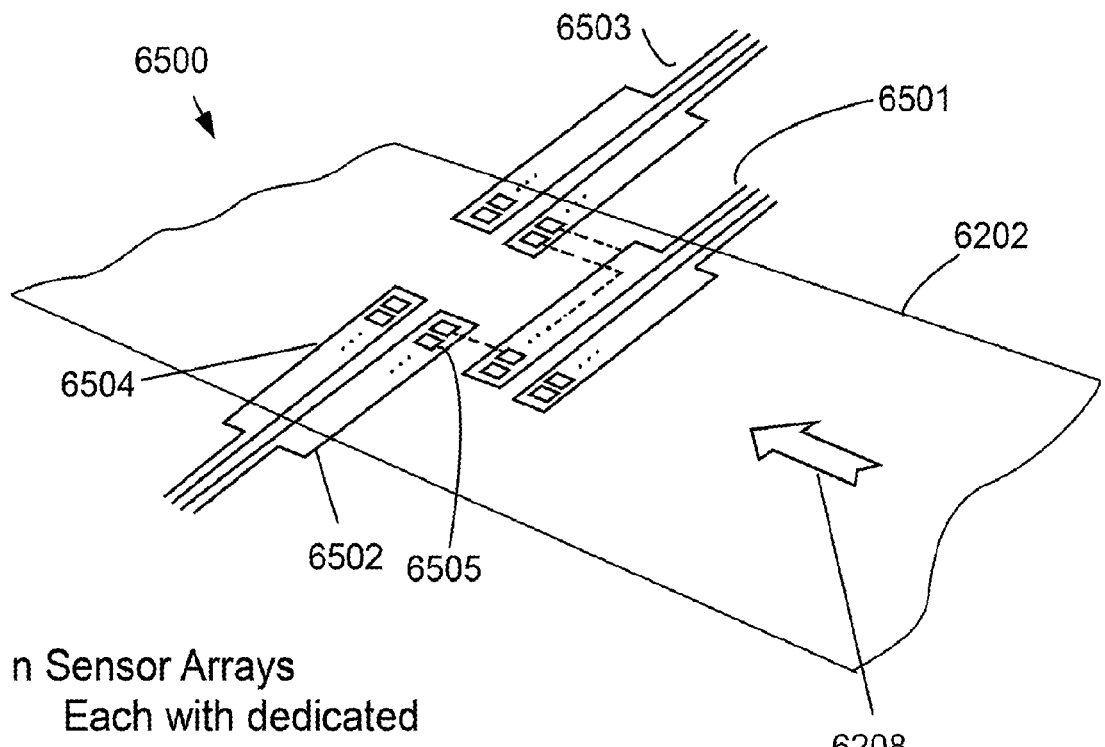

In some embodiments of system 6200, sensor 6205 has drive winding 6206 in the form of a single rectangular winding and the elements of sensing element array 6207 are rectangular coils of one or more turns that are arranged in a linear array within drive winding 6206. In some embodiments, drive winding 6206 also includes a second rectangular winding adjacent to the first, as shown in FIG. 65 for dual rectangle arrays 6501, 6502, and 6503 with the windings connected in series so that the current in the closest drive segments are in the same direction. A second array of sensing elements, 6504, may be included within the second rectangular winding, in addition to the first sensing element array, 6505, for each of multiple dual rectangle sensor 6501, 6502 and 6503. The multiple dual rectangle sensor arrays may be arranged to cover the width of the thin sheet as shown in FIG. 65.

The thickness and relative speed of thin sheet 6202 along with the sensor excitation frequency and sensor geometry may be used to determine the resolution of system 6200 in the scan direction. The resolution perpendicular to the scan direction will be determined by the element spacing in the eddy current array, 6206.

As described above instrument 110, may be configured to provide a transimpedance measurement for each cycle of the excitation current. The lowest excitation frequency will therefore drive the resolution of the system in the scan direction. For example, for a sheet moving at 10 meters per second and a 10 kHz lowest excitation frequency, a data resolution of 1 mm in the scan direction may be achieved. Resolution requirements may be Prescribed by the operator or determined based on detection sensitivity for a given defect type and minimum size. To determine sensitivity computer simulations or empirical data can be used.

The resolution may be improved in the scan direction by reducing the DOP required to perform the inspection or by modifying the material properties of thin sheet 6202.

Figure 63:
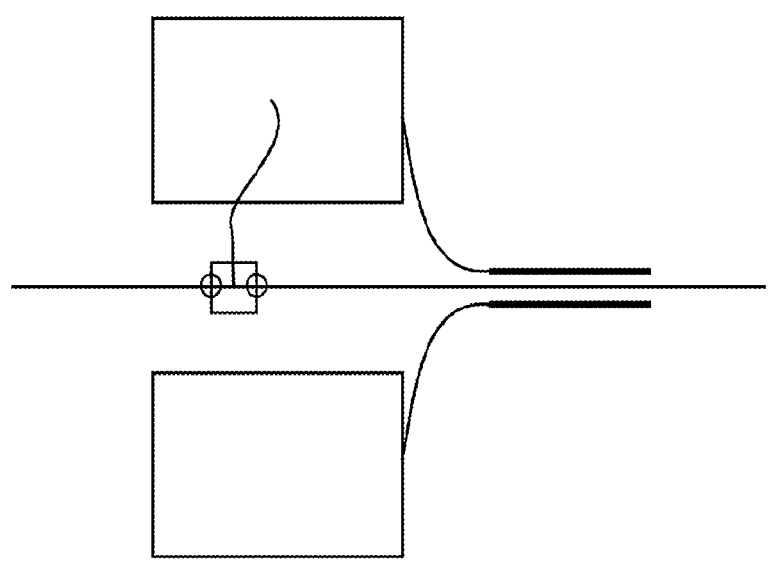

The DOP required to perform the inspection may be reduced by inspecting from both sides of thin sheet 6202. FIG. 63 shows a system similar to system 6200 which additionally includes a second sensor below thin sheet 6202. The sensors may be provided at the same location (as shown in FIG. 63) as the sheet moves past the sensor or offset from one another in the scan direction. Where the sensors are aligned, the lift-offs from each sensor may be measured and subtracting from the total gap between the sensors to determine the thickness of the sheet. The total gap may be controlled mechanically such that it can be treated as a constant during data processing. Interference between the sensors may be reduced by operating the upper and lower sensors at different excitation frequencies. Though in some embodiments the two sensors are aligned and the same excitation current is provided in both drive windings.

In some embodiments a constant magnetic field is provided near the sensors and thin sheet 6202 such that the magnetic permeability of the sheet is substantially reduced.

As can be seen from the DOP equation, a reduction in the magnetic permeability will increase the depth of penetration.

In one such embodiment the lowest frequency is increased to the highest value with a depth of penetration between 0.5 and 1.5 times the sheet thickness such that sufficient sensitivity is provided for the smallest defect size that must be detected. Here, sufficient sensitivity is defined as the signal to noise ratio at which the detection of the smallest required defect is provided with approximately 90% probability of detection and high confidence of over 80%. In one such embodiment a means is also provided for estimating the defect size. One such means first characterizes the defect as near side, far side or through wall. Then assuming a defect geometry a database of defect responses is used to estimate the defect size using the sensing element responses.

A method is provided for detecting small defects in the thin sheet where small sensing elements of 1 mm by 1 mm are provided to form the arrays. The impedance response is provided for each sensing element simultaneously and a precomputed database of sensor responses is used to convert the highest frequency impedance data to an estimate of the distance between the sensing element and the nearest surface of the conducting sheet under test. In one such embodiment the same database for the highest frequency is used to estimate a property of the sheet, such as the conductivity (assuming a constant magnetic permeability) or the magnetic permeability (assuming a constant conductivity). In one such embodiment the highest frequency is selected so that the depth of penetration at that frequency is substantially less than 0.5 times the thin sheet thickness. In one such embodiment with at least two frequencies, a precomputed database and the lift-off (proximity) estimate from the highest frequency are used to convert the lower frequency data into estimates of the thickness of the thin sheet and the value of another property of the sheet, where the property may be the magnetic permeability of the sheet with an assumed constant electrical conductivity. In another such embodiment the thickness is estimated by a separate means at one location and subsequently, using the thickness estimate, the conductivity at this and other nearby locations is estimated independently from the magnetic permeability. Multiple such locations with alternative thickness measurements are then used to provide electrical conductivity values for the entire sheet being inspected.

In one embodiment the magnetic permeability in the direction perpendicular to the longer drive segments is also used to estimate the stress in the thin sheet. This is possible with all sensor configurations described for the thin sheet measurements.

In one embodiment of the above inventions the sheet is formed into a pipe and the sensor arrays are located inside the pipe and the sensors are traveling, as opposed to the thin sheet. In this invention the sensor array is mounted on an in-line-inspection tool.

It should be appreciated that while an apparatus and method have been described in connection with a thin film that embodiments may address a variety of conductive layers such as pipes, pipelines, panels, and the like.

In some embodiments of system 6200, the electrical current provided by instrument 6203 simultaneously provides a second excitation frequency that is higher than the first frequency. In one such embodiment the lowest frequency provides sufficient data resolution in the sheet transit direction to detect the minimum defect size of interest or to provide the desired data resolution. The second frequency provides higher sensitivity to near side defects and enables differentiation between through thickness and near side and far side defects. In one embodiment a far side defect is detected only by the lower frequency, while near side and through wall defects are detected at both frequencies. In one such embodiment the ratio of the response at the two frequencies for a property estimated from the response, such as the magnetic permeability, is used to differentiate through wall from near side defects.

Figure 66:
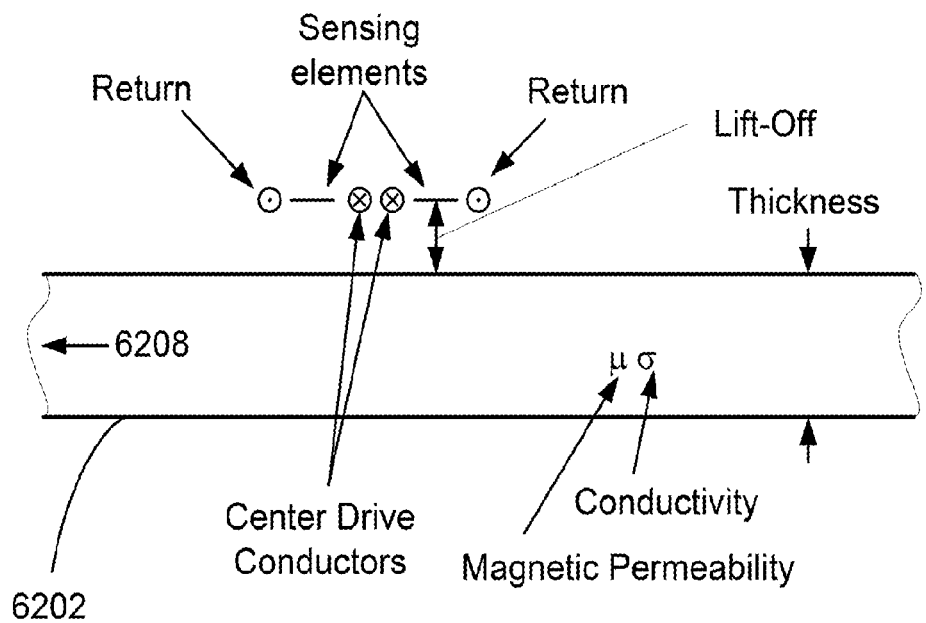
Figure 67:
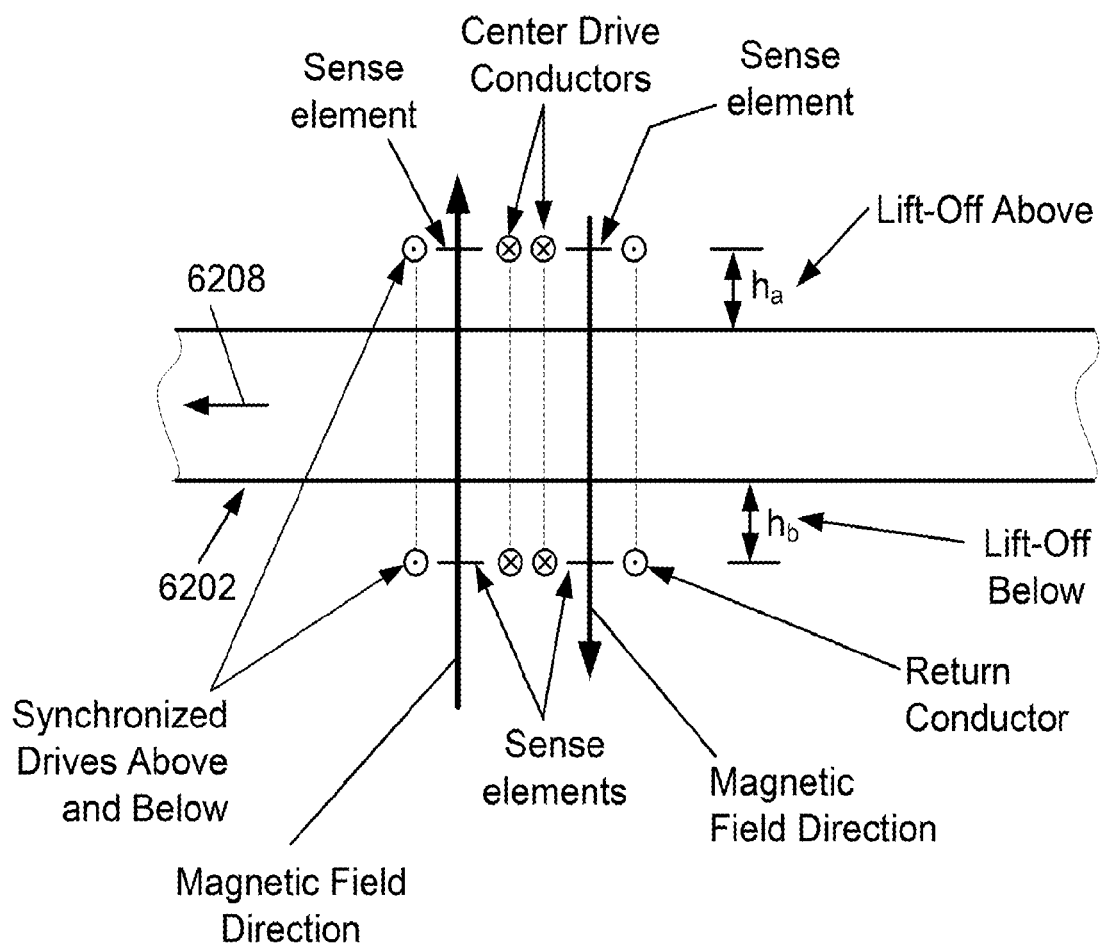

In one embodiment illustrated in FIG. 66 a precomputed database of sensor responses is used at one or more frequencies to estimate the lift-off, and a property of the thin sheet 6202. In one embodiment two sensors on opposite sides of the thin sheet as illustrated in FIG. 63 and FIG. 67 are synchronized so that the field from each sensor is in the same direction as shown in FIG. 67.

The first lower frequency and second higher frequency from both arrays may be used to estimate the magnetic permeability of the sheet with an assumed constant conductivity, and the magnetic permeability is used to detect defects and estimate their size.

A second higher frequency may be included and a two frequency multivariate inverse method is used to estimate the thickness of the sheet, one electrical property and the lift-off distance between the sensing element and the near surface of the sheet, all at each sensing element location.

The electrical property may be the magnetic permeability and the electrical conductivity is assumed to be a constant value for the sheet. The electrical conductivity may be determined by measuring on a sample of material from the same lot. The method used to measure the sample may be a four point probe method that accounts for the sheet thickness.

The above may be configured as a stationary inspection apparatus for measuring stress in a thin sheet moving relative to the inspection apparatus. The inspection apparatus may include a plurality of sensing segments, each sensing segment having an array of sensing elements at a fixed distance from a linear drive conductor; an impedance instrument having A signal generator configured to generate an electrical current at a first excitation frequency, said signal generator electrically connected to provide the electrical current to the drive conductor, and a plurality of parallel sensing channels, each sensing channel dedicated to a sensing element of the plurality of sensing segments and configured to simultaneously measure real and imaginary components of an impedance associated with the respective sensing element at the first excitation frequency, and the response at each sensing element being converted using a precomputed database of sensor responses over the range of properties and lift-off of interest to estimate the lift-off distance between the sensing element and the near surface of the sheet and the magnetic permeability of the sheet at the at least one frequency. A correlation relationship may be used for converting the magnetic permeability to stress, where this relationship was determined empirically using a sample of the sheet material and the same sensing array construct used in the apparatus. The system may determine the electrical conductivity of the sheet, said electrical conductivity then being assumed constant for the sheet.

The electrical conductivity and magnetic permeability are determined from a stationary sample of the sheet and are assumed to be constant for the sheet being inspected. A second higher frequency is used to estimate the magnetic permeability of the sheet with an assumed constant electrical conductivity. The electrical conductivity is determined using a four point probe method on a representative sample of the sheet material and the method accounts for the sheet sample thickness. A second sensing array is included on opposite sides of the sheet and the gap between the two sensors is held constant and the lift-off at a the single frequency for each pair of sensing element, above and below the sheet, is subtracted from the total gap to determine the sheet thickness. The drive currents for the array above and below the sheets are synchronized. The frequency is selected so that the depth of penetration of the magnetic field produced by the drive current is less than 0.5 times the sheet thickness. A second frequency is simultaneously applied to the drive conductor and the impedance at the two frequencies is used to estimate the sheet thickness, magnetic permeability and lift-off using a precomputed database of sensor responses. The magnetic permeability is used to detect defects in the plate in addition to measuring thickness. The magnetic permeability is used to measure the stress in the plate in addition to measuring thickness. Applying a constant magnetic field is performed by the system included at a field intensity sufficient to reduce the magnetic permeability by more than half applying a constant magnetic field is included at a field intensity sufficient to reduce the magnetic permeability by more than half Applying a constant magnetic field is included at a field intensity sufficient to reduce the magnetic permeability by more than half.

Section E-C: Weld and Post-Weld Heat Treat (PWHT) Assessment

Post-weld heat treatment (PWHT) is used to strengthen critical welds on pipes, pipelines and other structures. In this section it is assumed that the structure is a pipe or pipeline, but it should be appreciated that the methods and systems described may apply to any welded material structure. Conventional PWHT assessment capability is limited to hardness testing on the outer surface of the pipe. This method cannot provide a quantitative PWHT assessment after a weld has been purportedly heat treated. Also, this method cannot provide an assessment of residual stresses for girth, seam, spiral welds or other welds or for the base material. Thus, pipeline operators must depend on documentation and workforce skill to ensure quality of welds and PWHT. As documentation for pipelines and other critical structures may not exist, be incomplete or inaccurate, a method for qualification of both welds and PWHT before burying of pipelines is needed. Once a pipeline is buried, the methods and apparatus described in Section E-B may be used to enable inspection of PWHT and weld quality from the inside using an ILI tool.

Figure 55:
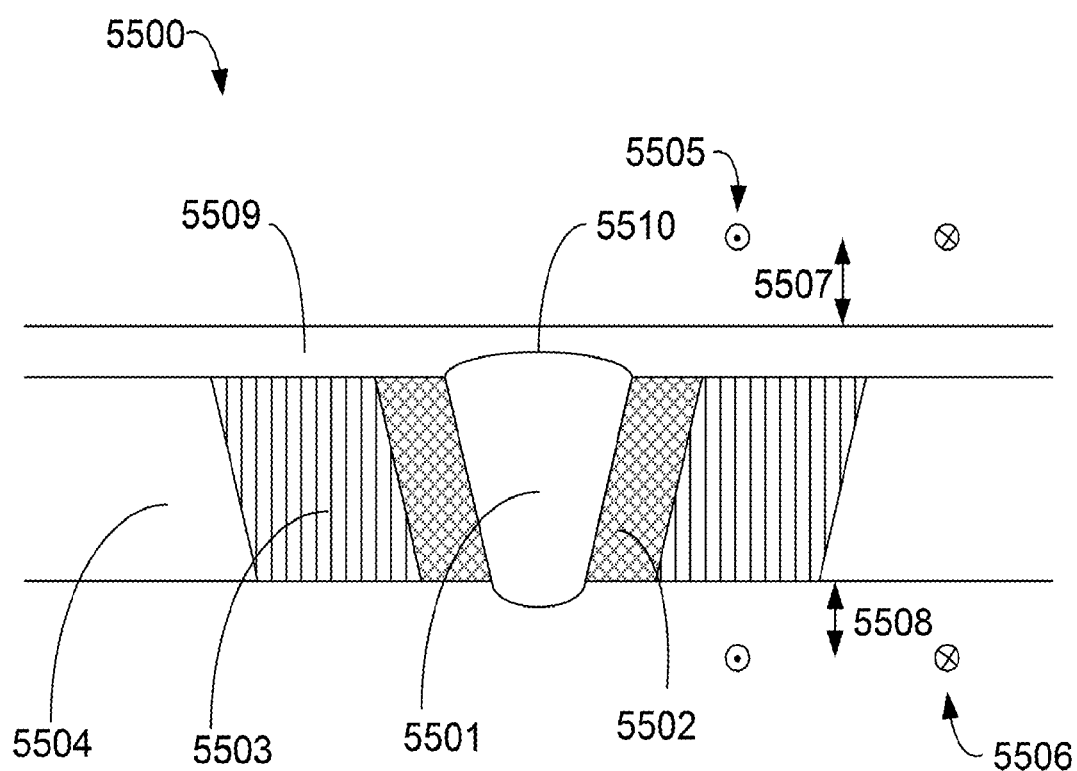

After welding to join two pipe sections using a girth (circumferential) weld, there are several zones of importance indicated by the pipe/weld cross-section 5500 of FIG. 55 taken in the axial direction. Starting at the center of the weld is weld 5501 itself, and then moving axially away from the weld there is the heat affected zone 5502 (HAZ), and continuing axially there is the base material 5504. Furthermore, there are residual stresses in the hoop and axial directions that have been documented in the literature both using models and experimentation. Hoop stresses are largest at the center of the weld and then can continue beyond the weld and past HAZ 5502 into base material 5504. Base material and weld related stresses can be the results of the welding process, the pipe manufacturing process, construction or service. Thus, there is a welding related residual stress affected zone 5503 (RSAZ) that includes weld 5501, HAZ 5502 and some portion of base material 5504 on both sides of weld 5501. Furthermore, if a PWHT is applied using a local heating coil solution, the coil will have a width typically more than 5 times the weld width. Thus, for a one inch weld width with a 6 inch wide heating coil, the PWHT affected zone will cover 3 inches from the weld center into the base material.

FIG. 62 show a method 6200 of assessing PWHT and/or weld quality. Method 6200 may be performed using a system such as system 100, shown in FIG. 1. Method 6200 may be performed at one or more sensor orientations to perform the assessment based on may be used to assess PWHT and weld quality by image of the axial and/or circumferentially oriented magnetic properties of the material. Sensor 120 may be a sensor sensitive to the magnetic permeability of the pipe. The magnetic permeability of the pipe may be measured using a time varying magnetic field at one or more prescribed frequencies. A database of precomputed sensor responses, generated using a model of the sensor and material under test interaction, may be used to convert the response of sensor 120 into both the magnetic permeability in the direction perpendicular to the drive winding of sensor 120 and to the lift-off. This can be accomplished for the weld and residual stress affected zone, as well as for the base material.

In some embodiments the change in magnetic permeability before and after PWHT is used to determine if the PWHT was performed properly. This approach may be used if the process is such that the change in magnetic permeability is dominated by the relaxation of detrimental residual stresses as a result of the PWHT process.

In some embodiments, the magnetic permeability is related to a measure of this residual stress in the pipe. The residual stress that remains after the PWHT process (or the change in residual stress before and after PWHT) may be used to determine if deleterious stresses remain in the pipe.

In some embodiments a library of spatial signatures (i.e., characteristic sensor responses) are stored for both before and after PWHT to determine features of the PWHT process for a given set of process parameters (e.g, welding parameters, welding consumable, PWHT process, pipe material, pipe geometry and the like). A spatial signature may be measurements on a weld where the process parameters are well documented. Multiple spatial signatures may be generated by repeating such measurement on many such welds (before and/or after PWHT). The signature may be further validated by alternative (e.g., destructive) testing that may not be practical in a field setting. Before PWHT and before welding the base material may also be inspected for residual stress from production of the pipe. In some embodiments the residual stress is inspected at low enough frequencies to measure residual stresses through the wall of the pipe at each inspection location and for two or more drive winding orientations.

Features of the spatial signatures before and after PWHT may be computed from the sensor response and changes in these features are used to assess the PWHT quality and determine whether PWHT was performed or not. If it is determined that PWHT was performed an assessment of quality is also possible. In addition, the library of spatial signatures and experience is used to assess the confidence in the PWHT assessment, the weld quality assessment, and/or the residual stress estimation data.

In some embodiments the anisotropy of the magnetic permeability is measured by scanning with the sensor in two different orientations. In one such embodiment the sensor is scanned with the linear drive first in the circumferential orientation and then scanned again with the linear drive in the axial orientation. In one such embodiment the anisotropy is determined in the region adjacent to the weld and on the weld and an anisotropy level below a prescribed level indicates that PWHT was performed. The prescribed level having been determined from scans on samples that had been both properly PWHT and samples that did not have PWHT.

In some embodiments, features of the shape of the sensor response are tracked for many welds and the statistics of these features, possibly for thousands of inspected welds are recorded and stored. These statistics are then used to determine if the population of welds, or a subpopulations, were welded correctly (for data taken after welding) or PWHT correctly (for data taken after PWHT). The data may be tracked over time to look for changes in residual stresses after land motion or seismic events or after operation and long term service exposure, perhaps at high temperatures. This data is then used to support decisions regarding fitness for service, or as part of an overall pipeline integrity program.

In performing the above inspection a scanning fixture may be used to scan the sensor along the pipe with the sensor drive winding dominantly in a prescribed direction. The scanning fixture may have wheels oriented to permit circumferential travel along the pipe. In some embodiments a frame is used to maintain an approximately constant distance to the center of the pipe and to enable smoother scanning at nearly constant speed with a single motor. The drive winding orientation may be circumferential, axial or at an angle (e.g., 45 degrees). The circumferential and axial drive orientations will have greatest sensitivity to the axial and circumferential components of the permeability, respectively. Positioning the drive winding at an angle of course will result in a combined response.

In some embodiments the drive winding is excited at a frequency under 200 Hz. Magnetoresistive sensing elements are used to provide sensitivity deeper into the material than inductive elements and assess both surface and subsurface residual stresses. Inspection may be performed before PWHT to assess the weld quality and residual stress state for the base material and after PWHT to assess the PWHT process and determine if deleterious stresses remain in the pipe. Though, in some applications it may not be possible to perform inspection before PWHT (e.g., the PWHT may have already been completed). Measurements made after PWHT may be spatially registered with measurements taken before PWHT.

For some embodiments the inspection can be performed through a coating on the outer surface of the pipe.

In some embodiments an inductive sensing sensor may be used to achieve a higher quality response to near surface residual stress and metallurgical property variations with process parameters adjusted accordingly as necessary (e.g., sensor excitation frequency).

The inventors provide an apparatus and methods for determining the quality of a weld that uses a mechanical scanner to move a conformable array with a plurality of sensing elements and at least one linear drive conductor across the weld. This can be accomplished from either the inside or outside of a pipeline or on a flat or otherwise curved surface to inspect welds. In one such embodiment the sensors are mounted on an in-line inspection tool with multiple arcs that match the internal curvature of the pipe. Each arc has a single rectangular drive conductor or a dual rectangle drive conductor and either one or two rows of sensing elements located at the center of the one or two rectangles, respectively. In one such embodiment the tool moves at variable speed down a pipe propelled by the gas product flow and impedance data is recorded for at least one prescribed frequency. The goal is to provide weld quality assessment both with and without Post Weld Heat Treatment (PWHT). In one embodiment of this invention the goal is to provide an assessment of the stresses from the welding process either with or without PWHT. This stress at the welds is then used to determine the pipeline integrity and anticipate failures. Alternatively, this method is used to identify susceptible welds and remove them by cutting them out or remove the stresses by applying PWHT only to those welds that have excessive stresses.

In one embodiment of this invention an apparatus is provided where the sensing elements are inductive and the speed of the tool varies as the tool experiences varied pipeline elevation and the data rate is equal to a multiple of the time for a single drive current cycle at the lowest of one or more prescribed frequencies and where a precomputed database of sensor responses is used to convert the response at each sensing element into a magnetic permeability and lift-off value.

The inventors provide several different drive winding constructs each with a different purpose. In one such apparatus the linear drive conductor is oriented circumferentially and the magnetic permeability provides a combined measure of both metallurgical changes and axial stress. In another apparatus multiple linear drive conductors are included at equal spacing around the circumference but are oriented axially to provide a measure of the magnetic permeability in the circumferential, hoop, direction. In one such embodiment these axial conductor segments form a meander drive or several smaller meander drives that are driven with a drive current at least one prescribed frequency.

In one embodiment the magnetic permeability is correlated with stress in the weld and the weld quality is assessed based on the tensile stresses not exceeding a prescribed limit.

Section E-G: Crack Depth

Once a feature has been identified in the scans of an MWM-Array across a test material as a crack, it is useful to determine the length and depth of the crack since that affects remediation or disposition decisions. The crack length is typically obtained from the scan images of the sensor responses. The crack depth can be estimated from the previously developed correlations or analytical models for the sensor responses. The following provides a description of a method based on measurements performed on pipe sections with EDM notches of various known lengths, depths, and proximities. These current measurements establish correlation curves between the MWM responses and the notch depth and also permit the generation of the hybrid measurement grids or lattices that facilitate the rapid conversion of the MWM responses into depth information. A similar approach can be used with crack or notch models for the sensor response instead of the correlation with measurement responses.

To develop the correlation curves, measurements were performed on two steel pipe sections that were fabricated with EDM notches. The sample specimens are 3 ft long, 8 in. OD Schedule 40 and Schedule 80 steel pipe sections. The specimens contained a series of notches of different lengths and different depths. For the schedule 40 pipe, the isolated (single) notches had lengths of length 1.0 or 2.0 in. and depths that varied from 0.040 in. to 0.20 in. For the schedule 80 pipe, the isolated notches have a length of 2.0 in. and depths that varied from 0.020 in. to 0.25 in. Both pipe specimens also contained 5 pairs of notches that had different spacing between the notches and a depth of 0.040 in. for the schedule 40 pipe and 0.080 in. for the schedule 80 pipe. This included three pairs of 1.0 in. long notches with spacings of 0.25, 0.12, and 0.06 in. and two pairs of 0.5 in. long notches with spacings of 0.12 and 0.06 in.

Figure 56:
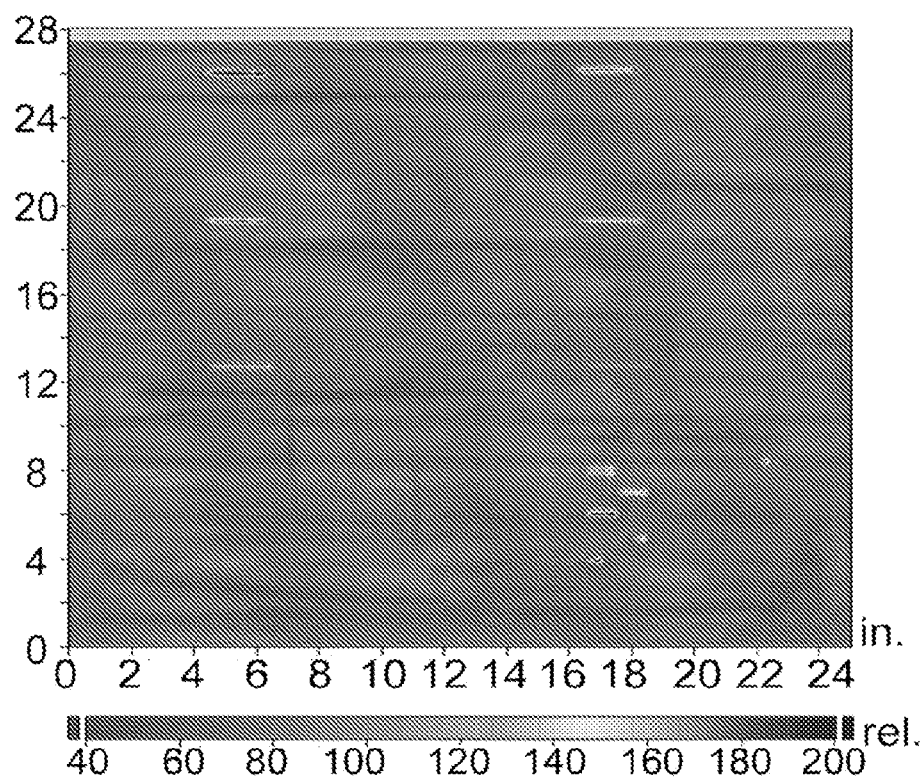

FIG. 56 shows a representative scan image of the effective permeability, obtained by processing the sensor responses through a permeability/lift-off measurement grid for an infinite half-space of material, for the schedule 80 pipe sample obtained with the FA24 at a lift-off of 0.040 in. The FA24 was oriented with the drive winding perpendicular to the notch orientation; this orientation has the drive winding oriented parallel to the hoop or circumferential direction of the pipe. These images assumed an electrical conductivity of 8% IACS and used an excitation frequency of 10 kHz. Similar results were obtained at other excitation frequencies up to 100 kHz, which is consistent with these measurements being in a "high frequency" regime where the skin depth is small and the induced currents are essentially surface currents. For both lift-offs, there is an increase in the effective (or apparent) permeability around the EDM notches and the magnitude of the change varies with the depth of the notch. Slowly varying background variations in the permeability are also observed; these are typical of as-manufactured steels.

Figure 58:
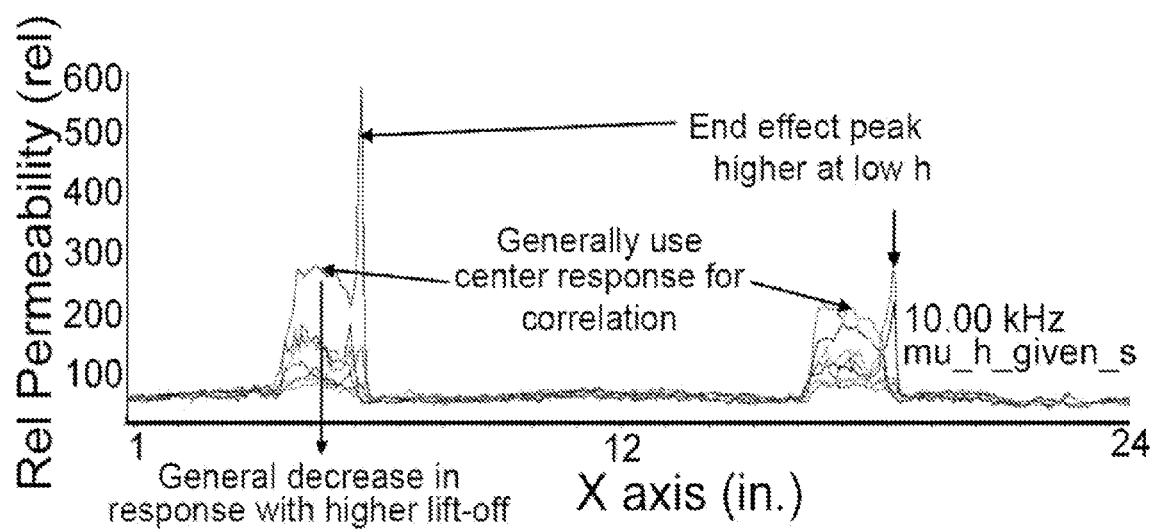

FIG. 58 shows representative B-scan plots of the responses for several channels that were in or near the scan path for the deepest notches of the schedule 80 pipe. This plot shows that the background variations in the permeability are small compared to the substantial increase in the permeability observed for the sense elements that passed directly over the notches. For this sensor there is a noticeable peak in the response at the end of each notch response; this is associated with the asymmetric sensor design and the relatively large spatial wavelength for this sensor array. This peak tended to be larger for the smaller lift-offs. Since the central portion of the response was observed to be much more representative of the notch depth than the end effect response, the central response was used when developing correlations between the sensor response and the notch depth.

Figure 57:
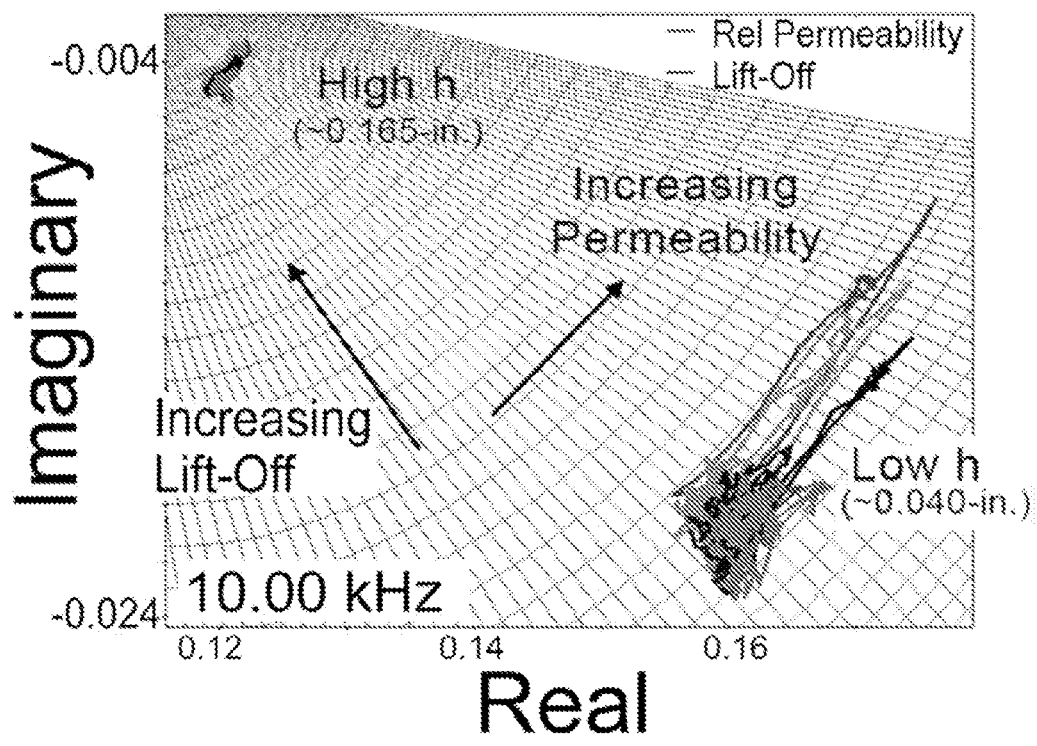

FIG. 57 shows an impedance view of a permeability/lift-off measurement grid and the FA24 data at two lift-offs. This measurement grid assumed an infinite half-space of material and did not model the crack response itself. The notch responses generally move in the same direction as the permeability so the effective permeability provides a reasonable parameter to measure and correlate with the notch depths. For other materials and/or other excitation frequencies, it may be desirable to choose a different parameter for correlating with the crack or notch depth. The same type of response is observed at the higher lift-offs, but the absolute change in the impedance responses associated with the notches are reduced since the sensor is farther away from the steel surface. This can make the higher lift-off measurements more sensitive to instrumentation noise and can also reduce sensitivity to the depth of the deeper notches since more of the sensing field drops across the lift-off layer. This implies that there is a balance where an intermediate lift-off can be chosen that will have both a reduced sensitivity to the end effects and also a reduced sensitivity to instrumentation noise.

Figure 59:
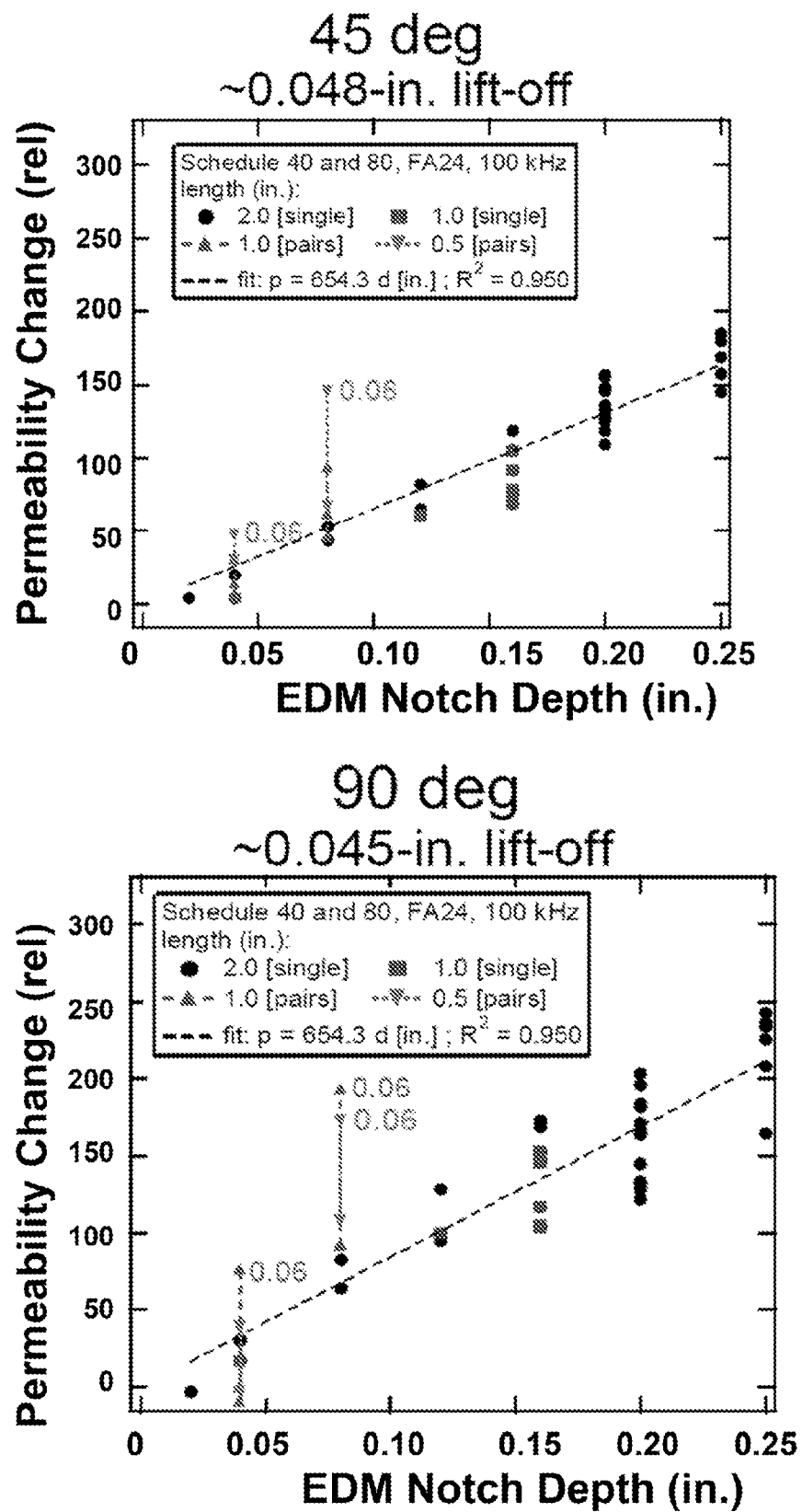

FIG. 59 (left) shows a representative correlation curve between the effective permeability change and EDM notch depth for the MWM-Array drive winding oriented perpendicular to the notch length. The effective permeability change is obtained from the MWM-Array sense element that passes over the notch and is the difference in the average permeability of the notch response and the baseline permeability of the unflawed material. The excitation frequency was 100 kHz and the nominal sensor lift-off to the steel pipe surface was 0.045 in. Similar results were also obtained at 10, 40 and 63 kHz. Measured notch data for both pipes is presented. For single notches, there is generally a linear increase in the effective permeability with notch depth for this sensor array and depths less than 0.25 in. This linear correlation is observed when the spatial wavelength is approximately twice the notch depth or larger. Otherwise, for small spatial wavelength sensors the effective permeability response can saturate and does not increase with depth for large depths. The slope of the correlation line tends to decrease as the lift-off increases, which suggests that smaller lift-offs are better to obtain greater sensitivity to the notch depth.

This plot also illustrates the effect of notch interactions. The responses to the pairs of notches show that interactions between the notches increase as the spacing between the notches decreases. The significance of this type of interaction is usually only significant for crack clusters, as with SCC; the effect of the interaction is to cause an overestimate of the depth when the responses from multiple shallow notches interact. Two approaches to reduce the effect of the interactions are to scan with a higher spatial resolution MWM-Array and to rotate the MWM-Array to an angle such as 45°. FIG. 59 (right) shows the permeability versus depth correlation curves obtained with the FA24 oriented at a 45° orientation. For the single notch data, there was less scatter in the data for the 45° orientation. This is also apparent in the correlation coefficient values. The interaction effects are also smaller for the 45° orientation. This confirmed that the higher spatial resolution data obtained with the angled MWM-Array could improve the accuracy of the depth sizing correlation.

For estimating the crack depths, the measurement data from scans with the MWM-Array can be processed within the GridStation software environment using standard algorithms that solve for multiple unknown properties from the appropriate measurement grids or lattices. For example, one instance of this algorithm analyzed used the measurement data to estimate the permeability and lift-off. The scan image of the data is then used to identify local property changes associated with the cracks, crack clusters, or notches. This also allows the background permeability of the pipe to be determined and can be used to confirm that the lift-off is reasonable. This background permeability value is then used as an input to a second multiple unknown algorithm that uses a depth/lift-off grid to provide the depth estimates. The results of the second application of the multiple unknown algorithm can be displayed in the form of a scan image. As alternatives, the depth lattice can also include the sensor orientation and the background lift-off as lattice parameters. This would allow a single, albeit larger lattice, to be used to accommodate a wide range of base material permeabilities, lift-offs, and sensor orientations.

Figure 60:
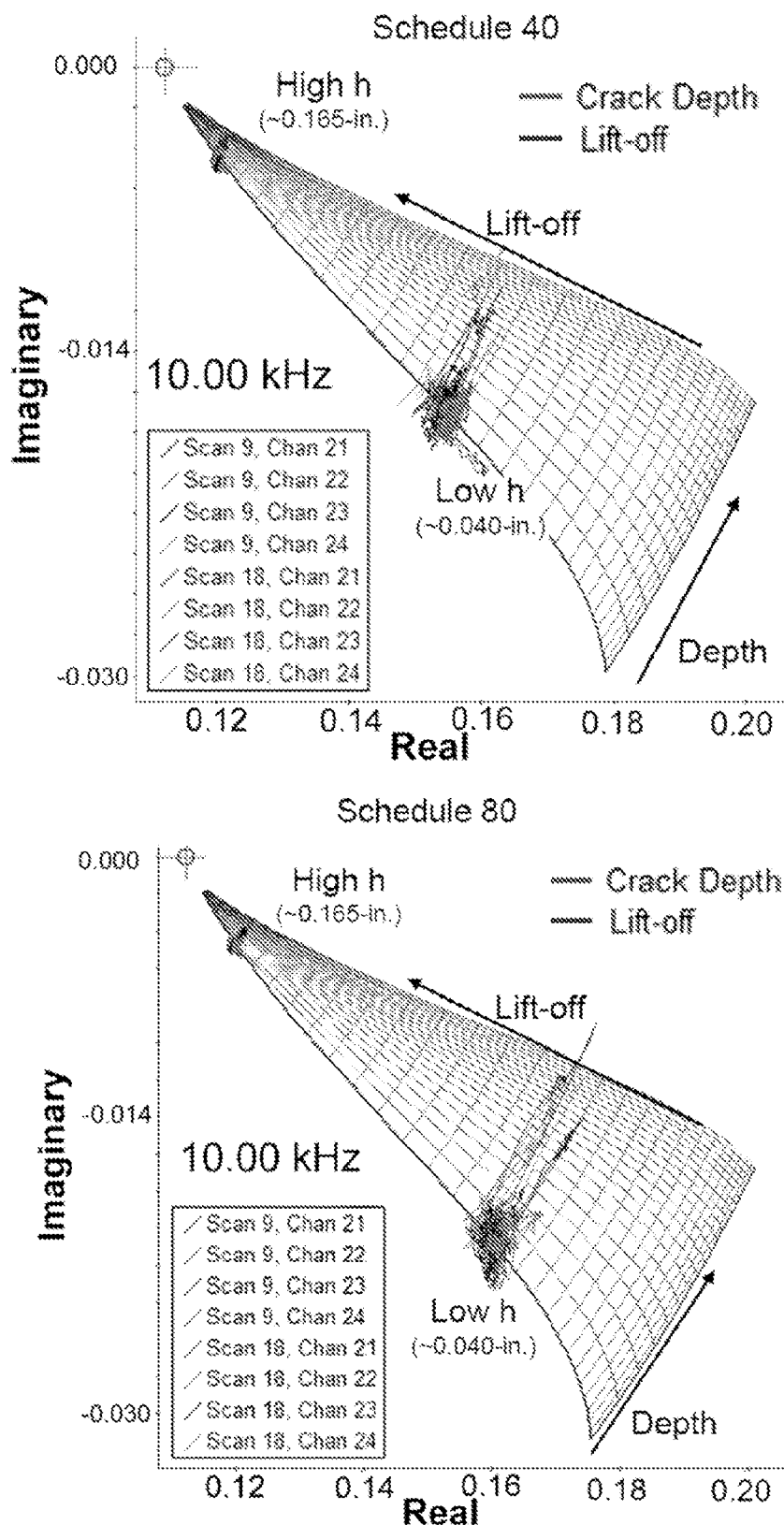

FIG. 60 provides representative depth/lift-off measurement grids. These grids represent slices of a permeability/depth/lift-off measurement grid lattice where the appropriate background permeability is chosen for each pipe section. The depth/lift-off grid incorporates the correlation between the MWM response and the notch depth from the reference measurements performed on the pipe sections. In generating the grid, an infinite half-space material model is used for preselected ranges of the baseline permeability, depth, and lift-off. For each baseline permeability, depth, and lift-off value, the depth is converted into the effective permeability change using the correlation curve and used to determine the corresponding total effective permeability for an infinite half-space of material associated with that notch depth. This total effective permeability is then used with the unflawed infinite half-space model to determine the effective sensor response to this notch depth. This process is repeated until the entire range of each parameter (baseline permeability, depth, and lift-off) is covered. As mentioned above, this process can be extended to include sensor orientation and baseline lift-off as well.

FIG. 61 shows representative scan images of the effective permeability over the surface of the pipe and the depth estimate image. Note that the effective permeability is the same as the absolute permeability far away from the notches since uniform layer model used to generate the permeability/lift-off grids apply in these regions. In some embodiments the color scale for the depth estimate image is chosen so that small (or negative) depths that result from application of the algorithm to unflawed areas that may have slight material property variations will be appear in the background color for the image. The intensity of the selected color, such as blue or grey scale, in the image increases with the observed depth and regions with responses deeper than the threshold value, which in this case is 0.200 in., appear in a second color, such as red or white. Note that similar results are obtained when all of the frequencies (10, 40, 63, and 100 kHz) are used simultaneously to estimate the crack depths or when individual frequencies are used.

Section E-H: Further Applications

In some embodiments the impedance instrument and probe electronics unit module that are combined to reduce complexity, use low power consuming components, use two or fewer simultaneous frequencies. This may be accomplished to minimize power consumption and eliminate the need for fans so the tool can operate in difficult environments. The impedance instrument and probe electronics provide current at least one prescribed frequency to drive a linear segment of at least one drive conductor. The impedance instrument supports and probe electronics provide capability to simultaneously measure impedance for each of at least two sensing elements, where the components of the impedance are measured simultaneously at the at least one frequency. The cable from the probe electronics to the sensor provides for the at least one drive current and return, and said cable supports fully parallel voltage measurement for each of the at least two sensing elements. High data resolution is achieved as compared to the frequency with filtering close to the sensor.

The impedance instrument and probe electronics may be housed within a housing and the cables to the sensors may support an eddy current array that is used to scan the inside of a pipeline. The sensor array response at a plurality of sensing elements is used to determine the longitudinal stress on the internal surface of the pipeline using a drive conductor that is aligned in the circumferential direction. The sensor array response at a plurality of sensing elements may be used to detect cracks initiating from the internal surface of the pipeline. The sensor array response at a plurality of sensing elements is used to detect corrosion wall loss on the internal surface of the pipeline. The sensor array response may be used to measure mechanical damage in the pipeline, to assess weld related conditions in a pipeline, to determine if PWHT was performed properly, to detect cracks at seam welds initiating from the internal surface of the pipeline, to detect cracks at girth welds initiating from the internal surface of the pipeline The impedance instrument may be separated from a probe electronics unit module, where the probe electronics unit is attached directly to a sensor with no cable length between them, and where the impedance instrument and probe electronics provide current at at least one prescribed frequency to drive a linear segment of at least one drive conductor, and the impedance instrument supports and probe electronics provide capability to simultaneously measure impedance for each of at least two sensing elements, where the components of the impedance are measured simultaneously at the at least one frequency.

A cable from the probe electronics to the sensor provides for at least one drive current and return, and said cable supports fully parallel voltage measurement for each of the at least two sensing elements.

The sensor may be flexible and have two rectangular drive conductors with at least one linear array of MR sensing elements located at the mid-point of one of the two rectangles. A precomputed database of sensor responses may be used to detect external and internal corrosion in a pipeline through insulation and metallic weather jacket, by estimating the lift-off, conductivity-thickness product, insulation thickness and pipeline wall thickness, using at least two frequencies. The weather jacket overlap may be accounted for using a database of responses to improve the capability to detect damage under the overlap. A stationary measurement is made at a location that does not have corrosion to estimate the conductivity of the pipe given an assumed nominal wall thickness, where the conductivity is then used to estimate wall thickness and detect and size corrosion damage for the rest of the pipe segment. The response at locations on the pipeline that do not appear to have corrosion is used with an assumed nominal wall thickness to estimate the average nominal conductivity of the pipe segment and this conductivity is used at other locations to detect and size corrosion related wall loss and to estimate confidence in the detection and sizing capability. The sensor may be flexible and have at least one rectangular drive conductors with at least one linear array of MR sensing elements located at the mid-point of the rectangular drive. A second array of sensing elements is located at the mid-point of the second rectangle. The sensor response at a plurality of sensing elements may be used to detect damage. The sensor response is used to provide an estimate of the damage size using a correlation relationship determined separately. The damage may be mechanical damage and the lift-off may be used to provide a geometric measure of a mechanical damage profile and the magnetic permeability is used to assess the stress at the dent. The damage may be mechanical damage and the lift-off is used to provide a geometric measure of a mechanical damage profile and the magnetic permeability is used to detect cracks. The sensor response may be used to estimate the magnetic permeability and the magnetic permeability variation is used to detect hard spots. The sensing elements may be inductive. The sensing elements may be magnetoresistive. Though, there may be other sensing element types.

The system may be used to inspect risers on an offshore platform, above or below water.

The data rate and channel count may be constrained in some embodiments. Exceeding the constrained number of channels may be achieved by stacking systems. Power may be divided between the excitation frequencies in any suitable way.

In some embodiments, sensor are permanently installed for fatigue and torque measurement. In some embodiments, the sensor response is used to analyze a fluid flowing within a pipe. In some embodiments, the pipe is plastic and the fluid is petrochemical in nature. In some embodiments, the sensor response is used to measure moisture in oil.

The sensor may be mounted on a mechanical scanner for inspection of a part from one side through a gap that is filled with a good insulator. In some embodiments, the good insulator layer is comprised of a layer of air and a coating layer.

Two frequencies may be used, where one frequency is high enough that it does not substantially penetrate through the pipe wall and one frequency is low enough that it does substantially penetrate through the pipe wall, where the data sampling rate is substantially higher than the lower frequency, where the higher resolution data is used to detect changes in the pipe condition that have a smaller dimension than the distance traveled by the tool during one period of the lower frequency response. Two frequencies responses may be used to measure the wall thickness and to detect anomalies that correspond to wall thinning. The two frequency responses may be used to detect cracks in the pipe. Higher resolution data may be filtered to provide an estimate of the size of a local damage anomaly.

An apparatus as in 1 where the sensor response is used to characterize a thin conducting layer by utilizing the phase measurement resolution to discriminate different layer conditions, where the skin depth is larger than the layer thickness and the conductivity thickness product of the layers produce is low enough to produce a phase of less than 1 degree.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

In this respect, it should be appreciated that one implementation of the above-described embodiments comprises at least one computer-readable medium encoded with a computer program (e.g., a plurality of instructions), which, when executed on a processor, performs some or all of the above-discussed functions of these embodiments. As used herein, the term "computer-readable medium" encompasses only a computer-readable medium that can be considered to be a machine or a manufacture (i.e., article of manufacture). A computer-readable medium may be, for example, a tangible medium on which computer-readable information may be encoded or stored, a storage medium on which computer-readable information may be encoded or stored, and/or a non-transitory medium on which computer-readable information may be encoded or stored. Other non-exhaustive examples of computer-readable media include a computer memory (e.g., a ROM, a RAM, a flash memory, or other type of computer memory), a magnetic disc or tape, an optical disc, and/or other types of computer-readable media that can be considered to be a machine or a manufacture.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. An impedance instrument comprising:
   a signal generator having
      a reference signal generator configured to generate reference signals at a plurality of frequencies, each frequency having an in-phase reference signal and a quadrature reference signal, the quadrature reference signal being a version of the in-phase reference signal shifted one-quarter period;
      a combiner to generate a combined signal by applying a weight to each in-phase reference signal and adding the weighted in-phase reference signals; and
      a module to generate and output an excitation signal by at least amplifying the combined signal; and
   a sense channel having:
      an analog-to-digital converter to digitize a response signal into n successive digitized samples; and
      a multiply/accumulate module to separately multiply the n successive digitized samples by respective samples of respective reference signals, to separately add products of the multiply associated with each reference signal, and divide each total by n to produce complex impedance measurements at each of the plurality of frequencies.

2. The impedance instrument of claim 1, wherein the sense channel is among a plurality of parallel sensing channels each having a respective multiply/accumulate module.

3. The impedance instrument of claim 1, wherein the multiply/accumulate module is configured to simultaneously process the successive digitized samples of the digitized response signal by independently at least multiplying the digitized samples by the in-phase and quadrature reference signals.

4. The impedance instrument of claim 1, wherein, for each frequency, the multiply/accumulate module produces a real part of the complex impedance measurement from the digitized samples processed with the respective in-phase reference signal, and the multiply/accumulate module produces an imaginary part of the complex impedance measurement from the digitized samples processed with the respective quadrature reference signal.

* * * * *